United States Patent
Tran et al.

(10) Patent No.: US 9,238,034 B2
(45) Date of Patent: Jan. 19, 2016

(54) FN14 ANTAGONISTS AND THERAPEUTIC USES THEREOF

(71) Applicant: THE TRANSLATIONAL GENOMICS RESEARCH INSTITUTE, Phoenix, AZ (US)

(72) Inventors: Nhan Tran, Phoenix, AZ (US); Nathalie Meurice, Scottsdale, AZ (US); Harshil Dhruv, Phoenix, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 0 days.

(21) Appl. No.: 14/327,448

(22) Filed: Jul. 9, 2014

(65) Prior Publication Data

US 2015/0017263 A1  Jan. 15, 2015

Related U.S. Application Data

(60) Provisional application No. 61/844,336, filed on Jul. 9, 2013, provisional application No. 61/880,544, filed on Sep. 20, 2013.

(51) Int. Cl.

| | |
|---|---|
| *A61K 31/47* | (2006.01) |
| *A61K 31/542* | (2006.01) |
| *A61K 31/53* | (2006.01) |
| *A61K 45/06* | (2006.01) |
| *A61K 31/541* | (2006.01) |
| *A61K 31/4192* | (2006.01) |
| *A61K 31/4188* | (2006.01) |
| *A61K 31/4704* | (2006.01) |
| *A61K 31/4745* | (2006.01) |
| *A61K 33/24* | (2006.01) |

(52) U.S. Cl.
CPC ........... *A61K 31/542* (2013.01); *A61K 31/4188* (2013.01); *A61K 31/4192* (2013.01); *A61K 31/4704* (2013.01); *A61K 31/4745* (2013.01); *A61K 31/53* (2013.01); *A61K 31/541* (2013.01); *A61K 33/24* (2013.01); *A61K 45/06* (2013.01)

(58) Field of Classification Search
CPC .................................................. A61K 31/4192
USPC ......................................... 544/60; 514/227.8
See application file for complete search history.

(56) References Cited

U.S. PATENT DOCUMENTS

| 8,329,657 B2 | 12/2012 | Tykocinski et al. |
| 2002/0015703 A1 | 2/2002 | Rennert |
| 2012/0053220 A1 | 3/2012 | Van Leyen et al. |

FOREIGN PATENT DOCUMENTS

| WO | WO 2012/080729 A2 * | 6/2012 |
| WO | 2013/026099 A1 | 2/2013 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Dhruv et al., "Structural Basis and Targeting of the Interaction between Fibroblast Growth Factor-inducible 14 and Tumor Necrosis Factor-like Weak Inducer of Apoptosis", The Journal of Biological Chemistry, 288(45):32261-32276 (Sep. 20, 2013).
Dhruv et al., "Tumor necrosis factor-like weak inducer of apoptosis (TWEAK) promotes glioblastoma cell chemotaxis via Lyn activation", Carcinogenesis, 35(1):218-226 (2014).
Fortin et al., "Tumor Necrosis Factor-Like Weak Inducer of Apoptosis Stimulation of Glioma Cell Survival is Dependent on Akt2 Function", Mol Cancer Res., 7:1871-1881 (Oct. 27, 2009).
The International Search Report and The Written Opinion of the International Searching Authority, or the Declaration dated Jan. 29, 2015 for PCT/US2014/046047.
Pellegrini et al., "Structure of the extracellular domains of human and Xenopus Fn14: implications in the evolution of TWEAK and Fn14 interactions", FEBS Journal, 280 (1818-1829 (2013).
Prasad et al., "Exploring in silico affinity of flavonoids and tannins to human fibroblast growth factor-induciblel4 (fn14), a member of TNF receptor super family", Bioinformation, 9:633-638 (Jul. 12, 2013).
Tran et al., "The Tumor Necrosis Factor-like Weak Inducer of Apoptosis (TWEAK)-Fibroblast Growth Factor-Inducible 14 (Fn14) Signaling System Regulates Glioma Cell Survival via NFkB Pathway Activation and BCL-XL/BCL-W Expression", The Journal of Biological Chemistry, 280(5):3483-3492 (Dec. 16, 2004).
Whitsett et al., "Mcl-1 Mediates TWEAK/Fn14-Induced Non-Small Cell Lung Cancer Survival and Therapeutic Response", Mol Cancer Res., 12:550-559 (Jan. 27, 2014).

* cited by examiner

*Primary Examiner* — Deepak Rao

(57) ABSTRACT

The present disclosure is directed to methods of using fibroblast growth factor-inducible 14 (Fn14) antagonists to modulate activity at a TNF-like weak inducer of apoptosis (TWEAK) binding site on a cysteine-rich domain (CRD) of Fn14. The present disclosure also provides pharmaceutical compositions comprising synergistic combinations Fn14 antagonists and chemotherapeutic agents.

9 Claims, 24 Drawing Sheets

| | |
|---|---|
| TWEAK | SAPKGRKTRARRAIAAHYEVHPRPGQD--GAQAGVDGTVSGWEEARINSS |
| 1SS5  | ----------AQPFAHLTINA-ASIPSGSHKVTLSSWYHDRGWAKIS-N |
| 1TNR  | ----------KPAAHLIGDP-SKQN------SLLWRANTDRAFLQDG |
| 1XU2  | --------KHSVLHLVPVN-ITSKADSDVTE-VMWQP---VLRRGRG |
| 2E7A  | ----------PSDMPVAHVVANPQAEG--------QLQWINRRANALLANG |
| 2RJL  | ----------GDKPRAHLTVRQIPT----QFPA-LHWEHELGLAFTKNR |
| 2X29  | ---DPAGLLDLRQGMFAQIVAQNVLLI-----DGP-LSWYSDPGLAGVSLT |

| | |
|---|---|
| TWEAK | SPLRYNRQIGEFIVTRAGLYYLCQVHFDE--------GKAVYLKLDLLV |
| 1SS5  | MTL----SNGKLRVNQDGFYYLYANICFRHHETSGSVPTDYLQMVYVVK |
| 1TNR  | FSL----SNNSLLVPTSGIYFVYSQVVFSGKAYSPKATSSPLYLAHEVQL |
| 1XU2  | LEA----QGDIVRVWDTGIYLLYSQVLFHD--------VTFTMGQVVSR |
| 2E7A  | VEL----RDNQLVVPSEGLILIYSQVLFSGQG----CPSTHVLLTHTISR |
| 2RJL  | MNY----TNKFLLIPESGDYFIYSQVTFRGM-------KPDSITVVITK |
| 2X29  | GGLSYKEDTKELVVAKAGVYYVFFQMELRRVVAGE----GSGSVSLALHL |

| | |
|---|---|
| TWEAK | DGVLALRCLEEFSATAASSLG--------PQLRLCQVSGLLALRPGSSL |
| 1SS5  | TSIKIPSSHNLMKGGSTKNWSG-----NSEFHFTSINVGGFFKLRAGEEI |
| 1TNR  | FSSQYPFHVPLLSSQKMVYPGL-----QE-PWLHSMYHGAAFQLTQGDQL |
| 1XU2  | EG-QG-RRETLFRCIRSMPSDP--------DRAYNSCYSAGVFHLHQSDII |
| 2E7A  | ISTTHNQPVNLLSAIRSPCQHETPEGAEANPWYEPIYLGGVFQLEPGDRL |
| 2RJL  | VTDSYPEPTQLLMGTKSVSEVG------SNWFQPIYLGAMFSLQEGDKL |
| 2X29  | MP------AAALALTVDLPP--------RNSAFGFQGRLLHLSAGQRL |

| | |
|---|---|
| TWEAK | RIRTLPW----AHLKAAPFLTYFGLFQVH----- |
| 1SS5  | SIQV-SN--PSLLDP-DQDATYFGAFKVQDID--- |
| 1TNR  | STHT-DG--IPHLVL-SPSTVFFGAFAL------ |
| 1XU2  | TVKIPRA--NAKLSL-SPHGTFLGFVKL------ |
| 2E7A  | SAEI-NR--PDYLDFAESGQVTFGIIAL------ |
| 2RJL  | MVNV-SD--ISLVDYTKEDKTFFGAFLL------ |
| 2X29  | GVHLHTERRARHAWQLTQGATVLGLFRVTPEIPA |

```
                            SEQUENCE LISTING

<160> NUMBER OF SEQ ID NOS: 2

<210> SEQ ID NO 1
<211> LENGTH: 249
<212> TYPE: PRT
<213> ORGANISM: Homo sapiens

<400> SEQUENCE: 1

Met Ala Ala Arg Arg Ser Gln Arg Arg Gly Arg Arg Gly Glu Pro
1               5                   10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
                35                  40                  45

Ser Leu Ser Ala Gln Glu Pro Ala Gln Glu Glu Leu Val Ala Glu Glu
    50                  55                      60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
                100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
        130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
                180                 185                 190

Glu Glu Phe Ser Ala Thr Ala Ala Ser Ser Leu Gly Pro Gln Leu Arg
            195                 200                 205

Leu Cys Gln Val Ser Gly Leu Leu Ala Leu Arg Pro Gly Ser Ser Leu
    210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 2
<211> LENGTH: 129
<212> TYPE: PRT
<213> ORGANISM: Homo sapiens

<400> SEQUENCE: 2

Met Ala Arg Gly Ser Leu Arg Arg Leu Leu Arg Leu Leu Val Leu Gly
1               5                   10                  15
```

```
Leu Trp Leu Ala Leu Leu Arg Ser Val Ala Gly Glu Gln Ala Pro Gly
        20              25              30

Thr Ala Pro Cys Ser Arg Gly Ser Ser Trp Ser Ala Asp Leu Asp Lys
        35              40              45

Cys Met Asp Cys Ala Ser Cys Arg Ala Arg Pro His Ser Asp Phe Cys
    50              55              60

Leu Gly Cys Ala Ala Ala Pro Pro Ala Pro Phe Arg Leu Leu Trp Pro
65              70              75              80

Ile Leu Gly Gly Ala Leu Ser Leu Thr Phe Val Leu Gly Leu Leu Ser
            85              90              95

Gly Phe Leu Val Trp Arg Arg Cys Arg Arg Arg Glu Lys Phe Thr Thr
            100             105             110

Pro Ile Glu Glu Thr Gly Gly Glu Gly Cys Pro Ala Val Ala Leu Ile
        115             120             125

Gln
```

FN14 ANTAGONISTS AND THERAPEUTIC USES THEREOF

CROSS REFERENCE TO RELATED APPLICATIONS

This application claims priority to and the benefit of U.S. Provisional Application Ser. No. 61/844,336, filed on Jul. 9, 2013 U.S. Provisional Application Ser. No. 61/880,544, filed on Sep. 20, 2013, the contents of each, which are hereby incorporated by reference in their entirety.

GOVERNMENTAL SUPPORT OF APPLICATION

This invention was made with governmental support under grant number CA130940 awarded by the National Institutes of Health and grant number MH090878 from the National Institute of Mental Health. The United States government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 3,677 byte ASCII (text) file named "Seq_List" created on Jul. 9, 2014.

TECHNICAL FIELD

This application relates to compositions comprising Fn14 antagonists and methods of their use to modulate the TWEAK-Fn14 pathway and to ameliorate or treat disease states such as cancer, autoimmune disease, and cardiovascular disease.

BACKGROUND

The TNF-like weak inducer of apoptosis (TWEAK) is a multifunctional cytokine involved in many cellular activities including proliferation, migration, differentiation, apoptosis, angiogenesis and inflammation (Wiley S R, Winkles J A (2003) Cytokine Growth Factor Rev 14: 241-249). TWEAK is a type II transmembrane protein that consists of an N-terminal cytoplasmic domain followed by a single transmembrane domain that is separated by a stalk region from the C-terminal Tumor Necrosis Factor (TNF) homology domain (THD) (Chicheportiche Y, Bourdon P R, Xu H, Hsu Y M, Scott H, et al. (1997) J Biol Chem 272: 32401-32410; Feng S L, Guo Y, Factor V M, Thorgeirsson S S, Bell D W, et al. (2000) Am J Pathol 156: 1253-1261). Membrane TWEAK is processed by a protease of the furin family resulting in a soluble ligand containing the THD. The THD functions in ligand trimerization and receptor binding causing TWEAK to signal as a trimerized molecule (Kolzsch J (1990) Z Arztl Fortbild (Jena) 84: 1199-1202; Kolfschoten G M, Pradet-Balade B, Hahne M, Medema J P (2003) Biochem Pharmacol 66: 1427-1432). Importantly, both membrane-bound and soluble TWEAK (sTWEAK) proteins are fully functional and can mediate similar cellular signaling effects by binding to cellular receptors (Brown S A, Ghosh A, Winkles J A (2010) J Biol Chem 285: 17432-17441).

TWEAK acts by binding to the fibroblast growth factor-inducible 14 (Fn14) receptor, the smallest member of the tumor necrosis factor receptor (TNFR) superfamily (Wiley S R, Winkles J A (2003) Cytokine Growth Factor Rev 14: 241-249; Meighan-Mantha R L, Hsu D K, Guo Y, Brown S A, Feng S L, et al. (1999) J Biol Chem 274: 33166-33176). TWEAK-mediated Fn14 signaling triggers a wide range of physiological activities in cells and tissues including blood clotting, cell proliferation, cell migration, inflammation, and angiogenesis (Harada N, et al. (2002) Biochem Biophys Res Commun 299: 488-493; Polek T C, et al. (2003) J Biol Chem 278: 32317-32323). The Fn14 receptor contains a single cysteine-rich domain (CRD) in the extracellular ligand-binding region and a short cytoplasmic tail possessing a single TNFR-associated factor (TRAF) binding site (Wiley S R, Winkles J A (2003) Cytokine Growth Factor Rev 14: 241-249; Meighan-Mantha R L, et al. (1999) J Biol Chem 274: 33166-33176). Notably, TWEAK is the only known TNF superfamily member that can bind to Fn14. Site-directed mutagenesis has demonstrated that TWEAK binding to the Fn14 CRD requires evolutionarily conserved amino acid residues (Asp45, Lys48 and Met50) and all three of the predicted disulfide bonds (Brown S A, Hanscom H N, Vu H, Brew S A, Winkles J A (2006) Biochem J 397: 297-304). Optimal TWEAK-mediated activation of Fn14 is important for promoting productive tissue responses after injury, but excessive TWEAK-Fn14 activation can induce pathological tissue responses, leading to progressive damage and degradation (Burkly L C, Michaelson J S, Zheng T S (2011) Immunol Rev 244: 99-114).

Over-expression of Fn14 has been reported in multiple cancers including glioblastoma, breast, pancreatic, esophageal, lung, and liver carcinomas (Feng S L, Guo Y, Factor V M, Thorgeirsson S S, Bell D W, et al. (2000) Am J Pathol 156: 1253-1261; Han H, Bearss D J, Browne L W, Calaluce R, Nagle R B, et al. (2002) Cancer Res 62: 2890-2896; Tran N L, McDonough W S, Donohue P J, Winkles J A, Berens T J, et al. (2003) Am J Pathol 162: 1313-1321; Watts G S, Tran N L, Berens M E, Bhattacharyya A K, Nelson M A, et al. (2007) Int J Cancer 121: 2132-2139; Willis A L, Tran N L, Chatigny J M, Charlton N, Vu H, et al. (2008) Mol Cancer Res 6: 725-734; Whitsett T G, Cheng E, Inge L, Asrani K, Jameson N M, et al. (2012) Am J Pathol 181: 111-120). In glioblastoma, Fn14 mRNA and protein expression is unregulated in migratory cells in vitro and invading cells in vivo (Tran N L, McDonough W S, Savitch B A, Fortin S P, Winkles J A, et al. (2006) Cancer Res 66: 9535-9542). Fn14 expression increases with increasing tumor grade with highest expression observed in glioblastoma multiforme (Grade IV). In contrast, the expression of Fn14 is minimal to absent in normal brain tissue. Moreover, TWEAK binding to Fn14 triggers glioma cell invasion and survival (Tran N L, McDonough W S, Savitch B A, Fortin S P, Winkles J A, et al. (2006) Cancer Res 66: 9535-9542).

TWEAK-Fn14 signaling plays a key role in various disease states and therefore holds significant therapeutic potential as a novel molecular target for developing anti-cancer and anti-autoimmune therapeutic agents in humans. It has been shown that this interaction plays a pivotal role in various immunological conditions like rheumatoid arthritis, systemic lupus erythematosus, multiple sclerosis, renal injury, ischaemic stroke, as well as cardiac dysfunction and failure (Burkly L C, et al. (2007) Cytokine 40:1-16; Winkles J A (2008) Nat Rev Drug Discov 7: 411-425; Jain M, Jakubowski A, et al. (2009) Circulation 119: 2058-2068). Several studies have confirmed the therapeutic potential of this pathway in human esophageal and pancreatic cancers, autoimmune disorders (Zheng T S, Burkly L C (2008) J Leukoc Biol 84: 338-347), muscle atrophy and injury (Bhatnagar S, Kumar A (2012) Curr Mol Med 12: 3-13) and chemokine-dependent inflammatory kidney disease (Campbell S, Burkly L C, Gao H X, Berman J W, Su L, et al. (2006) J Immunol 176: 1889-1898). The ever increasing knowledge and data on various downstream reactions stimulated by TWEAK-Fn14 interaction has recently been compiled into a complete repository (Bhattacharjee M, Raju R, Radhakrishnan A, Nanjappa V, Muthusamy B, et al. (2012) J Signal Transduct 2012: 376470). This paves the way for identification of yet unknown components of the signaling pathways.

To date, there are five anti-TNF antibody-based drugs already on the market and 16 out of approximately 22 ligand/receptor pairs under clinical development, constituting one of the most successful classes of biological therapeutics (Tansey M G, Szymkowski D E (2009) Drug Discov Today 14: 1082-1088). These protein-based therapeutics have some notable disadvantages including problems associated with drug delivery, stability, and cost. On the other hand, very few small molecule inhibitors targeting TNFR family members have been identified. Known small molecule inhibitors for the TNFR family act by disrupting trimerization of their respective ligands, as is the case for TNFα (He M M, Smith A S, Oslob J D, Flanagan W M, Braisted A C, et al. (2005) Science 310: 1022-1025) and CD40 (Silvian L F, Friedman J E, Strauch K, Cachero T G, Day E S, et al. (2011) ACS Chem Biol 6: 636-647). Benicchi and coworkers have also focused on the development of a Homogenous Time Resolved Fluorescence (HTRF) assay for identification of small-molecule inhibitors for TWEAK-Fn14 interaction and reported the identification of hits at a rate of 0.007% (Benicchi T, Iozzi S, Svahn A, Axelsson H, Mori E, et al. (2012) J Biomol Screen 17: 933-945). Currently, the potential therapeutic benefit of inhibiting key nodes of the TWEAK-Fn14 signaling pathway remains untapped due to the absence of small molecule tools to interrogate this pathway.

The importance of the Fn14 CRD has been established utilizing an NMR solution structure of this domain and functional mutation studies (Brown S A, Hanscom H N, Vu H, Brew S A, Winkles J A (2006) Biochem J 397: 297-304). The present disclosure is directed to compounds that target the CRD of Fn14 and modulate the TWEAK-Fn14 pathway. The present invention also provides a number of therapeutic uses of these compounds including in the treatment of autoimmune disease.

SUMMARY

The present invention is based on the characterization of the TWEAK-Fn14 interaction. Six structural models of TWEAK were built based on experimental structures of low homology templates from the TNF superfamily. Protein-protein docking, followed by data-driven prioritization, yielded two promising TWEAK-Fn14 binding hypotheses. Site directed mutagenesis confirmed one hypothesis providing a structural basis for target-based identification of small molecule inhibitors of the TWEAK-FN14 interaction. Validated models served as a basis for in silico library design. A targeted library of molecules was assembled and screened iteratively, leading to enrichment in activity for compounds with similar scaffolds. The identified compounds target the TWEAK-Fn14 interaction and provide therapeutic agents for the treatment of cancer including glioblastoma and other diseases.

In certain implementations, the present invention relates to a method of modulating the TWEAK-Fn14 pathway in a subject, the method comprising administering to the subject an Fn14 antagonist comprising a compound of Formula (I):

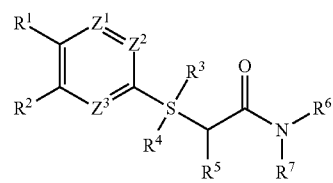

or a salt thereof, wherein each of $R^1$ and $R^2$ is independently —H, —OH, =O, —NH$_2$, —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), —N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), —SO$_2$NH$_2$,

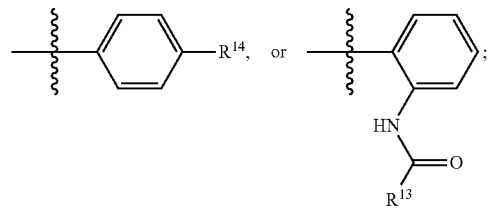

both $R^3$ and $R^4$ are absent or are =O;

$R^5$ is H, —OH, hydrocarbyl, aryl, aralkyl, heteroaryl, heterocyclyl, or

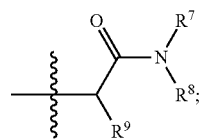

each of $R^6$, $R^8$, $R^9$, and $R^{12}$ is independently H, substituted or unsubstituted alkyl, substituted or unsubstituted heteroalkyl, substituted or unsubstituted —O-alkyl, or substituted or unsubstituted aryl, wherein $R^6$ and $R^9$ together with the nitrogen or carbon atom to which they are attached are optionally joined to form a substituted or unsubstituted heterocycloalkyl ring system having 6 members and containing at least one carbon-carbon double bond, $R^8$ and $R^9$ together with the nitrogen or carbon atom to which they are attached are optionally joined to form a substituted or unsubstituted heterocycloalkyl ring system having 5 members and containing at least one carbon-carbon double bond, and $R^9$ and $R^{12}$ together with the nitrogen or carbon atom to which they are attached are optionally joined to form a substituted or unsubstituted heterocycloalkyl ring system having 6 members and containing at least one carbon-carbon double bond;

R⁷ is H, hydrocarbyl, aryl, aralkyl, heteroaryl, heterocyclyl, or

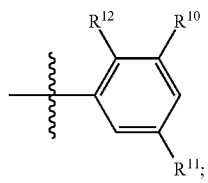

each of $R^{10}$, $R^{11}$, $R^{13}$ and $R^{14}$ independently is absent or is —H, —OH, halo, —$C_{1-6}$alkyl, or —O—$C_{1-6}$alkyl; and
each of $Z^1$, $Z^2$, and $Z^3$ is independently CH or N;
and a vehicle, excipient, and/or carrier.

In yet other embodiments, the present invention relates to a method of modulating the TWEAK-Fn14 pathway in a subject, the method comprising administering to the subject an Fn14 antagonist comprising a compound of Formula (II):

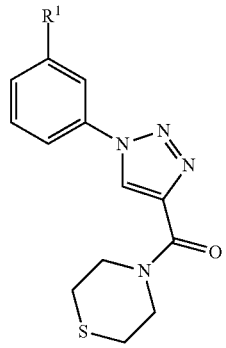

or a salt thereof, wherein
$R^1$ is —H, —OH, =O, —$NH_2$, —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —$OCF_3$, —C(O)O(alkyl), —OC(O)(alkyl), —C(O)$NH_2$, —C(O)NH(alkyl), —C(O)N(alkyl)(alkyl), —NHC(O)(alkyl), —N(alkyl)C(O)(alkyl), —OC(O)O(alkyl), —OC(O)$NH_2$, —OC(O)NH(alkyl), —OC(O)N(alkyl)(alkyl), —CHNH, —CHN(alkyl), —$SO_2NH_2$;
and a vehicle, excipient, and/or carrier.

In some aspects, the compounds of the present invention may be used to ameliorate or treat an autoimmune disease such as autoimmune hemolytic anemia, autoimmune neonatal thrombocytopenia, autoimmune neutropenia, autoimmunocytopenia, antiphospholipid syndrome, dermatitis, gluten-sensitive enteropathy, allergic encephalomyelitis, myocarditis, relapsing polychondritis, rheumatic heart disease, glomerulonephritis, Multiple Sclerosis, Neuritis, Uveitis Ophthalmia, Polyendo-crinopathies, Purpura, Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitus, autoimmune inflammatory eye, autoimmune thyroiditis, hypothyroidism, systemic lupus erythematosus, discoid lupus, Goodpasture's syndrome, Pemphigus, Graves' Disease, Myasthenia Gravis, and insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis, bullous pemphigoid, Sjogren's syndrome, diabetes mellitus, adrenergic drug resistance with asthma or cystic fibrosis, chronic active hepatitis, primary biliary cirrhosis, endocrine gland failure, vitiligo, vasculitis, post-MI, cardiotomy syndrome, urticaria, atopic dermatitis, asthma, inflammatory myopathies, an inflammatory disorder, a granulomatous disorder, an atrophic disorder, or an alloimmune disease.

In other aspects, the compounds of the present invention may be used to ameliorate or treat a cancer selected from the group consisting of a brain tumor, glioblastoma, breast cancer, prostate cancer, esophageal cancer, ovarian cancer, colon cancer, lung cancer, melanoma, pancreatic cancer, liver cancer, and renal cancer.

The present invention is also directed to a pharmaceutical composition comprising an Fn14 antagonist and a pharmaceutically acceptable vehicle, excipient, and/or carrier. In certain embodiments, the pharmaceutical composition further comprises a therapeutic agent for the treatment of cancer or an autoimmune disease wherein the combination of the Fn14 antagonist and the therapeutic agent results in a synergistic effect. The therapeutic agent may be any one of temozolomide, camptothecin, cisplatin, an Akt inhibitor, an NFκB inhibitor, an Mcl-1 inhibitor, a BCL-$X_L$ inhibitor, a BCL-2 inhibitor, a BCL-W inhibitor, an Src inhibitor, or a Lyn inhibitor. Such inhibitors are described in Druv et al., Carcinogenesis 35(1): 218-226, 2014; Tran et al., J Biol Chem 280(5): 3483-3492, 2005; Fortin et al., Mol Cancer Res 7: 1871-1881, 2009; and Whitsett et al., Mol Cancer Res 12: 550-559, 2014; the contents of which are hereby incorporated by reference.

Pharmaceutical compositions in accordance with the present invention may be administered either alone or in combination with one or more other therapeutic agents.

In some embodiments, compositions in accordance with the invention may be administered in combination with any therapeutic agent or therapeutic regimen that is useful to treat, alleviate, ameliorate, relieve, delay onset of, inhibit progression of, reduce severity of, and/or reduce incidence of one or more symptoms or features of an autoimmune disorder. For example, compositions in accordance with the invention may be administered in combination with traditional diabetes therapies including, but not limited to, insulin administration. To give another example, compositions in accordance with the invention may be administered in combination with soluble TNF receptor, anti-TNFα receptor, analgesics, non-steroidal anti-inflammatory agents (NSAIDs), and/or other agents may be useful for treatment of rheumatoid arthritis.

In certain aspects, administration of the Fn14 antagonist is oral, parenteral, intravenous, subcutaneous, intramuscular, intraperitoneal injection, or infusion. In other aspects, the Fn14 antagonist is administered to the subject in an amount of about 1 mg to about 1,000 mg.

BRIEF DESCRIPTION OF THE DRAWINGS

FIG. 2 depicts homology modeling for TWEAK. FIG. 2B, TWEAK sequence (black) aligned to the consensus structure-derived sequence alignment of the six template TNF ligands. The sequence alignment of the six template ligands, identified by their PDB ID and color-coded based on the chain color in panel a, was derived from the structure alignment. The TWEAK sequence was aligned onto the multiple alignment of the six templates.

DETAILED DESCRIPTION

Figure 1:
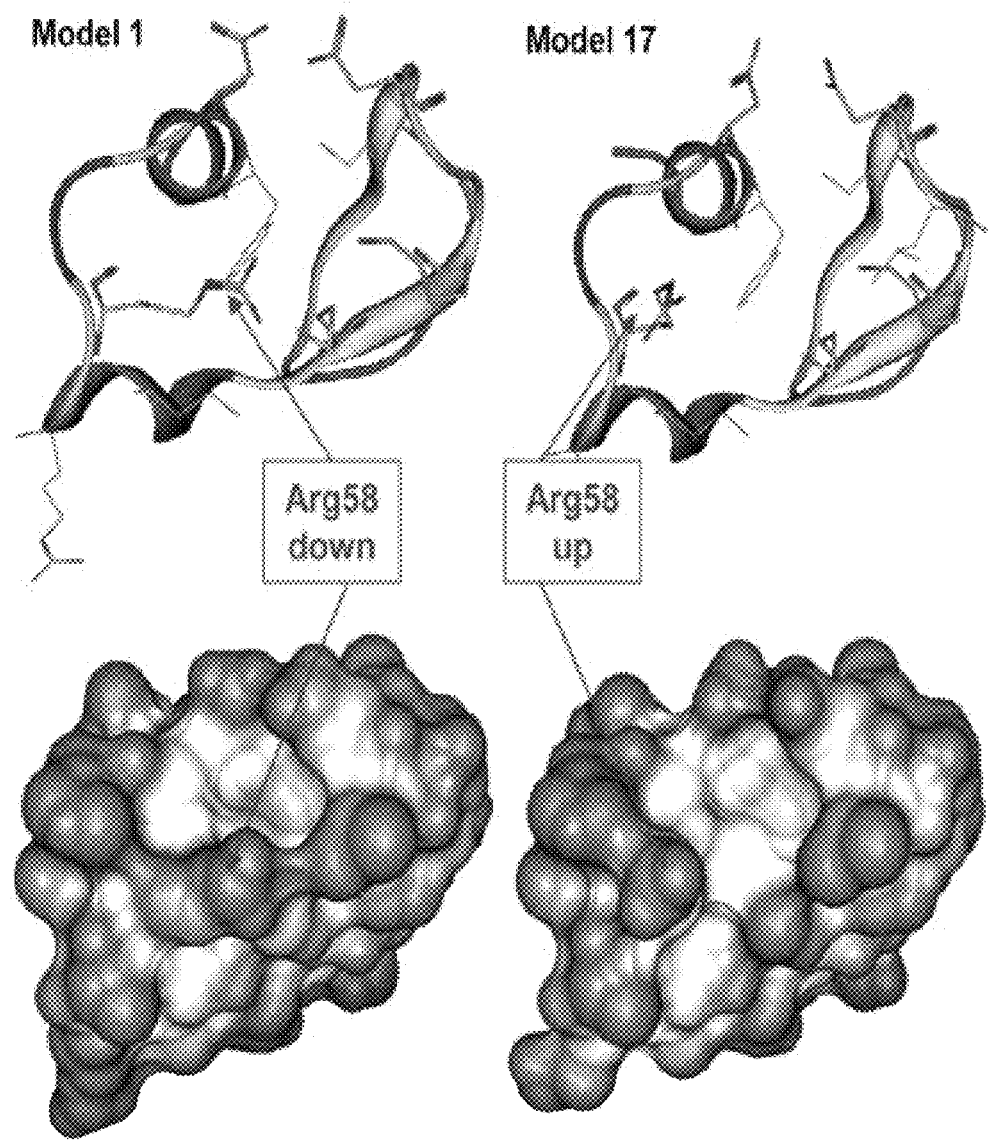
FIG. 1 depicts flexibility of R58 side chain in Fn14 CRD. The position of R58 side chain in models 1 and 17 of the Fn14 CRD NMR structure define closed and open states of the Fn14 binding site. Top views, the Fn14 CRD main chain is represented as a ribbon and key side chains are shown as sticks. Bottom views, the van der Waals surface of both Fn14 CRD models are represented, illustrating the changes in geometries associated with the different Arg58 side chain positions.

As used herein, the verbs "comprise" and "include" and their conjugations are used in their non-limiting sense to mean that items following the words are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

"Compound" and "compounds" as used herein refers to a compound encompassed by the generic formulae disclosed herein, any subgenus of those generic formulae, and any forms of the compounds specified by the generic and subgeneric formulae, such as a pharmaceutically acceptable salt. Unless specified otherwise, the term further includes the isotopes, racemates, stereoisomers, and tautomers of the compound or compounds.

"Isotopes" refer to pharmaceutically acceptable isotopically-labeled compounds wherein one or more atoms are replaced by atoms having the same atomic number, but an atomic mass different from the atomic mass usually found in nature. Suitable isotopes include isotopes of hydrogen, such as $^2H$ and $^3H$. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

"Racemates" refers to a mixture of enantiomers.

"Solvate" or "solvates" of a compound refer to those compounds, where compounds are as defined herein, that are bound to a stoichiometric or non-stoichiometric amount of a solvent. Solvates of a compound includes solvates of all forms of the compound such as the oxide, ester, prodrug, or pharmaceutically acceptable salt of the disclosed generic and subgeneric formulae. Preferred solvents are volatile, non-toxic, and/or acceptable for administration to humans. The present invention provides solvates of the compounds disclosed herein.

"Stereoisomer" or "stereoisomers" refer to compounds that differ in the chirality of one or more stereocenters. Stereoisomers include enantiomers and diastereomers. The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of *Advanced Organic Chemistry*, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Pharmaceutically acceptable salt" refers to pharmaceutically acceptable salts derived from a variety of organic and inorganic counter ions well known in the art and includes, by way of example only, sodium, potassium, calcium, magnesium, ammonium, and tetraalkylammonium. When the molecule contains a basic functionality, acid addition salts of organic or inorganic acids, such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, oxalic acid, 4-toluenesulfonic acid, camphorsulfonic acid, methanesulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Salts can also be formed when an acidic proton present in the parent compound is either replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like. Pharmaceutically acceptable salts are suitable for administration in a patient and possess desirable pharmacological properties. Suitable salts further include those described in P. Heinrich Stahl, Camille G. Wermuth (Eds.), *Handbook of Pharmaceutical Salts Properties, Selection, and Use;* 2002.

The term "alkyl," as used herein unless otherwise defined, refers to a straight, branched, or cyclic saturated group derived form the removal of a hydrogen atom from an alkane. Representative straight chain alkyl groups include -methyl, -ethyl, -n-propyl, -n-butyl, -n-pentyl, and n-heptyl. Representative branched alkyl groups include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl. Representative cyclic alkyl groups include cyclohexyl, cyclopentyl, and cyclopropyl.

As used herein, and unless otherwise specified, the term "heteroalkyl" refers to a stable straight or branched chain consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O and N can be placed at any interior position of the heteroalkyl group. In one embodiment, the heteroatom(s) S and Si can be placed at any position of the heteroalkyl group (e.g., interior or terminal position), including the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms can be consecutive, such as, for example, —$CH_2$—NH—O—$CH_3$ and —$CH_2$—O—Si($CH_3$)$_3$. In certain embodiments, the heteroalkyl is optionally substituted as described herein elsewhere. In some embodiments, the heteroalkyl is optionally substituted with one or more halo.

The term "alkenyl" refers to a straight, branched, or cyclic hydrocarbon group containing at least one double bond. Representative alkenyl groups include, but are not limited to, ethylene, propylene, 1-butylene, 2-butylene, isobutylene, sec-butylene, 1-pentene, 2-pentene, isopentene, 1-hexene, 2-hexene, 3-hexene and isohexene.

The term "alkynyl" refers to a straight or branched chain hydrocarbon containing at least one triple bond. Representative alkynyl groups include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne and isohexyne.

The term "hydrocarbyl," as used herein unless otherwise defined, refers to a substituent derived from the removal of hydrogen atom from a hydrocarbon molecule. Non-limiting examples of hydrocarbyl include alkyl, alkenyl, alkynyl; cyclic groups consisting of hydrogen and carbon such as aryl as described herein, including both aromatic and non-aromatic groups as described herein; and aralkyl described herein.

The term "aryl" as used herein unless otherwise defined, refers to an aromatic group. Non-limiting examples of aryl include phenyl, naphthyl, pyridyl, phenanthryl, anthryl, furanyl, azolyl, imidazolyl, and indolyl. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless specified otherwise, the aryl is unsubstituted.

The term "heteroaryl" as used herein unless otherwise defined, refers to an aromatic group, wherein the aromatic group contains at least one ring atom that is not carbon. Non-limiting examples of heteroaryl include pyridyl, furanyl, azolyl, imidazolyl, thiophenyl, and indolyl. In one embodiment, the aryl group is substituted with one or more of the following groups: -halo, —O— ($C_1$-$C_6$alkyl), —CN, —COOR', —OC(O)R, —N(R')$_2$, —NHC(O)R' or —C(O)NHR' groups wherein each R' is independently —H or unsubstituted —$C_1$-$C_6$ alkyl. Unless specified otherwise, the heteroaryl is unsubstituted.

The term "aralkyl" as used herein unless otherwise defined, refers to an alkyl group, which is substituted with an aryl group. Non-limiting examples of an aralkyl group include benzyl, picolyl, naphthylmethyl.

The term "heterocyclyl" as used herein unless otherwise defined, refers to a cyclic group, wherein the cyclic group contains at least one ring atom that is not carbon. Representative examples heterocyclyl group include, but are not limited to, furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless specified otherwise, the heterocyclyl is unsubstituted.

The term "alkoxy," as used herein unless otherwise defined, refers to —O-(alkyl), wherein alkyl is as defined above. Representative examples of a $C_1$-$C_6$ alkoxy include, but are not limited to, —OCH$_3$, —OCH$_2$CH$_3$, —OCH$_2$CH$_2$CH$_3$, —OCH(CH$_3$)CH$_3$, —OCH$_2$CH$_2$CH$_2$CH$_3$, —OCH$_2$CH(CH$_3$)CH$_3$, —OCH(CH$_3$)CH$_2$CH$_3$, —OC(CH$_3$)$_3$, —OCH$_2$CH$_2$CH$_2$CH$_2$CH$_3$, —OCH$_2$CH(CH$_3$)CH$_2$CH$_3$, —OCH$_2$CH$_2$CH$_2$CH$_2$CH$_2$CH$_3$, and —OCH$_2$CH$_2$CH(CH$_3$)CH$_2$CH$_3$.

The terms "halo" and "halogen," as used herein unless otherwise defined, refers to —F, —Cl, —Br or —I.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

Turning next to the compositions of the invention, the term "pharmaceutically acceptable carrier or excipient" means a carrier or excipient that is useful in preparing a pharmaceutical composition that is generally safe, and possesses acceptable toxicities. Acceptable carriers or excipients include those that are acceptable for veterinary use as well as human pharmaceutical use. A "pharmaceutically acceptable carrier or excipient" as used in the specification and claims includes both one and more than one such carrier or excipient.

With reference to the methods of the present invention, the following terms are used with the noted meanings:

The terms "treating" or "treatment" of a disease includes inhibiting the disease, i.e., arresting or reducing the development of the disease or its clinical symptoms, or relieving the disease, i.e., causing regression of the disease or its clinical symptoms.

A preferred embodiment of the invention is treatment of a disease that consists of relieving the disease.

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

The term "an effective amount" or "an amount sufficient to" means the amount of the compound that will elicit the biological or medical response of a tissue, system, animal or human that is being sought by the researcher, veterinarian, medical doctor or other clinician. "An effective amount" or "an amount sufficient to" includes the amount of a compound that, when administered to a mammal for treating a disease, is sufficient to effect such treatment for the disease. The amount will vary depending on the compound, the disease and its severity and the age, weight, etc., of the subject to be treated.

The term "about" when used in connection with a referenced numeric indication means the referenced numeric indication plus or minus up to 10% of that referenced numeric indication. For example, the language "about 50" covers the range of 45 to 55.

In some embodiments, the method of the present invention relates to screening a compound for modulating activity at a TNF-like weak inducer of apoptosis (TWEAK) binding site on a cysteine-rich domain (CRD) of fibroblast growth factor-inducible 14 (Fn14), the method comprising:
a) generating a protein-protein docking model of TWEAK binding to the CRD of Fn14 wherein Y176 of SEQ ID NO: 1 is an anchoring residue;
b) matching the compound to a pharmacophoric site corresponding to Y176 of SEQ ID NO: 1 in the protein-protein docking model;
c) matching the compound to an additional pharmacophoric site in the protein-protein docking model;
d) determining that the compound has modulating activity if the compound matches the pharmacophoric site corresponding to Y176 of SEQ ID NO: 1 and the compound matches the additional pharmacophoric site.

SEQ ID NO: 1 shown below is the amino acid sequence of TWEAK in humans and corresponds with GenBank Accession Number AAC51923.1. The anchoring residue Y176 is identified with a box.

```
maarrsqrrr grrgepgtal lvplalglgl alaclgllla vvslgsrasl    50 saqepaqeel vaeedqdpse lnpqteesqd papflnrlvr prrsapkgrk   100 trarraiaah yevhprpgqd gaqagvdgtv sgweearins ssplrynrqi   150 gefivtragl yylycqvhfd eqkav[Y]lkld llvdgvlalr cleefsataa   200 sslgpqlrlc qvsgllalrp gsslrirtlp wahlkaapfl tyfglfqvh    249
```

SEQ ID NO: 2 shown below is the amino acid sequence for Fn14 in humans and corresponds with GenBank Accession Number AAF69108.1.

```
margslrrll rllvlglwla llrsvageqa pgtapcsrgs    50
swsadldkcm dcascrarph sdfclgcaaa ppapfrllwp ilggalsltf   100
vlgllsgflv wrrcrrrekf ttpieetgge gcpavaliq              129
```

In certain embodiments, the protein-protein docking model is Y176 Model 1 and/or Y176 Model 2 shown in Table 2. The screened compound may have modulating activity if the compound matches the pharmacophoric sites corresponding to Y176 and at least one, at least two, at least three, at least four, at least five, at least six, at least seven, at least eight, at least nine, or at least ten additional pharmacophoric sites.

In some implementations, the present invention is directed to a method of screening a compound for modulating activity at a TWEAK binding site on a CRD of Fn14, the method comprising:

a) generating a nuclear magnetic resonance (NMR) model of Fn14;

b) analyzing docking of the compound in flexible conformations to the NMR model, wherein analyzing docking comprises performing a docking algorithm selected from a high-throughput virtual screening (HTVS) algorithm of Glide, a standard precision (SP) algorithm of Glide, an extra precision (XP) algorithm of Glide, and combinations thereof; and c) determining that the compound has modulating activity if the docking algorithm calculates a high score for the compound.

Analyzing docking may comprise:

i) performing the HTVS algorithm of Glide on the library of compounds and calculating an HTVS score for the compounds;

ii) performing the SP algorithm of Glide on about 50% of the compounds from step i) with the highest HTVS scores and calculating an SP score for the compounds; and iii) performing the XP algorithm of Glide on about 10% of the compounds from step ii) with the highest SP scores and calculating an XP score for the compounds, thereby identifying the compounds with the greatest modulating activity.

In certain aspects, the methods of the present invention utilize the computational tools of Glide. Glide offers the full range of speed vs. accuracy options, from the HTVS (high-throughput virtual screening) mode for efficiently enriching million compound libraries, to the SP (standard precision) mode for reliably docking tens to hundreds of thousands of ligand with high accuracy, to the XP (extra precision) mode where further elimination of false positives is accomplished by more extensive sampling and advanced scoring, resulting in even higher enrichment. Glide also provides a rational workflow for virtual screening from HTVS to SP to XP, enriching the data at every level such that only an order of magnitude fewer compounds need to be studied at the next higher accuracy level. In addition, Glide reliably finds the correct binding modes for a large set of test cases. It outperforms other docking programs in achieving lower RMS deviations from native co-crystallized structures. Glide also exhibits excellent docking accuracy and high enrichment across a diverse range of receptor types.

The Glide algorithms and methods (Suite 2011: Glide, version 5.7, Schrödinger, LLC, New York, N.Y., 2011; Suite 2012: Glide, version 5.8, Schrödinger, LLC, New York, N.Y., 2012) are described in:

Friesner, R. A.; Murphy, R. B.; Repasky, M. P.; Frye, L. L.; Greenwood, J. R.; Halgren, T. A.; Sanschagrin, P. C.; Mainz, D. T., "Extra Precision Glide: Docking and Scoring Incorporating a Model of Hydrophobic Enclosure for Protein-Ligand Complexes," J. Med. Chem., 2006, 49, 6177-6196;

Halgren, T. A.; Murphy, R. B.; Friesner, R. A.; Beard, H. S.; Frye, L. L.; Pollard, W. T.; Banks, J. L., "Glide: A New Approach for Rapid, Accurate Docking and Scoring. 2. Enrichment Factors in Database Screening," J. Med. Chem., 2004, 47, 1750-1759; and Friesner, R. A.; Banks, J. L.; Murphy, R. B.; Halgren, T. A.; Klicic, J. J.; Mainz, D. T.; Repasky, M. P.; Knoll, E. H.; Shaw, D. E.; Shelley, M.; Perry, J. K.; Francis, P.; Shenkin, P. S., "Glide: A New Approach for Rapid, Accurate Docking and Scoring. 1. Method and Assessment of Docking Accuracy," J. Med. Chem., 2004, 47, 1739-1749.

In certain implementations, the disclosed methods comprise calculating a Glide score using a high-throughput virtual screening (HTVS) algorithm of Glide, a standard precision (SP) algorithm of Glide, and/or an extra precision (XP) algorithm of Glide. In some embodiments, a high HTVS, SP, or XP Glide score is less than $-1.0$, $-1.1$, $-1.2$, $-1.3$, $-1.4$, $-1.5$, $-1.6$, $-1.7$, $-1.8$, $-1.9$, $-2.0$, $-2.1$, $-2.2$, $-2.3$, $-2.4$, $-2.5$, $-2.6$, $-2.7$, $-2.8$, $-2.9$, $-3.0$, $-3.1$, $-3.2$, $-3.3$, $-3.4$, $-3.5$, $-3.6$, $-3.7$, $-3.8$, $-3.9$, $-4.0$, $-4.1$, $-4.2$, $-4.3$, $-4.4$, $-4.5$, $-4.6$, $-4.7$, $-4.8$, $-4.9$, $-5.0$, $-5.1$, $-5.2$, $-5.3$, $-5.4$, $-5.5$, $-5.6$, $-5.7$, $-5.8$, $-5.9$, $-6.0$, $-6.1$, $-6.2$, $-6.3$, $-6.4$, $-6.5$, $-6.6$, $-6.7$, $-6.8$, $-6.9$, $-7.0$, $-7.1$, $-7.2$, $-7.3$, $-7.4$, $-7.5$, $-7.6$, $-7.7$, $-7.8$, $-7.9$, $-8.0$, $-8.1$, $-8.2$, $-8.3$, $-8.4$, $-8.5$, $-8.6$, $-8.7$, $-8.8$, $-8.9$, $-9.0$, $-9.1$, $-9.2$, $-9.3$, $-9.4$, $-9.5$, $-9.6$, $-9.7$, $-9.8$, $-9.9$, or $-10.0$.

In certain embodiments, an HTVS score, an SP score, and an XP score are calculated for compounds within a library. In some embodiments, an SP score is calculated for the about 10%, about 20%, about 30%, about 40%, about 50%, about 60%, about 70%, about 80%, or about 90%, highest scoring compounds from the HTVS algorithm. In some embodiments, an XP score is calculated for the about 10%, about 20%, about 30%, about 40%, about 50%, about 60%, about 70%, about 80%, or about 90%, highest scoring compounds from the SP algorithm.

In some embodiments, energy-optimized pharmacophores (e-pharmacophores) are obtained by mapping the energetic terms from the Glide XP scoring function onto atom centers. The ligand is docked with Glide XP and the pose is refined. The Glide XP scoring terms are computed, and the energies are mapped onto atoms. Next, pharmacophore sites are generated, and the Glide XP energies from the atoms that comprise each pharmacophore site are summed. The sites are then ranked based on these energies, and the most favorable sites are selected for the pharmacophore hypothesis. These pharmacophores are then used as queries for virtual screening.

Pharmacophore sites may be automatically generated from the protein-ligand docked complex with Phase (Phase, v.3.0, Schrodinger, LLC) using the default set of six chemical features: hydrogen bond acceptor (A), hydrogen bond donor (D), hydrophobe (H), negative ionizable (N), positive ionizable (P), and aromatic ring (R). Phase treats most cationic groups as being exclusively positive ionizable. Hydrogen-bond acceptor sites may be represented as vectors along the hydrogen bond axis in accordance with the hybridization of the acceptor atom. Hydrogen-bond donors may be represented as projected points, located at the corresponding hydrogen-bond acceptor positions in the binding site. Projected points allow the possibility of structurally dissimilar active compounds forming hydrogen bonds to the same location, regardless of their point of origin and directionality.

In certain embodiments, each pharmacophore feature site is first assigned an energetic value equal to the sum of the Glide XP contributions of the atoms comprising the site. This allows sites to be quantified and ranked on the basis of these energetic terms. Glide XP descriptors include terms for hydrophobic enclosure, hydrophobically packed correlated hydrogen bonds, electrostatic rewards, $\pi$-$\pi$ stacking, $\pi$ . . . cation, and other interactions. In some embodiments, sites where less than half of the heavy atoms contribute to the pharmacophore feature are excluded from the final hypothesis. Thus, if only two heavy atoms in a six-membered ring exhibit energetic interactions, the ring may not be considered a pharmacophore feature. The Glide algorithms and their application in virtual screening of compounds are explained in greater detail in Shen et al. (2013) Mol Biosyst 9:1511-1521; Singh et al. (2012) J Mol Model 18:39-51; and Tamilvanan et al. (2013) Bioinformation 9(6):286-292.

Figure 17:
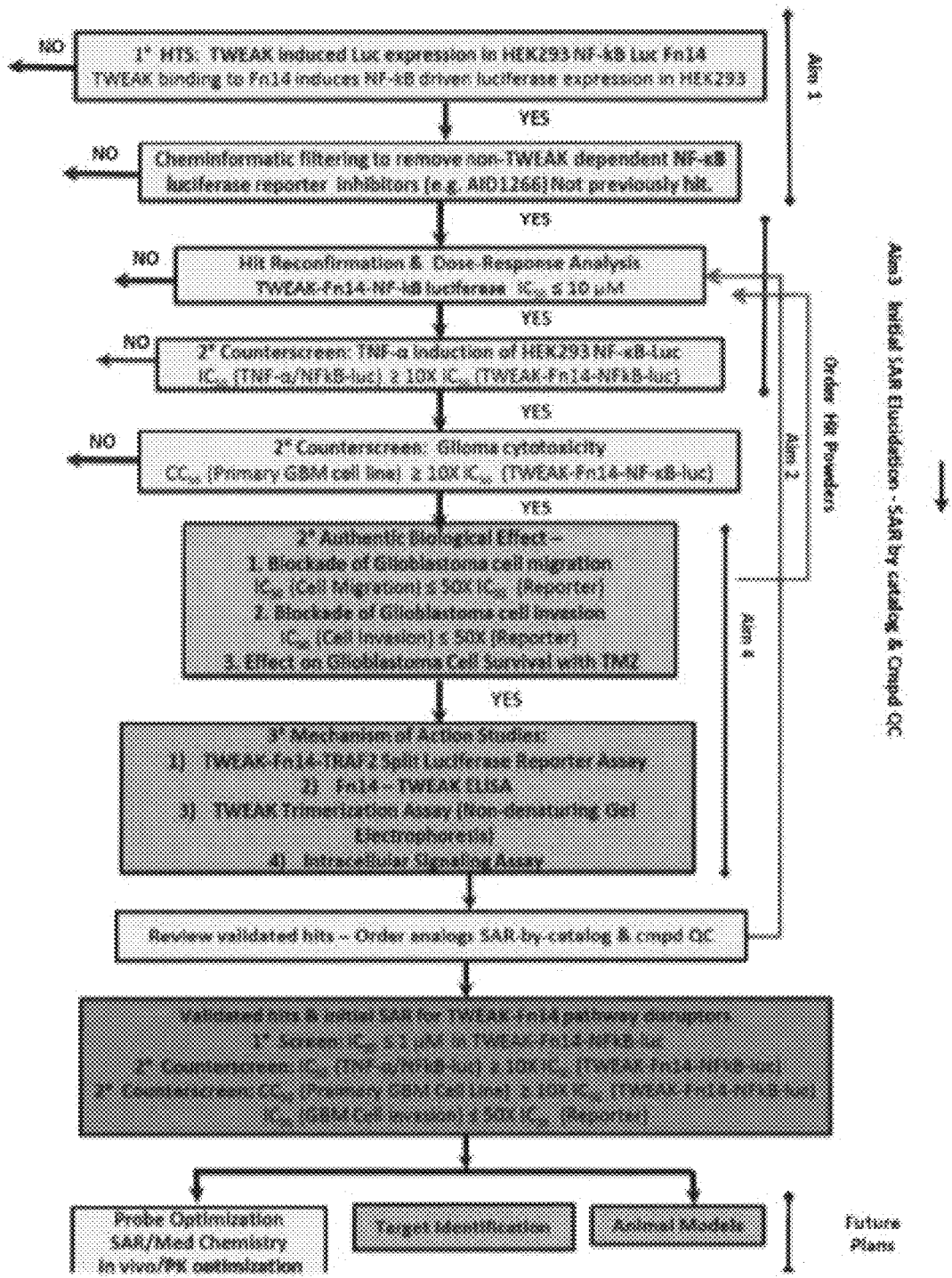
FIG. 17 depicts a process flowchart that includes processes conducted to elucidate the structural basis and targeting of the TWEAK-Fn14 interaction.

Referring to FIG. 17, some embodiments of the invention may include one or more additional processes. For example, some embodiments may include a first process, a second process, a third process, and/or a fourth process. The first process may comprise a cell-based reporter assay and high-throughput screening of one or more compounds to determine/validate modulating activity of the one or more compounds on TWEAK-Fn14 signaling. The second process may comprise a counter-screen assay that can be configured to further determine/validate the modulating activity of the one or more compounds on TWEAK-Fn14 signaling. In some aspects, the second process may also comprise an analysis of the potential cytotoxicity of the one or more compounds such that compounds that induce potentially cytotoxic effects can be determined. The third process may comprise one or more assays to elucidate the mechanisms of action of any compounds that have been validated using the first and second processes. The assays used in the third process may comprise in vitro assays. In some embodiments, the fourth process may comprise additional assays (e.g., biological assays) to further refine and/or elucidate the mechanisms of action of some or all of the compounds that have been validated using the first and second processes.

In some embodiments, the first process may comprise a cell-based nuclear factor kappa-light-chain-enhancer of activated B cells (NF-κB) luciferase reporter assay, wherein inhibition of luciferase signal following addition of the one or more compounds and purified TWEAK to NF-κB luciferase cells validates the modulating activity of the compound at the TWEAK binding site on the CRD of Fn14. In some aspects, compounds that exhibit modulating activity of the TWEAK-Fn14 interaction can be further tested using the other processes.

In some embodiments, the second process may comprise a cell-based NF-κB luciferase reporter assay. For example, the second process may include validation of the modulating activity at the TWEAK binding site on the CRD of Fn14 of the one or more compounds. In some embodiments, compounds that may exhibit an $IC_{50}$ of about less than or equal to 10 µM can be selected for further testing. In other embodiments, the $IC_{50}$ values can be any other values, such as 1 µM, 5 µM, 15 µM, 25 µM, etc.

Moreover, in some embodiments, the second process may also include a counterscreen to confirm the modulating activity at the TWEAK binding site on the CRD of Fn14 of the one or more compounds that have been validated using the prior methods or processes. For example, the lack of inhibition of luciferase signal following addition of the one or more compounds and purified tumor necrosis factor alpha (TNFα) to NF-κB luciferase cells can confirm specificity of the modulating activity at the TWEAK binding site on the CRD of Fn14. In some embodiments, compounds that exhibit an $IC_{50}$ in these counterscreening assays of about greater than or equal to 10 times the $IC_{50}$ from the validation assays described above can be selected for further testing.

In addition, the second process may further comprise a counterscreen to assess whether the modulating activity at the TWEAK binding site on the CRD of Fn14 of the one or more compounds is not correlated with non-specific global cytotoxicity. For example, some or all of the compounds that exhibit a $CC_{50}$ of about 10 times less than the $IC_{50}$ on reporter cells can be removed from additional testing.

In some embodiments, the third process may comprise one or more assays to elucidate the structure-activity relationship of the one or more compounds that are substantially or completely validated and/or confirmed by the first and second processes. For example, the third process may comprise an analysis of the scaffold class of the compounds to provide an assessment of chemical tractability and probability of success in biological systems of modulating activity of TWEAK binding site on the CRD of Fn14. In addition, the third process may also include using the scaffold class of the compounds to potentially identify more potent and selective compounds than the compounds that were initially identified using some embodiments of the invention.

In some embodiments, the fourth process may comprise assays that can be used to further assess the activity of the compounds identified by the disclosed methods and processes by measuring inhibition of migration of glioma cells resulting from addition of the one or more compounds and purified TWEAK to the glioma cells, wherein inhibition of migration of the glioma cells validates the modulating activity of the compounds at the TWEAK binding site on the CRD of Fn14. The fourth process may also comprise additional assays (e.g., enzyme-linked immunosorbent assays) to further confirm modulating activity and/or mechanism of action of the compounds.

In certain embodiments, the disorder that can be treated, prevented, or ameliorated is cancer or a proliferative disorder, including but not limited to, breast cancer (e.g., triple negative breast cancer, ER+ breast cancer, or ER− breast cancer), basal cell carcinoma, skin cancer, lung cancer, small cell lung cancer, non-small cell lung cancer, brain cancer, medulloblastoma, glioma (including glioblastoma, oligodendroglioma, astrocytoma, ependymoma), neuroblastoma, colorectal cancer, ovarian cancer, liver cancer, pancreatic cancer (e.g., carcinoma, angiosarcoma, adenosarcoma), gastric cancer, gastroesophageal junction cancer, prostate cancer, cervical cancer, bladder cancer, head and neck cancer, lymphoma (e.g., mantle cell lymphoma, diffuse large B-cell lymphoma), solid tumors that cannot be removed by surgery, locally advanced solid tumors, metastatic solid tumors, leukemia (e.g., acute myeloid leukemia (AML), acute lymphoblastic leukemia (ALL), or chronic myeloid leukemia (CML)), or recurrent or refractory tumors. In one embodiment, the disorder that can be treated, prevented, or ameliorated includes, but is not limited to, basal cell nevus syndrome (Gorlin syndrome). In one embodiment, the disorder that can be treated, prevented, or ameliorated includes, but is not limited to, basal cell carcinoma associated with Gorlin syndrome.

In one embodiment, the disorders, diseases, or conditions treatable with a compound provided herein, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain aspects, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, non-secretory myeloma, osteosclerotic myeloma, plasma cell leukemia, solitary plasmacytoma, and extramedullary plasmacytoma; (6) Waldenstrom's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, head and neck cancer, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

Particular embodiments provide treating a subject having cancer using one or more of the methods provided herein, together with surgery. Particular embodiments provide treating a subject having cancer using one or more of the methods provided herein, together with chemotherapy. Particular embodiments provide treating a subject having cancer using one or more of the methods provided herein, together with immunotherapy. Particular embodiments provide treating a subject having cancer using one or more of the methods provided herein, together with targeted therapy. Particular embodiments provide treating a subject having cancer using one or more of the methods provided herein, together with radiation therapy. Particular embodiments provide treating a subject having cancer using one or more of the methods provided herein, together with two or more of the treatments selected from surgery, chemotherapy, immunotherapy, targeted therapy, and radiation therapy.

In certain embodiments, the subject to be treated with one of the methods provided herein has not been treated with anticancer therapy prior to the administration of a compound provided herein. In certain embodiments, the subject to be treated with one of the methods provided herein has been treated with one or more anticancer therapies prior to the administration of a compound provided herein. In certain embodiments, the subject to be treated with one of the methods provided herein has been treated with a cancer therapeutic agent, as described herein. In certain embodiments, the subject to be treated with one of the methods provided herein has developed drug resistance to anticancer therapy. In certain embodiments, the subject to be treated with the methods provided herein has a relapsed cancer. In certain embodiments, the subject to be treated with the methods provided herein has a refractory cancer. In certain embodiments, the subject to be treated with the methods provided herein has a metastatic cancer.

In other embodiments, the disease state to be treated, prevented, or ameliorated is an Fn14-mediated condition. The present disclosure encompasses the use of an Fn14-binding compound or composition described herein to treat any Fn14-mediated condition. Exemplary conditions include cancer, metastasis, excessive vascularization or angiogenesis, an autoimmune disease, an inflammatory disease, a neurodegenerative disease, keloid scarring, graft versus host disease, graft rejection or ischemia.

In one embodiment, the Fn14-mediated condition is an inflammatory disease or an autoimmune disease. In one example, the condition is a connective tissue disease (including inflammatory arthritis, such as rheumatoid arthritis, psoriatic arthritis, reactive arthritis or gout), lupus (including systemic lupus erythematosus), type 1 diabetes, multiple sclerosis, vasculitis (including Wegener's granulomatosis and Henoch Schonlein Syndrome), nephritis (including glomerulonephritis and pneumonitis), atherosclerosis or inflammation of the eye (including uveitis).

In another embodiment, the autoimmune condition is multiple sclerosis, neuritis, polymyositis, psoriasis, vitiligo, Sjogren's syndrome, arthritis (such as rheumatoid arthritis), Type 1 diabetes, autoimmune pancreatitis, inflammatory bowel diseases, Crohn's disease, ulcerative colitis, celiac disease, glomerulonephritis, scleroderma, sarcoidosis, autoimmune thyroid diseases, Hashimoto's thyroiditis, Graves disease, myasthenia gravis, Addison's disease, autoimmune uveoretinitis, pemphigus vulgaris, primary biliary cirrhosis, pernicious anemia, or systemic lupus erythematosis (SLE). In one aspect, the condition is rheumatoid arthritis or SLE.

In another aspect, the condition is a connective tissue disease, such as rheumatoid arthritis. In this regard, Dharmapatni et al., Arthritis Res Ther, 13: R51, 2011 have shown that Tweak/Fn14 play a role in rheumatoid arthritis.

In one embodiment, the condition is scleroderma (including systemic scleroderma).

In another embodiment, the condition is graft rejection (e.g., allograft rejection) or graft versus host disease (including weight loss associated with graft versus host disease). In this regard, Tweak/Fn14 have been show to play a role in pathogenesis of graft versus host disease, e.g., by Zhao et al., J Immunol, 179: 7949-7958, 2007.

In another embodiment, the condition is cardiac allograft vasculopathy.

In one aspect, the condition is graft rejection associated intimal thickening.

In another aspect the condition is intramyocardial infarction or ischemic reperfusion injury. In this regard, Tweak/Fn14 has been shown to play a role in ischemia by, e.g., Frauenknecht et al., J Neuroimmunol, 227: 1-9, 2010 and Inta et al., J Neurol Sci 275: 117-120, 2008.

In another aspect, the condition is associated with excessive angiogenesis and/or neovascularization, e.g., cancer (including solid tumors, leukemias, lymphoma, melanoma, glioma, breast cancer, colonic cancer, gastric cancer, esophageal cancer, renal cell cancer, ovarian cancer, cervical cancer, carcinoid cancer, testicular cancer, prostate cancer, head and neck cancer and hepatocellular carcinoma), cancer metastasis, cancer neovascularization, autoimmune disease (including psoriasis), nephropathy, retinopathy, preeclampsia, hepatitis, sepsis and macular degeneration.

In one aspect, the condition is cancer or a metastasis thereof. The term "cancer" refers to or describes the physiological condition in mammals that is typically characterized by unregulated cell growth/proliferation. Examples of cancer include, but are not limited to, an adenocarcinoma, a squamous cell carcinoma, a digestive/gastrointestinal cancer, an endocrine cancer, an eye cancer, a musculoskeletal cancer, a breast cancer, a neurologic cancer, a genitourinary cancer, a germ cell cancer, a head and neck cancer, a hematologic/blood cancer, a respiratory cancer, a skin cancer, an AIDS-related malignancy or a gynelogic cancer.

An adenocarcinoma is a cancer of an epithelium that originates in glandular tissue. Exemplary adenocarcinomas include forms of colorectal cancer, lung cancer, cervical cancer, prostate cancer, urachus cancer, vulval cancer, breast cancer, esophageal cancer, pancreatic cancer and gastric cancer.

Digestive/gastrointestinal cancers include anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including childhood hepatocellular (liver) cancer; pancreatic cancer including childhood pancreatic cancer; sarcoma, rhabdomyosarcoma; rectal cancer; and small intestine cancer.

Endocrine cancers include islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor.

Eye cancers include intraocular melanoma; and retinoblastoma.

Musculoskeletal cancers include Ewing's family of tumors; osteosarcoma/malignant fibrous histiocytoma of the bone; rhabdomyosarcoma including childhood rhabdomyosarcoma; soft tissue sarcoma including childhood soft tissue sarcoma; clear cell sarcoma of tendon sheaths; and uterine sarcoma.

Neurologic cancers include childhood brain stem glioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and supratentorial primitive neuroectodermal tumors including childhood and pituitary tumor.

Genitourinary cancers include bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor;

Germ cell cancers include childhood extracranial germ cell tumor; extragonadal germ cell tumor; ovarian germ cell tumor; and testicular cancer.

Head and neck cancers include lip and oral cavity cancer; childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer.

Hematologic/blood cell cancers include leukemia (e.g., acute lymphoblastic leukemia in adults and children; acute myeloid leukemia, e.g., in adults and children; chronic lymphocytic leukemia; chronic myelogenous leukemia; and hairy cell leukemia); a lymphoma (e.g., AIDS-related lymphoma; cutaneous T-cell lymphoma; Hodgkin's lymphoma including Hodgkin's lymphoma in adults and children; Hodgkin's lymphoma during pregnancy; non-Hodgkin's lymphoma including non-Hodgkin's lymphoma in adults and children; non-Hodgkin's lymphoma during pregnancy; mycosis fungoides; Sezary syndrome; Waldenstrom's macroglobulinemia; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders).

Respiratory cancers include non-small cell lung cancer; small cell lung cancer; malignant mesothelioma including malignant mesothelioma in adults and children; malignant thymoma; childhood thymoma; thymic carcinoma; bronchial adenomas/carcinoids including childhood bronchial adenomas/carcinoids; pleuropulmonary blastoma.

Skin cancers include Kaposi's sarcoma; Merkel cell carcinoma; melanoma; basal cell carcinoma and childhood skin cancer.

In a further aspect, the condition is a wasting disorder, such as cachexia. In one example, the wasting disorder is associated with a condition, such as, cancer, metabolic acidosis, infectious diseases, diabetes, autoimmune immune deficiency syndrome (AIDS), autoimmune disorders, addiction to drugs, cirrhosis of the liver, chronic inflammatory disorders, anorexia, chronic heart failure, chronic kidney disease, osteoporosis, skeletal muscle disease, motor neuron disease, multiple sclerosis, muscle atrophy and neurodegenerative disease.

In one aspect, the wasting disorder is cachexia or sarcopenia (e.g., wasting associated with aging). In another aspect, the wasting disorder is cachexia.

In one embodiment, the cachexia is associated with cancer, infectious disease (e.g., tuberculosis or leprosy), AIDS, autoimmune disease (including rheumatoid arthritis or type 1 diabetes), cystic fibrosis, drug addiction, alcoholism or liver cirrhosis.

In another embodiment, the cachexia is associated with an autoimmune disease. In one aspect, the cachexia is associated with rheumatoid arthritis. In another aspect, the cachexia is associated with type 1 diabetes.

In one example, the cachexia is associated with cardiac disease.

In one example, the cachexia is associated with chronic kidney disease.

In one example, the cachexia is associated with chronic pulmonary inflammation.

In one example, the cachexia is associated with instestinal inflammation.

In one example, the cachexia is associated with inflammatory bowel disease.

In one example, the cachexia is associated with aging.

In one example, the cachexia is associated with sepsis.

In one example, the cachexia is associated with AIDS.

In one exemplary form of the present disclosure the wasting disorder is cachexia associated with cancer. Exemplary cancers are described above.

In one embodiment, the method additionally comprises identifying a subject suffering from cachexia. Such a subject can be identified, for example, based on detection of unintentiaonal weight loss following diagnosis of another condition (e.g., cancer). For example, the subject can lose at least 5% of their body weight following diagnosis of another condition (e.g., cancer) or within the previous 30 days.

In some embodiments, the compositions of the present invention are suitable for treatment of immune system diseases or disorders, including, but not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendo-crinopathies, Purpura (e.g., Henloch-Scoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitus, and autoimmune inflammatory eye, autoimmune thyroiditis, hypothyroidism (i.e., Hashimoto's thyroiditis), systemic lupus erythematosus, discoid lupus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulomatous, degenerative, and atrophic disorders.

In further embodiments, the compositions of the present invention can be used to treat alloimmune diseases, for example graft rejection, or graft-versus-host or host-versus-graft disease.

In one embodiment, provided herein is a pharmaceutical composition comprising a compound of Formula (I) or Formula (II) as defined herein elsewhere, or an enantiomer, a mixture of enantiomers or a mixture of diastereomers thereof, or a pharmaceutically acceptable salt, solvate, hydrate or prodrug thereof, and at least one pharmaceutically acceptable excipient, adjuvant, carrier, buffer, or stabiliser.

In one embodiment, the pharmaceutically acceptable excipient, adjuvant, carrier, buffer, or stabiliser is non-toxic and does not interfere with the efficacy of the active ingredient. The precise nature of the carrier or other material will depend on the route of administration, which may be oral or by injection, such as cutaneous, subcutaneous, or intravenous injection.

In one embodiment, the pharmaceutical compositions are provided in a dosage form for oral administration, which comprise a compound provided herein, e.g., a compound of Formula (I) or Formula (II), or an enantiomer, a mixture of enantiomers or a mixture of diastereomers thereof, or a pharmaceutically acceptable salt, solvate, hydrate or prodrug thereof, and one or more pharmaceutically acceptable excipients or carriers. The pharmaceutical compositions provided herein that are formulated for oral administration may be in tablet, capsule, powder, or liquid form. A tablet may comprise a solid carrier or an adjuvant. Liquid pharmaceutical compositions generally comprise a liquid carrier such as water, petroleum, animal or vegetable oils, or mineral oil or synthetic oil. Physiological saline solution, dextrose or other saccharide solution, or glycols such as ethylene glycol, propylene glycol, or polyethylene glycol may be included. A capsule may comprise a solid carrier such as gelatin.

In another embodiment, the pharmaceutical compositions are provided in a dosage form for parenteral administration, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. Preservatives, stabilisers, buffers, antioxidants, and/or other additives may be included as required.

In yet another embodiment, the pharmaceutical compositions are provided in a dosage form for topical administration, which comprise a compound provided herein, and one or more pharmaceutically acceptable excipients or carriers.

In one embodiment, the pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, e.g., Remington: The Science and Practice of Pharmacy, supra; Modified-Release Drug Delivery Technology, 2nd Ed., Rathbone et al., eds., Marcel Dekker, Inc.: New York, N.Y., 2008).

In one embodiment, the pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

In one embodiment, the pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In another embodiment, the pharmaceutical compositions provided herein further comprise one or more chemotherapeutic agents as defined herein.

Chemotherapeutic agents in the general sense thereof, are compounds, which can be used for the treatment of a disease or disorder that arises from bacterial, viral or parasitic infection or that is due to transformation of normal cells (cancer). One particular indication of chemotherapy is cancer. Chemotherapeutic agents can act for example by killing cells that divide more rapidly than other cells, and thus target cancer cells which commonly divide more rapidly than non-cancerous cells. Most chemotherapeutic agents work by impairing cell division at one of several stages of the cell cycle. Thus, they are able to target those cells that divide more rapidly. Chemotherapeutic agents can be either cytostatic, i.e., they slow down or abrogate the growth or division of cells; other chemotherapeutic agents can cause damage to cells and kill them; in that case they are termed cytotoxic. Most cytotoxic drugs inflict a damage that per se does not suffice to kill a cell but that generates a stimulus to initiate programmed cell death (apoptosis).

In general, major classes of chemotherapeutic drugs are alkylating agents, anti-metabolites, anthracyclines, plant alkaloids, topoisomerase inhibitors and other anti-tumour agents. Most commonly, as mentioned above, these drugs affect one or several stages of the cell cycle; they can also affect DNA synthesis or DNA integrity. Other chemotherapeutics do not directly interfere with DNA. These are newer classes of chemotherapeutics and can include monoclonal antibodies and tyrosine kinase inhibitors lite imatinib mesylate. Other examples are chemotherapeutic hormones and hormone antagonists, e.g. glucocorticosteroids.

Examples for alkylating agents, which alkylate nucleophilic functional groups are mechtorethamine, cyclophosphamide, chlorambucil, melphalane, trofosfamide, ifosfamide, carmustine, lomustine. dacarbazine, temozolomide, mitomycine C and many others. Cisplatin, carboplatin, oxaliplatin and other platinum containing compounds form stable complexes with DNA.

Cytotoxic anti-metabolites are folic acid analogues (e.g., methotrexat/aminopterin, raltitrexed, pemetrexed), purine analogs (e.g., 6-mercaptopurine, azathioprine, thioguanine, fludarabine, cladribine) or pyrimidine analogs (cytarabine, gemcitabine, 5-fuk uracil and its prodrugs, deazacytkiine). Antimetabolites either inhibit DNA-synthesis by interfering with crucial steps in the cfe novo synthesis of purine and pyrimidine nucleotides or they become incorporated into DNA during the S-phase of the cell cycle, where they interfere with DNA-folding, DNA-repair or methylation. Alternatively, some compounds also become incorporated into RNA. Examples for alkaloids and terpenoids which are derived from plants and block cell division by preventing microtubule function are vinca-aialoids and taxanes. Particularly well known vinca-alkaloids are vincristine, vinblastine, vinorelbine and vindesine. Podophyllotoxin is an additional example of a plant-derived compound. An example for a taxane is docetaxel or paclitaxel. Another example is abraxane, an albumin bound paclitaxel. Estramustin is an example of a synthetic compound that targets tubulin.

Examples of topoisomerase inhibitors, which are inhibitors of enzymes that maintain the topology of DNA, include camphtotecines like irinotecan and topotecan (type 1 topoisomerase inhibitors) or amsacrin, etoposide, etoposide phosphate and teniposide (topoisomerase-type 2 inhibitors).

Finally, examples of antineoplastic intercalating agents include dactinomyctn, doxorubicin, epirubicin, bleomycin and others.

A comprehensive overview is comprised in Goodman and Gilman, The Pharmacological Basis of Therapeutics, 12lh Edition, "General Principles of Cancer Chemotherapy".

The following are examples for alkylating agents: Mechtorethamine, Cyclophosphamide Ifosfamide, Melphalan, Chlorambucil, Procarbazine (N-methylhydrazine, MIH), Busulfan, Camustine (BCNU), Streptozocin (streptozotocin), Bendamustine, Dacarbazine (DTIC; dimethyltriazenol midazole carboxamide), Temozolomide, Cisplatin, carboplatin, oxalplatin.

Antimetabolites are exemplary represented by Methotrexate (Amethopterin), Pemetrexed, Fluorouracil (5-fluorouracil; 5-FU), capecitabine, Cytarabine (cytosine arabinoside), Gemcitabine, 5-aza-cytidine, Deoxy-5-aza-cytidine, Mercaptoptirine (6-mercaptopurine; 6-MP), Pentostatin (2'-deoxycoformycin), Rudarabine, Clofarabine, and Nelarabine.

Natural Products can be selected from: Vinblastine, Vinorelbine, Vincristine, Paclitaxel, docetaxel, Etoposide, Teniposide, Topotecan, Irinotecan, Dactinomycin, (actinomycin D), Daunorubicin (daunomycin, rubidomycin), Doxorubicin, Yondelis, Mitoxantrone, Bleomycin, Mitomycin C, and L-Asparaginase.

Examples for Hormones and Antagonists are: Mitotane, Prednisone, Hydroxyprogesterone caproate, medroxyprogesterone acetate, megestrol acetate, Dietyhlstilbestrol, ethinyl estradiol, Tamoxifen, toremifene, Anastrozole, letrozole, exemestane, Testosterone propionate, fluoxymesterone, Flutamide, casodex, Leuprolide, while examples for further agents are: Hydroxyurea, Tretinoin, arsenic trioxide, Histone deacetylase inhibitor (vorinostat), Imatinib, Dasatinib, nilotinib, Gefrtinib, ertoinib, Sorafenib, Sunitinib, Lapatinib, Bortezomib, interferon-alpha, Interteukin-2, Thalidomide, Lenaiidomide, Temsiroiimus, and Everolimus.

It will be appreciated that therapeutic agents and pharmaceutical compositions in accordance with the present invention can be employed in combination therapies. In some embodiments, the present invention encompasses "therapeutic cocktails" comprising compositions in accordance with the invention. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose. In some embodiments, the therapies employed may achieve different effects (e.g., control of any adverse side effects) or they may achieve a synergistic effect when administered together.

Pharmaceutical compositions in accordance with the present invention may be administered either alone or in combination with one or more other therapeutic agents. By "in combination with," it is not intended to imply that the agents must be administered at the same time and/or formulated for delivery together, although these methods of delivery are within the scope of the invention. It will further be appreciated that therapeutically active agents utilized in combination may be administered together in a single composition or administered separately in different compositions. Compositions can be administered concurrently with, prior to, or subsequent to, one or more other desired therapeutics or medical procedures. In general, each agent will be administered at a dose and/or on a time schedule determined for that agent. In general, it is expected that agents utilized in combination with be utilized at levels that do not exceed the levels at which they are utilized individually. In some embodiments, the levels utilized in combination will be lower than those utilized individually. Additionally, the invention encompasses delivery of pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an agent in accordance with the invention may be administered concurrently with another therapeutic agent used to treat the same disorder), and/or they may achieve different effects (e.g., control of any adverse side effects). In some embodiments, compositions in accordance with the invention are administered with a second therapeutic agent that is approved by the U.S. Food and Drug Administration.

In some embodiments, compositions in accordance with the invention may be administered in combination with any therapeutic agent or therapeutic regimen that is useful to treat, alleviate, ameliorate, relieve, delay onset of, inhibit progression of, reduce severity of, and/or reduce incidence of one or more symptoms or features of an autoimmune disorder. For example, various agents which inhibit inflammation (e.g., steroids) can be used to treat autoimmune disorders in general. In some embodiments, compositions in accordance with the invention may be administered in combination with agents which inhibit inflammation (e.g., steroids) in order to treat autoimmune disorders.

In specific embodiments, compositions in accordance with the invention may be administered in combination with any therapeutic agent or therapeutic regimen that is useful to treat, alleviate, ameliorate, relieve, delay onset of, inhibit progression of, reduce severity of, and/or reduce incidence of one or more symptoms or features of diabetes. For example, compositions in accordance with the invention may be administered in combination with traditional diabetes therapies including, but not limited to, insulin administration.

In specific embodiments, compositions in accordance with the invention may be administered in combination with any therapeutic agent or therapeutic regimen that is useful to treat, alleviate, ameliorate, relieve, delay onset of, inhibit progression of, reduce severity of, and/or reduce incidence of one or more symptoms or features of rheumatoid arthritis. For example, compositions in accordance with the invention may be administered in combination with soluble TNF receptor, anti-TNFα receptor, analgesics, non-steroidal anti-inflammatory agents (NSAIDs), and/or other agents useful for treatment of rheumatoid arthritis.

In specific embodiments, compositions in accordance with the invention may be administered in combination with any therapeutic agent or therapeutic regimen that is useful to treat, alleviate, ameliorate, relieve, delay onset of, inhibit progression of, reduce severity of, and/or reduce incidence of one or more symptoms or features of Crohn's disease. For example, compositions in accordance with the invention may be administered in combination with anti-TNFα receptor and/or other agents useful for treatment of Crohn's disease.

In specific embodiments, compositions in accordance with the invention may be administered in combination with any therapeutic agent or therapeutic regimen that is useful to treat, alleviate, ameliorate, relieve, delay onset of, inhibit progression of, reduce severity of, and/or reduce incidence of one or more symptoms or features of multiple sclerosis. For example, compositions in accordance with the invention may be administered in combination with interferon β-1b, interferon β-1a, and/or other agents useful for treatment of multiple sclerosis.

In specific embodiments, compositions in accordance with the invention may be administered in combination with any therapeutic agent or therapeutic regimen that is useful to treat, alleviate, ameliorate, relieve, delay onset of, inhibit progression of, reduce severity of, and/or reduce incidence of one or more symptoms or features of granulomatous disease and/or osteoporosis. For example, compositions in accordance with the invention may be administered in combination with interferon β-1b and/or other agents useful for treatment of granulomatous disease and/or osteoporosis.

One of ordinary skill in the art will understand that the examples presented above are not meant to be limiting. The principles presented in the examples above can be generally applied to any combination therapies for treatment of autoimmune disease.

In yet another embodiment, provided herein is the use of compound of Formula (I) or Formula (II) or an enantiomer, a mixture of enantiomers or a mixture of diastereomers thereof, or a pharmaceutically acceptable salt, solvate, hydrate or prodrug thereof, in the manufacture of a medicament for the treatment of one or more disorders disclosed herein. In certain embodiments, the medicament is in tablet, capsule, powder, or liquid form. In certain embodiments, the medicament is formulated as described herein.

The amount of a compound of the invention that is effective in the treatment of a particular condition disclosed herein can depend on the nature of the condition, and can be determined by standard clinical techniques. In vitro or in vivo assays can be employed to help identify optimal dosage ranges. The precise dose to be employed in the compositions can also depend on the route of administration or the severity of the condition, and can be decided according to the judgment of the practitioner and each subject's circumstances. However, suitable dosage ranges for oral administration are generally about 0.001 mg to 2000 mg of a compound of the invention per kg body mass. In some embodiments, the oral dose is 0.01 mg to 100 mg per kg body mass, 0.1 mg to 50 mg per kg body mass, 0.5 mg to 20 mg per kg body mass, or 1 mg to 10 mg per kg body mass. In some embodiments, the oral dose is 5 mg of a compound of the invention per kg body mass. The dosage amounts described herein refer to total amounts administered; that is, if more than one compound of the invention is administered, the dosages can correspond to the total amount of the compounds of the invention administered. Oral compositions can comprise 10% to 95% active ingredient by mass.

In one embodiment, the pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

In one embodiment, binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pregelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

In one embodiment, suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

In one embodiment, suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

In one embodiment, suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

In one embodiment, suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

In one embodiment, the pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

In one embodiment, the tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

In one embodiment, the pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239;

and 4,410,545. The capsules may also be coated as known by those of skill in the art in order to modify or sustain dissolution of the active ingredient.

In one embodiment, the pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

In one embodiment, other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

In one embodiment, the pharmaceutical compositions provided herein for oral administration can be also provided in the forms of liposomes, micelles, microspheres, or nanosystems. Micellar dosage forms can be prepared as described in U.S. Pat. No. 6,350,458.

In one embodiment, the pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

In one embodiment, coloring and flavoring agents can be used in all of the above dosage forms.

In one embodiment, the pharmaceutical compositions provided herein for oral administration can be formulated as immediate or modified release dosage forms, including delayed-, sustained, pulsed-, controlled, targeted-, and programmed-release forms.

In one embodiment, the pharmaceutical compositions provided herein can be administered parenterally by injection, infusion, or implantation, for local or systemic administration. Parenteral administration, as used herein, include intravenous, intraarterial, intraperitoneal, intrathecal, intravenous, intraarterial, intraperitoneal, intrathecal, intraventricular, intraurethral, intrasternal, intracranial, intramuscular, intrasynovial, intravesical, and subcutaneous administration.

In one embodiment, the pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington: The Science and Practice of Pharmacy, supra).

In one embodiment, the pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

In one embodiment, suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

In one embodiment, suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In one embodiment, when the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

In one embodiment, the pharmaceutical compositions provided herein for parenteral administration can be formulated as immediate or modified release dosage forms, including delayed-, sustained, pulsed-, controlled, targeted-, and programmed-release forms.

In one embodiment, the pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

In one embodiment, suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

In one embodiment, suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In one embodiment, the pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

In one embodiment, the pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

In one embodiment, pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

In one embodiment, the pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

In one embodiment, the pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, e.g., Remington: The Science and Practice of Pharmacy, supra). These vehicles are emollient but generally require addition of antioxidants and preservatives.

In one embodiment, suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

In one embodiment, gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

In one embodiment, the pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

In one embodiment, rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfate and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

In one embodiment, the pharmaceutical compositions provided herein can be administered ophthalmically in the forms of solutions, suspensions, ointments, emulsions, gel-forming solutions, powders for solutions, gels, ocular inserts, and implants.

In one embodiment, the pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

In one embodiment, solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

In one embodiment, the pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

In one embodiment, capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1

Experimental Procedures

Consensus alignment and model building for TWEAK. The templates for homology modeling were selected from RCSB PDB database (Berman H M, Westbrook J, Feng Z, Gilliland G, Bhat T N, et al. (2000) Nucleic Acids Res 28: 235-242). Consensus alignment based on three-dimensional structure was performed in MOE to obtain a structure-derived sequence alignment (v2010.10, Chemical Computing Group Inc. 2012) ((2010) Molecular Operating Environment (MOE). Chemical Computing Group Inc., 1010 Sherbooke St. West, Suite #910, Montreal, QC, Canada, H3A 2R7). All template structures were superimposed in 3D, with an initial main-chain atom root mean square deviation (RMSD) of 2.49 Å. In the corresponding sequence alignment, a consensus set of residues was defined based on two criteria: (1) residue identity, retaining those residues with at least 50% of sequence identity per alignment column; and (2) RMSD of main-chain atoms. The former parameter was kept fixed while the latter parameter was decremented, starting at the initial value of 2.49 Å and decreasing by increments of 0.5 Å until reaching 1 Å. At each step, the structural superimposition of the proteins was refined using only the consensus residues, and the sequence alignment was subsequently refined to reflect the structural alignment changes. The resulting sequence alignment was utilized as a fixed template to align the sequence of TWEAK. Homology modeling was performed using MOE with the options of disabling C-terminal and N-terminal outgap modeling and enabling automatic disulphide bond detection. A maximum of 10 intermediate models were created. Model refinement was performed at a medium setting for both intermediate and final model. AMBER99 forcefield was used for all energy minimizations and GB/VI scoring method was used for model scoring. One final refined model was created per template.

Protein-protein docking simulations. Protein-protein docking simulations were performed using well-vetted methodologies implemented in ICM Pro v 3.7-2b, MolSoft LLC 2012 (Abagyan R, Totrov M, Kuznetsov D (1994) J Comp Chem 15: 488-506). The epitopes were selected on the basis of available biological knowledge of the interacting interfaces from April-TACI (PDB ID: 1XU1) and April-BCMA (PDB ID: 1XU2) complexes, and knowledge from Fn14 residues required for binding, as established by Winkles and coworkers (Brown S A, Hanscom H N, Vu H, Brew S A, Winkles J A (2006) Biochem J 397: 297-304). For the receptor protein, pre-calculated grid maps were generated involving van der Waals, electrostatic and desolvation terms using ECEPP/3 molecular mechanics force field (Nemethy G, Gibson K D, Palmer K A, Yoon C N, Paterlini G, et al. (1992) J Phys Chem 96: 6472-6484). For the ligand protein, several starting conformations were sampled and optimized using a pseudo-Brownian Monte-Carlo based method, followed by local energy minimizations (Abagyan R, Totrov M, Kuznetsov D (1994) J Comp Chem 15: 488-506). All the conformations accumulated were merged into a single conformational set compressed by comparison of the atomic coordinates and removal of geometrically similar conformations. The resulting conformations were further optimized by allowing flexibility of the ligand side-chains. The interaction energy function uses the internal energy of the ligand and intermolecular energy based on the optimized potential maps. The multiple levels of optimization performed in this approach reduce the possibility of being trapped in local minima. A single docking run was performed for each receptor-ligand complex and 30-40 poses were obtained for each individual docking run.

Virtual Library Preparation. The peptidomimetic set of ChemDiv (version of May 2011; 13,137 compounds) was prepared using LigPrep version 2.5 in Schrodinger v2011 (Schrodinger LLC, New York) by adding hydrogen atoms and calculating protonation states corresponding to pH of 7.4. This resulted in generation of 21,682 structures. A conformational search was performed using ConfGen Standard search (default parameters), with ConfGen version 2.3 in Schrodinger (Schrodinger LLC, New York) (Watts K S, Dalal P, Murphy R B, Sherman W, Friesner R A, et al. (2010) J Chem Inf Model 50: 534-546), generating a database of 145,995 conformations.

Pharmacophore-Based Virtual Screening. Receptor-based pharmacophore generation was performed using Phase version 3.4 implemented in Maestro 9.3 of Schrodinger suite v2011 (Schrodinger LLC, New York) (Dixon S L, Smondyrev A M, Rao S N (2006) Chem Biol Drug Des 67: 370-372). The ligand was defined as the ensemble of TWEAK residues involved in inter-molecular interactions with Fn14. The pharmacophore features were then identified exhaustively for these contacting residues. The features that were not located at the direct protein-protein interaction interface were manually removed. Excluded volumes were included to capture the Fn14 receptor geometry when preparing the pharmacophore model; these were calculated using a scaling factor of 0.9. The conformational ligand database was interrogated for hits matching the generated pharmacophore hypothesis. Pharmacophoric points involving the TWEAK anchoring residue were required and matching of other pharmacophoric points was set as optional.

Structure-Based Virtual Screening. The protein preparation workflow of Maestro 9.3 (Schrodinger LLC v2011, New York) was employed to prepare the Fn14 receptor by adding missing H atoms and refining the structure using default parameters. A grid-enclosing box was centered at the centroid of the three binding site residues involved in TWEAK binding as indicated by mutation data from Winkles, i.e., Asp45, Lys48, Asp62 (Brown S A, Hanscom H N, Vu H, Brew S A, Winkles J A (2006) Biochem J 397: 297-304). Structure-based virtual screening was performed with the conformational ligand database, and the ligands were kept flexible during the docking stage. A three-step docking process was executed: (1) a first parsing was performed by docking of compounds with the fastest HTVS algorithm of Glide (Schrodinger LLC, New York, v2011) (Friesner R A, Banks J L, Murphy R B, Halgren T A, Klicic J J, et al. (2004) J Med Chem 47: 1739-1749), and scoring of compounds. (2) The top 50% of the virtual hits from step 1 were docked using the standard precision algorithm of Glide and were subsequently scored. (3) Lastly, 10% of the top scoring compounds of step 2 were re-docked using XP algorithm, scored, and considered as hits.

Cell culture. The human astrocytoma cell line T98G and human HEK293 cells (American Type Culture Collection) were maintained in DMEM (Gibco, USA) supplemented with 10% heat-inactivated fetal bovine serum (FBS; Gibco, USA) at 37° C. with 5% CO2. For assays involving TWEAK treatment, cells were cultured in reduced serum (0.5% FBS) for 16 hr prior to TWEAK stimulation.

Expression constructs. The coding sequence for the soluble form of TWEAK, designated sTWEAK, encoding amino acids K97-H249 was amplified by polymerase chain reaction and ligated in-frame either downstream of a 3×FLAG epitope in p3XFLAG-CMV (Sigma, St. Louis, Mo.) or upstream of a 3×HA epitope in pcDNA3 (Invitrogen, Carlsbad, Calif.). The sTWEAK Y176D, Y176A, Y176F, and W231G variants were generated using the Quickchange II site-directed mutagenesis kit (Stratagene, La Jolla, Calif.). All substitutions were verified by DNA sequence analysis. Expression constructs for in vitro transcription were generated using Gateway Technology (Invitrogen). First, coding sequences for sTWEAK and sTWEAK variants were amplified by polymerase chain reaction with oligonucleotide primers containing the appropriate aatB recombination sequences and the aatB flanked PCR products transferred to the entry vector pDONR221. Resulting pDONR clones were transferred to the T7 based in vitro transcription expression vector pANT7 (Ramachandran N, Hainsworth E, Bhullar B, Eisenstein S, Rosen B, et al. (2004) Science 305: 86-90). All proteins were expressed as epitope tagged proteins.

Synthesis of sTWEAK and Mutant sTWEAK proteins. sTWEAK and sTWEAK variant proteins were synthesized using a 1-step coupled human in vitro transcription/translation (IVTT) kit (Pierce Biochemicals) or a 1-step coupled rabbit in vitro transcription/translation (IVTT) kit (Promega) according to the manufacturer's instructions.

Double Sandwich ELISA. sTWEAK and sTWEAK variant proteins were synthesized as described above. The expression level of each IVTT synthesized sTWEAK protein was analyzed by western blot analysis and used in approximately equal amounts in the ELISA. To assay the binding of wild type sTWEAK and sTWEAK variants to Fn14, the human Fc fragment-tagged Fn14 extracellular domain (R&D Systems) was captured in an Immuno 96-microwell white plate by adding 100 μL of 0.025 μg/mL Fn14-Fc to wells coated with goat anti-human Fcγ fragment specific monoclonal antibody. After capture, the wells were washed 3× with Dulbecco's Phosphate Buffered Saline (DPBS) containing 0.05% Tween-20. Unbound sites were blocked by addition of 100 μL of blocking solution containing 0.05% Tween-20, 1% BSA, and 3% normal goat serum (NGS) in DPBS for 1 hr at room temperature. 0.01 μL of sTWEAK or sTWEAK variant made with the human IVTT kit or 2 μL of sTWEAK or sTWEAK variant made with the rabbit IVTT kit was diluted in 100 μL of sample diluent (DPBS+1% BSA+0.005% Tween-20) and then added to the wells for 2 hr followed by addition of 100 μL of 50 ng/mL biotinylated TWEAK detection antibody (R&D Systems) in sample diluent. Following incubation for additional 2 hr at room temperature, wells were washed 3× with DPBS containing 0.05% Tween-20 and bound biotinylated TWEAK antibody was detected by incubation with an HRP-conjugated streptavidin. The total luminescent signal was obtained using Femto ELISA kit (Pierce Biochemical) and compared to the standard curve signal obtained from the binding of 0-4000 pg/mL recombinant TWEAK (Peprotech inc) to Fn14-Fc. Using 5-parameter logistic curve fitting for standard curve analysis (Sigmaplot 11.0, SyStat Software Inc.), binding of sTWEAK or TWEAK variant to Fn14-Fc was determined. The data represents that observed for at least four replicate assays.

The small molecule screening was performed using the ELISA assay described above with minor modifications. Briefly, after capturing Fn14-Fc in the microwell plate, 80 μl of drug solution in sample diluent was added to desired wells and incubated for 2 hrs at room temperature. Subsequently, 20 µL of 2500 pg/mL (5×) TWEAK was added to each well to achieve final TWEAK concentration of 500 pg/mL and incubated for additional 2 hr at room temperature. Bound TWEAK was detected as described in the protocol above. All small molecule inhibitors were screened at 25 µM final concentration (final DMSO concentration of 0.125%) in duplicate. Cyclohexamide, a non-specific small molecule, at 25 µM concentration was used as negative control. The anti-Fn14 antibody ITEM-4, added at 2.5 µg/mL, was used as a positive control for complete blockade of TWEAK binding. Reduction in TWEAK binding due to compound addition or controls was calculated by using standard curve (Separate standard curve was obtained for every screening plate).

Non-Denaturing/Native Gel Electrophoresis. Native gel electrophoresis kit and reagents were purchased from Invitrogen and electrophoresis and western blotting was performed according to the manufacturer's protocol. Briefly, IVTT protein lysates (1 µL) were mixed with 1 µL of 10% n-dodecyl-β-D-maltoside (DDM), 0.5 µl of 5% NativeP-AGE™ G-250 additive, 2.5 µL of 4× NativePAGE™ Sample Buffer (4×), and deionized water to make the total volume to 10 µL. Electrophoresis was performed for 2 hr at 16 mA at room temperature using NativePAGE™ Novex® 4-16% Bis-Tris Gels. Calibration was achieved by separation of Native-Mark™ protein standards of known molecular masses. After gel electrophoresis, proteins were transferred to PVDF membrane for immunoblotting with an anti-FLAG antibody (Sigma, St. Louis, Mo.).

NF-κB luciferase reporter Assay. The capacity of sTWEAK or sTWEAK variants to activate Fn14 signaling was evaluated using engineered reporter cell lines that express luciferase upon NF-κB activation. Two reporter cell lines were utilized for these experiments. HEK293 NF-κB luciferase (courtesy of Dr. Jeff Winkles) were generated by transfecting HEK293 cells with a reporter plasmid containing 5 copies of a consensus NF-κB binding site upstream of a minimal CMV promoter driving expression of firefly luciferase. The second cell line, designated HEK293 NF-κB luciferase Fn14 FL, was generated by stably transfecting the HEK293 NF-κB luciferase cell line with full length Fn14. To assay the binding of sTWEAK or sTWEAK variants to Fn14, reporter cells were seeded in tissue culture treated white 96-well plates at 1×104 cells/well in 80 µL Opti-MEM media (Invitrogen) and incubated for 48 hr at 37° C. After 48 hr incubation, 20 µL of 5× purified recombinant TWEAK (Peprotech Inc.; 150 ng/mL) in 1 mg/mL BSA in PBS was added to each well and incubated for 5 hr at 37° C. as positive control. Similarly, equivalent amounts of sTWEAK or sTWEAK variant prepared via IVTTas determined using ELISA assay described above was added in 20 µl. IVTT solution lacking a cDNA template in 1 mg/mL BSA in PBS and 1 mg/mL BSA in PBS alone was used as an additional control. At the end of 5 hr incubation, the luminescent signal was determined using Bright-Glo assay kit (Promega, Madison, Wis.) according to the manufacturer's instructions.

Small molecules that demonstrated ≥15% inhibition of TWEAK binding to Fn14 in the ELISA screen were validated using the cell based NF-κB luciferase reporter assay with minor modifications. Briefly, Fn14-NF-κB-Luc reporter cells, (Fn14 overexpressing HEK293 NF-κB luciferase cells), were seeded in tissue culture treated white 96-well plates at 1×104 cells/well in 80 µL Opti-MEM media (Invitrogen) and incubated for 48 hr at 37° C. After 48 hr incubation, 10 µL of the drug solution (200 µM) in DMSO was added to the designated wells at a final concentration of 20 µM. After 1 hr of drug incubation at 37° C., 10 µL of 10× purified recombinant TWEAK (Peprotech Inc.; 300 ng/mL) in 1 mg/mL BSA in PBS was added to each well and incubated for 5 hr at 37° C. DMSO alone was used as a negative control whereas anti-TWEAK antibody suspended in DMSO was used as a positive control for the assay. Luminescent signal was determined using Bright-Glo assay kit (Promega, Madison, Wis.) according to the manufacturer's instructions and normalized to negative control. A counter-screen assay was carried out using TNFα to stimulate NF-κB activity in NF-κB-Luc reporter cells (HEK293 NF-κB luciferase cells). The counter-screen assay was performed similar to the drug screening assay described above, except 10 µL of 10× purified recombinant TNFα (R&D Scientific; 300 ng/mL) in 1 mg/mL BSA in PBS was added to each well instead of TWEAK for NF-κB activation. Small molecules, that showed inhibition of the luciferase signal following TWEAK stimulation but not after TNFα stimulation, were further validated by performing a dose response analysis. The selected small molecule inhibitor was tested at concentrations ranging from 0.75 µM to 250 µM for its ability to suppress TWEAK induced NF-κB activity in Fn14 overexpressing HEK293 NF-κB luciferase cells compared to its ability to suppress TNFα induced NF-κB activity in HEK293 NF-κB luciferase cells. IC50 values for dose response curve were determined using the curve fitting functionality of GraphPad Prism software.

Cell Migration Assay. The effect of pharmacological inhibition of TWEAK/Fn14 signaling on glioma cell migration was analyzed using a modified Boyden chamber (Neuroprobe, Cabin John, Md.) as described previously (Lamszus, K., et al. (1998) Journal international du cancer 75, 19-28; Brockmann, M. A., et al. (2003) Neurosurgery 52, 1391-1399). Each well contains a 8-1 µm pore size Nucleopore filter that had been coated with 50 µg/mL PureCol® (Bovine Collagen) (Advanced Biomatrix, Poway, Calif.). T98G glioma cells were treated with selected drug compound for 1 hr and then seeded at 4.8×104 cells in 100 µL of DMEM with 0.1% bovine serum assay medium to the top well of the chamber. TWEAK was added to the lower wells of the chamber using DMEM with 0.1% bovine serum albumin as assay medium. After incubation for 5 hours at 37° C., nonmigrated cells were scraped off the upper side of the filter, and filters were stained with 4',6-diamidino-2-phenylindole (DAPI). Nuclei of migrated cells were counted in 5 high-power fields (HPF) with a 20× objective. Values were assessed in triplicate.

Cytotoxicity Assay. Cytotoxic effects of drugs on glioma cells were analyzed by quantifying the ATP, an indicator of metabolically active cells. Briefly, glioma cells were seeded in tissue culture treated white 96-well plates at $3 \times 10^3$ cells/well in 80 µL Opti-MEM media (Invitrogen) and incubated for 24 hr at 37° C. After 24 hr incubation, 20 µL of 5× drug solution at required concentration in Opti-MEM was added to each well and incubated for 72 hr at 37° C. Opti-MEM/DMSO mixture without drug was used as negative control and 20 µM staurosporine was used as positive control. At the end of 72 hr incubation, the number of viable cells were quantified by using CellTiter-Glo assay kit (Promega, Madison, Wis.) according to the manufacturer's instructions. Luminescence signal measured was normalized to negative control to determine % cell viability.

Surface Plasmon Resonance (SPR) Assay. The binding affinity of at least one of the compounds (e.g., L524-0366) to TWEAK and Fn14-Fx was determined using a BIAcore T100 optical biosensor (GE Healthcare) at 25 degrees Celsius at the Arizona Proteomics Consortium. Recombinant human TWEAK (20 µg/mL in 10 mM HEPES pH 7.4, 150 mM NaCl, 3 mM EDTA, 0.05% Tween 20) or recombinant human Fn14-Fc (20 µg/mL in 10 mM NaOAc pH 4.0) were covalently coupled to separate flow cells on a BIAcore CM5 sensor chip using standard amine coupling chemistry as per manufacturer's protocol. Final immobilization levels were 6000 Response Units (RU) for TWEAK and 13,000 RU for FN14-Fc. The first flow path of the chip was treated with the same coupling and blocking reagents without protein and was used as a reference for each binding cycle. Functionality of the TWEAK and the Fn14-Fc sensor surfaces were verified by injecting Fn14-Fc and TWEAK over them respectively. Serial dilutions of L524-0366 or cycloheximide (control) from 0 to 50 µM were made in running buffer (10 mM HEPES pH 7.4, 150 mM NaCl, 3 mM EDTA, 1% DMSO). The compounds were injected over the TWEAK and Fn14-Fc sensor surfaces for 60 seconds at a flow rate of 45 µL/minute. Running buffer was injected for 5 minutes at a flow rate of 45 µL/minute to dissociate bound compound molecules from the sensor surface. The fluidics were washed with 50% DMSO after each sample injection and to minimize sample carry-over, a buffer wash step was included after each binding cycle. A DMSO calibration curve was used to correct for any bulk responses due to mismatches between sample and running buffer (Frostell-Karlsson, A. et al. (2000) Journal of Medicinal Chemistry 75, 19-28). Equilibrium dissociation constants for the small molecules were calculated by fitting the double reference subtracted data to $Req=((CRmax)/(K_D+C))+RI$, where RI is the bulk refractive index contribution.

Example 2

Fn14 Receptor Selection

An NMR structure of the Fn14 CRD is available in PDB (PDB ID: 2RPJ) (He F, Dang W, Saito K, Watanabe S, Kobayashi N, et al. (2009) Protein Sci 18: 650-656). All 20 models captured in the structure were visually inspected to assess areas of structural flexibility in the putative receptor binding site. This revealed a highly conserved core region (A34-A69) with very few flexible side-chains. This rigid core includes the residues D45, K48, and D62 previously identified as required for TWEAK binding by Winkles et al. and delineating the protein-protein binding interface (Brown S A, Hanscom H N, Vu H, Brew S A, Winkles J A (2006) Biochem J 397: 297-304). Importantly the side chain of R58, located in close proximity of the putative protein-protein interface, presents a high degree of flexibility. We therefore hypothesized that R58 could potentially act as a switch that opens the binding groove. Models 1 and 17 respectively capture a closed and an open geometry as illustrated in FIG. 1. In model 17, the side-chain of R58 points toward the solvent which reveals a potential binding site on the surface of the Fn14 CRD. Conversely, in model 1, the side chain of R58 obscures that potential binding site. Both extreme configurations of the receptor were considered for further protein-protein docking, with the understanding that the open configuration captured in model 17 is likely to be more favorable than the closed configuration captured in model 1. Thus, we compared 20 NMR models of Fn14 for side chain flexibility, two of which were selected for further consideration.

Example 3

Homology Modeling of TWEAK

Figure 2A:
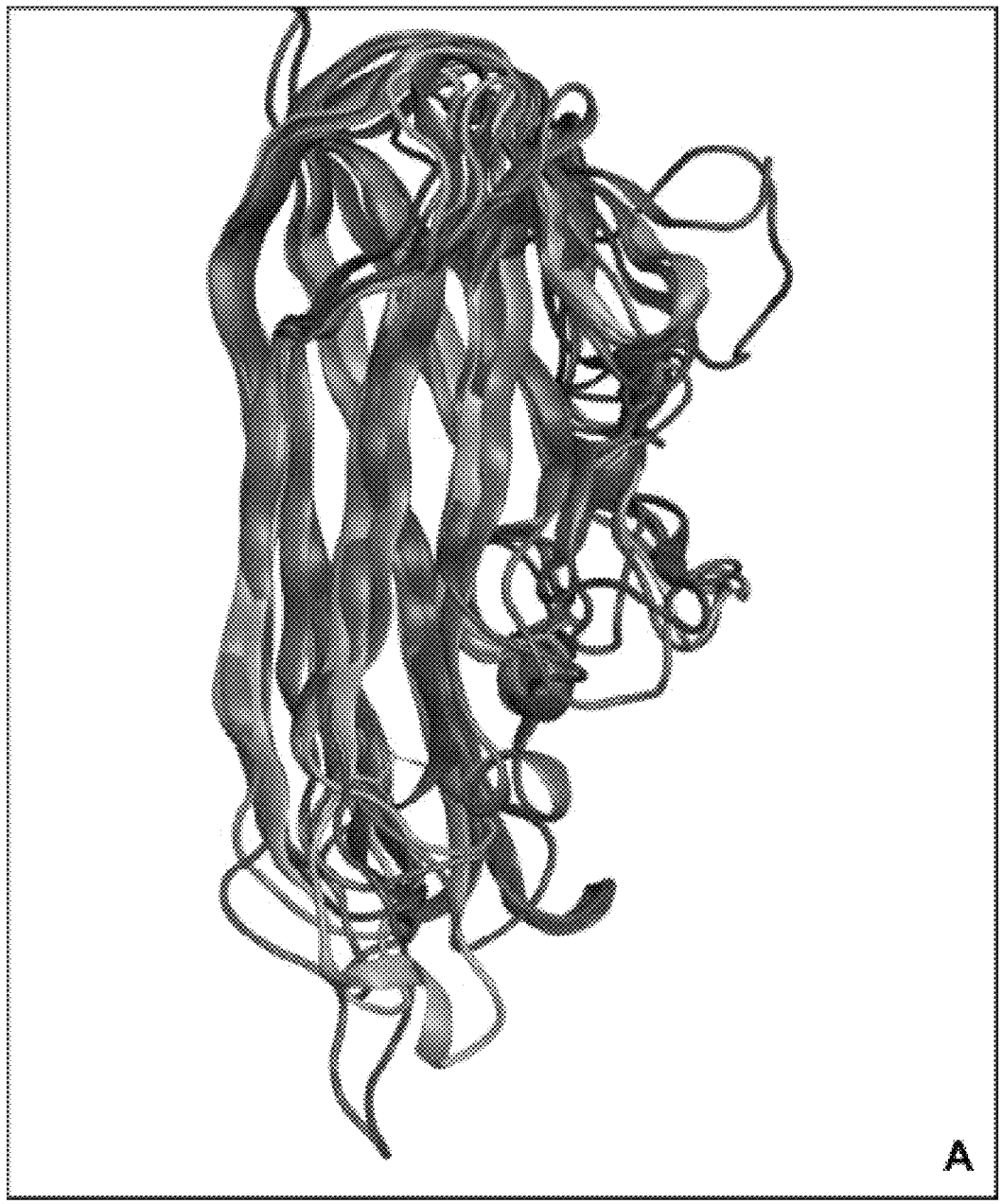
FIG. 2A, Consensus structural alignment performed in MOE (Chemical Computing Group) for six members of TNF superfamily.

Homology modeling of TWEAK was undertaken in the absence of an experimental crystal structure. The C-terminal extracellular domain of TWEAK was predicted to have a β-pleated sheet structure based on structures of other members of TNF superfamily (Banner D W, D'Arcy A, Janes W, Gentz R, Schoenfeld H J, et al. (1993) Cell 73: 431-445). Several other members of TNF superfamily are characterized by experimental structures in PDB but the low sequence identity with TWEAK limits their selection as a direct template for homology modeling. We overcame this limitation by using consensus-based structural overlay of the template structures available to derive a quality multiple sequence alignment, and by employing this alignment for building homology models (FIG. 2). The advantage of preferring structural alignment over sequence alignment is due to the fact that structural conservation predominates sequence conservation and is closer to function (Chothia C, Lesk AM (1986) EMBO J 5: 823-826). Six members of TNF superfamily associated with an experimental structure were used as template structures. These include TNF ligand superfamily member 11 (PDB ID: 1S55), TNF beta (PDB ID: 1TNR), TNF ligand superfamily member 13 (PDB ID: 1XU2), TNFα (PDB ID: 2E7A), TNF superfamily ligand TL1A (PDB ID: 2RJL) and TNF ligand superfamily member 9 (PDB ID: 2X29). Since the residue identity of TWEAK with these templates is very low (12.8-17.9%) (Table 1), we first obtained a structure-derived sequence alignment of the six template proteins, which was then used to align the sequence of TWEAK. TWEAK sequence aligned onto that of each individual template protein was considered the starting point of an extensive homology modeling campaign, ultimately leading to six TWEAK homology models as described in the method section.

TABLE 1

Similarity matrix of the percentages of sequence identity for the six templates structures (identified by their PDB ID) and TWEAK, based on the structure-derived sequence alignment generated by structural consensus in MOE.

| Protein | TWEAK | 1S55 | 1TNR | 1XU2 | 2E7A | 2RJL | 2X29 |
|---|---|---|---|---|---|---|---|
| TWEAK |  | 16.7 | 19.4 | 15.3 | 18.0 | 14.2 | 16.7 |
| 1S55 | 16.7 |  | 22.7 | 16.8 | 22.0 | 28.4 | 17.9 |
| 1TNR | 17.9 | 21.2 |  | 21.9 | 32.0 | 32.6 | 14.7 |
| 1XU2 | 13.5 | 14.7 | 20.8 |  | 22.7 | 17.0 | 10.9 |
| 2E7A | 17.3 | 21.2 | 33.3 | 24.8 |  | 29.1 | 13.5 |
| 2RJL | 12.8 | 25.6 | 31.9 | 17.5 | 27.3 |  | 15.4 |
| 2X29 | 16.7 | 17.9 | 16.0 | 12.4 | 14.0 | 17.0 |  |

Example 4

TWEAK-Fn14 Binding Mode Prediction Via Protein-Protein Docking

Prior to docking of the TWEAK protein to the Fn14 CRD, benchmarking was performed to parameterize the algorithms and verify the predictive ability of the ICM-Pro algorithms for TNFR and their ligands. For that purpose, we used the crystal structure of the April-BCMA complex (PDB ID: 1XU2) (Hymowitz S G, Patel D R, Wallweber H J, Runyon S, Yan M, et al. (2005) J Biol Chem 280: 7218-7227) as a model system. In a first step, the ligand (BCMA) was translated away from the complex and rotated, but the conformation was unchanged. The ICM-Pro protein-protein docking algorithm identified multiple poses, with the lowest energy solution corresponding to the geometry of the crystal structure. In a second step, the ligand was moved away from the binding site and the side-chains of the interfacing residues were randomized to evaluate the ability to identify a complex in the ensemble of solutions that approaches the experimental complex. We found that the 7th best solution rank-ordered by interaction energy was consistent with the actual binding mode. In light of these outcomes, we concluded that the ICM-Pro algorithm, as parameterized, was suitable to identify plausible poses of TNF ligands bound to their receptors in an ensemble of low energy solutions.

Figure 3:
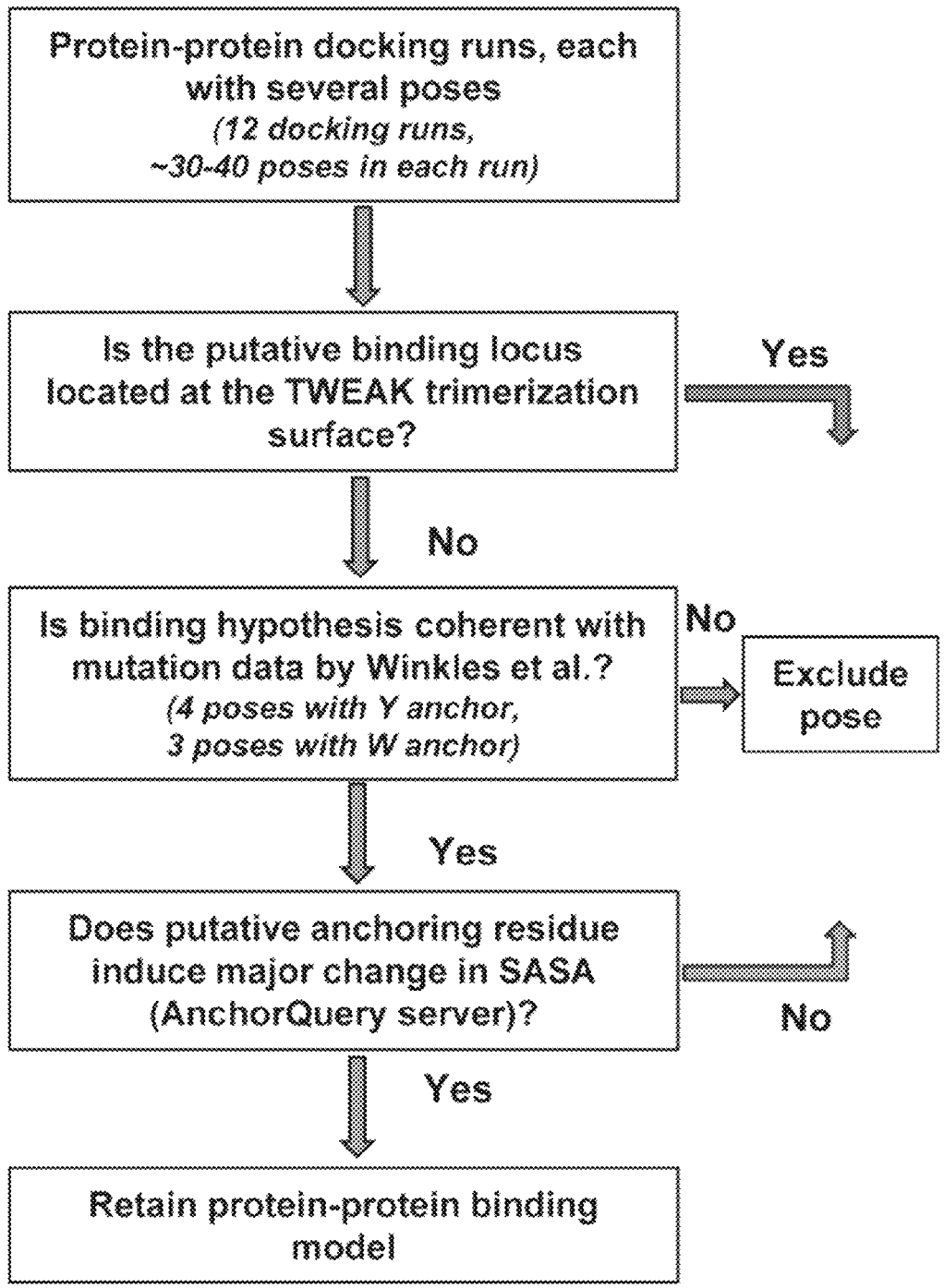
FIG. 3 depicts data-driven decision-making workflow for prioritization of protein-protein docking results. Protein-protein docking of six TWEAK models was performed with two Fn14 models, leading to 12 protein-protein docking runs and hundreds of poses. Poses where the putative binding locus is located at the TWEAK trimerization interface were not considered as valid. Poses with the mutational validated residues D45, K48, M50 and D62 present at the binding interface were retained. Finally, Anchor Query server was used to rank-order the anchoring residues and those models with Phe, Tyr, or Trp resulting in SASA loss upon complex formation were retained.
Figure 4:
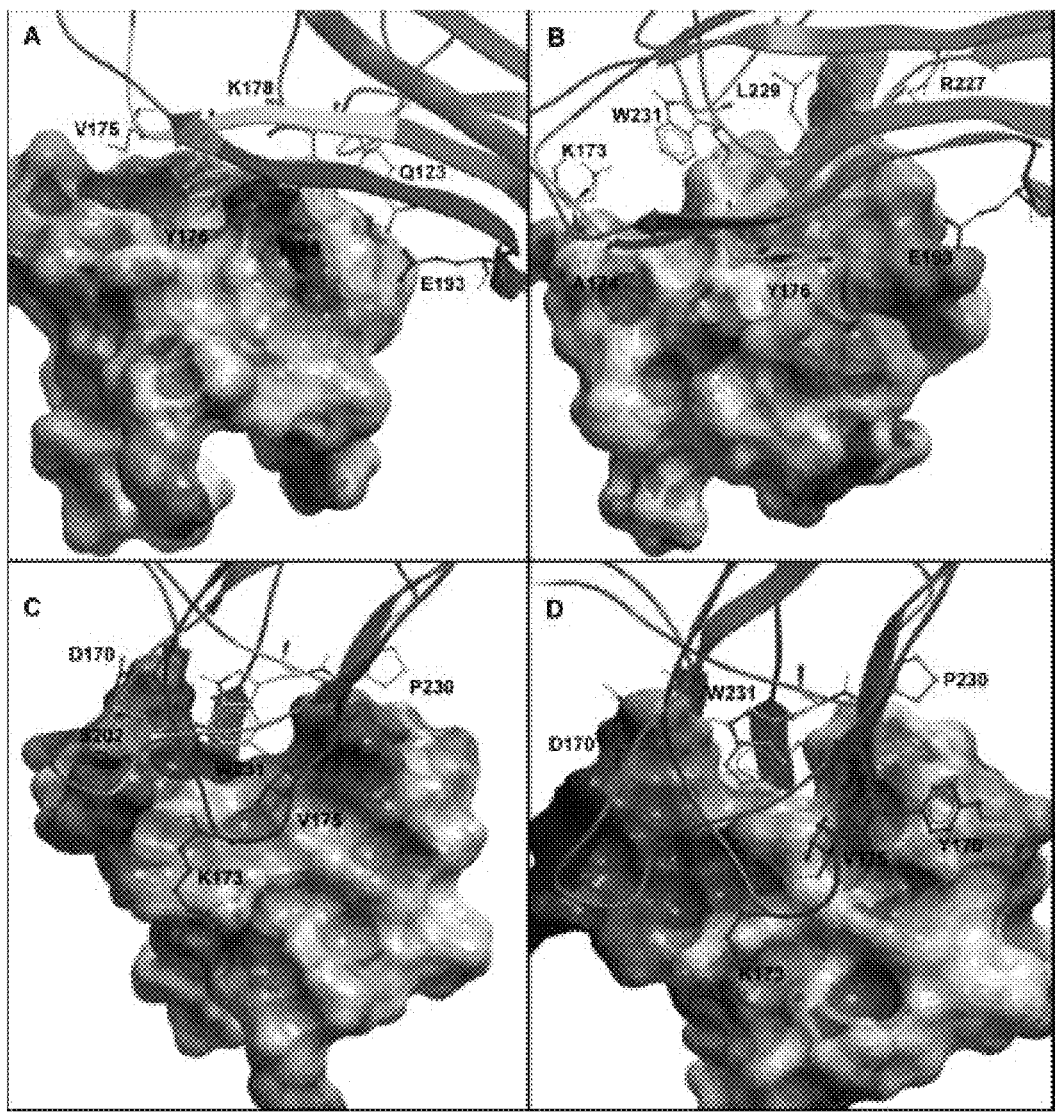
FIG. 4 depicts prioritized binding models for Fn14-TWEAK. 4A, 4B, 3D representations of the two TWEAK-Fn14 prioritized models with TWEAK Y176 serving as an anchor residue to bind Fn14 CRD. 4C, 4D, 3D representations of the two prioritized models with TWEAK W231 serving as an anchor to bind Fn14 CRD. A van der Waals surface is overlaid on the Fn14 CRD in all panels.

On that basis, protein-protein docking calculations were performed for two Fn14 structures (vide supra) and six TWEAK homology models in order to predict TWEAK-Fn14 binding modes. A total of twelve protein-protein docking simulations were performed, producing hundreds of poses. Initial binding epitopes required to start the protein-protein docking calculation were defined by similarity to the known interacting interfaces from April-TACI and April-BCMA complexes. Each simulation generated between 30 and 40 ligand-receptor poses. TWEAK-Fn14 candidate solutions were analyzed and prioritized following a data-driven decision-making process as summarized in FIG. 3: (1) Poses with the predicted TWEAK anchoring residue lying at the putative TWEAK trimerization interface were excluded; (2) Poses coherent with mutation data by Winkles et al. (Brown S A, Hanscom H N, Vu H, Brew S A, Winkles J A (2006) Biochem J 397: 297-304) were retained; (3) Candidate solutions with the TWEAK predicted anchoring residue being Phe, Trp, or Tyr were prioritized as they have been reported to be some of the most frequently observed anchoring residues in protein-protein interactions (Bogan A A, Thorn K S (1998) J Mol Biol 280:1-9). Following this process, a total of 4 models with Tyr anchor and 3 models with Trp anchor were identified from all protein-protein docking runs; (4) The remaining candidate complexes were individually examined using the internet-based webserver Anchor Query (Meireles L M, Domling A S, Camacho C J (2010) Nucleic Acids Res 38: W407-411) to further analyze the anatomies of the predicted protein-protein interaction interfaces. The program leverages the concept of amino acid residues as anchors that bury a large amount of solvent accessible surface area at the protein-protein interface, and calculates changes in solvent accessible surface area (SASA) upon binding of each side chain at the interface. This information is utilized to rank the residues, with the top ranking ones being likely the anchoring residue of the interaction based on SASA loss upon complex formation. We retained those solutions for which the anchoring residues identified in step 3 ranked first in this methodology. In summary, this process identified four models with two putative TWEAK residues anchoring the ligand to Fn14 CRD, i.e., Y176 and W231 (FIG. 4).

Example 5

Experimental Confirmation of Binding by TWEAK Mutagenesis

Figure 5:
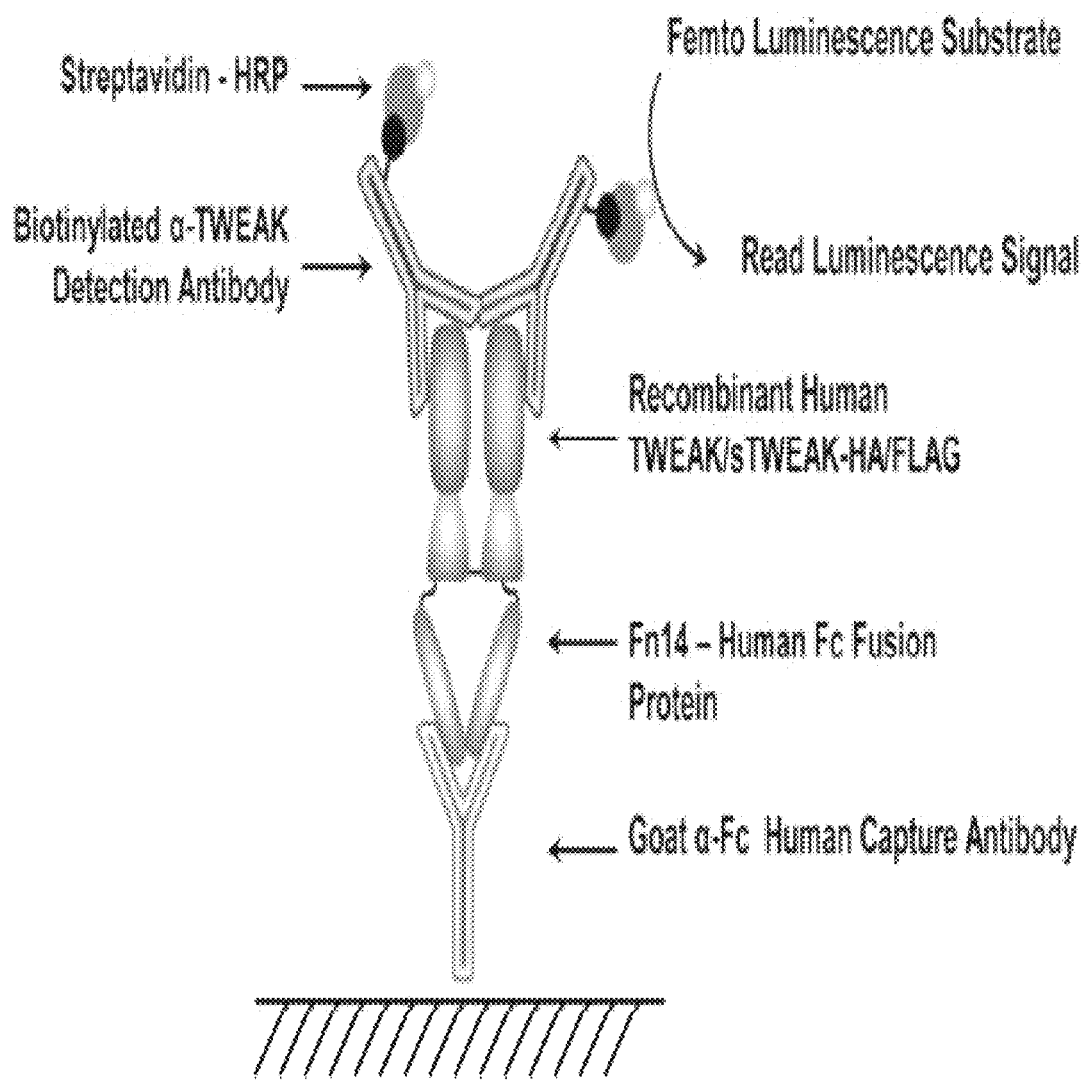
FIG. 5 depicts schematic of the double sandwich ELISA assay. Fn14-Fc fusion protein was captured using anti-Fc antibody. Recombinant TWEAK or sTWEAK variants prepared using IVTT were bound to captured Fn14 and detected using biotinylated anti-TWEAK antibody.
Figure 6:
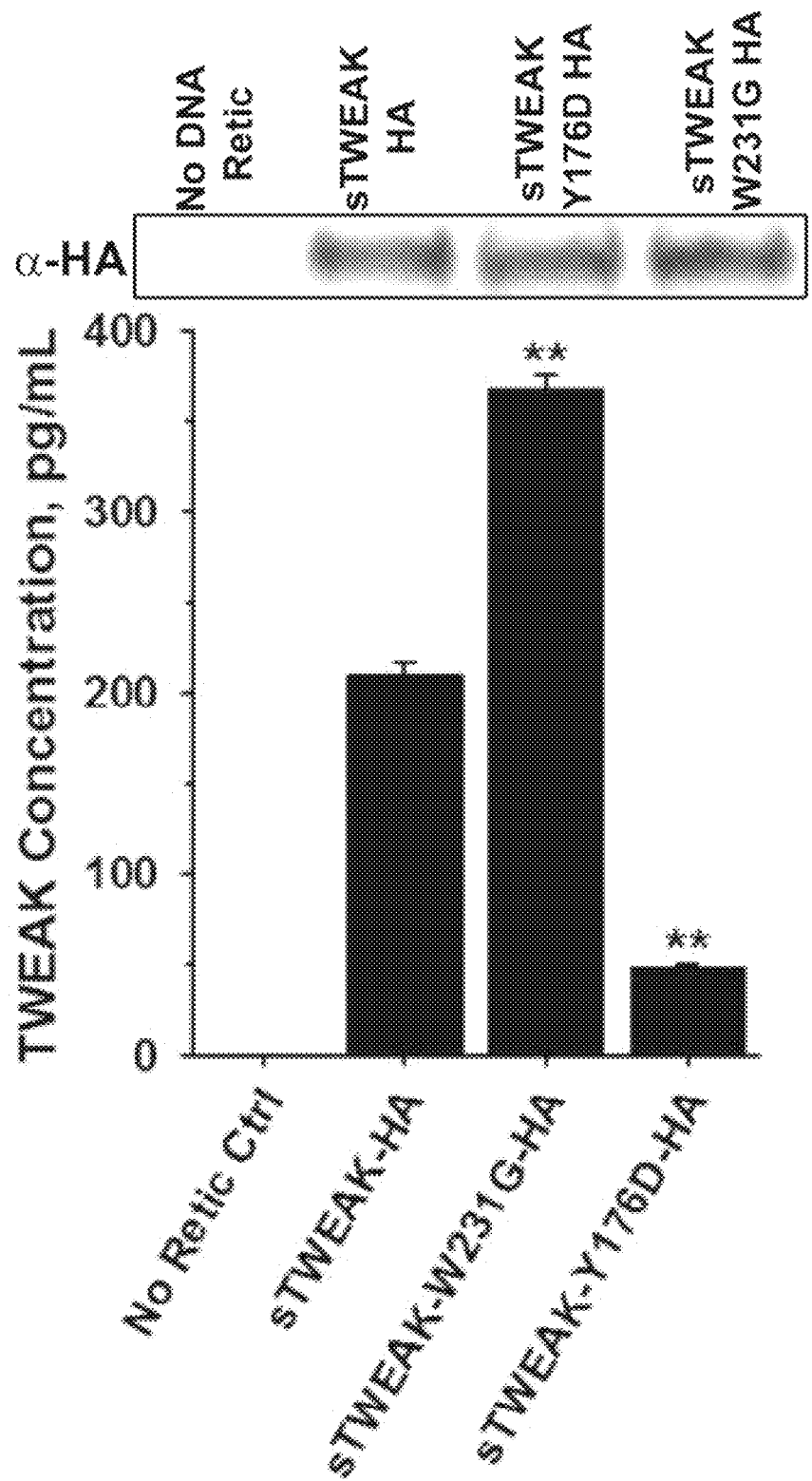
FIG. 6 depicts substitution of TWEAK Y176 disrupts the Fn14-TWEAK interaction. 6A, Immunoblot analysis using anti-HA antibody showing equal expression of sTWEAK, sTWEAK Y176D, or sTWEAK W231G in IVTT lysates. No DNA; IVTT without added cDNA template. 6B, Double-sandwich ELISA showing binding of sTWEAK, or indicated sTWEAK variants to Fn14 (**, $p<0.001$; *, $p<0.01$). Concentrations of sTWEAK and sTWEAK variants were determined using standard curve obtained with recombinant TWEAK.

Binding mode prediction via protein-protein docking indicated TWEAK Y176 or W231 as plausible anchoring amino acid residues mediating the TWEAK-Fn14 interaction. To experimentally validate models generated from protein-protein docking calculation and to determine which predicted residue is critical for TWEAK binding to the Fn14, we performed a double sandwich ELISA to analyze the binding of sTWEAK and sTWEAK variants to Fn14. A schematic of the ELISA is shown in FIG. 5. Failure of any sTWEAK variant to bind to Fn14 would be indicated by reduction in the chemiluminescent signal. Immunoblot analysis using anti-HA antibody indicated that sTWEAK HA, sTWEAK Y176D HA, and sTWEAK W231G HA were synthesized equivalently using the rabbit IVTT system and were used for the ELISA (FIG. 6A). In the ELISA, substitution amino acid Y176 significantly reduced TWEAK binding to Fn14 while substitution of amino acid W231 significantly increased the TWEAK binding to the Fn14. Together these results suggest that Y176 is a critical amino acid residue for binding of TWEAK to Fn14 (FIG. 6B). Based on these results, all further experiments utilized sTWEAK with substitutions at residue Y176.

Example 6

Non-Denaturing/Native Gel Electrophoresis

Figure 7:
FIG. 7 depicts substitution of TWEAK Y176 does not significantly affect TWEAK structure or surface charge. IVTT lysates containing FLAG epitope-tagged sTWEAK, sTWEAK Y176A, and sTWEAK Y176F were resolved by native gel electrophoresis. Lysates were immunoblotted with anti-FLAG monoclonal antibody. IVTT lysate with GFP cDNA as template was run as negative control and IVTT containing a cDNA encoding an unrelated FLAG epitope-tagged MAP4K4 fragment was run as a positive control for the FLAG antibody.

The results of the ELISA indicated that substitution of TWEAK Y176 disrupted TWEAK binding to Fn14. To examine whether substitution of Y176 caused significant changes in the secondary, tertiary, or quaternary structure of TWEAK, we performed non-denaturing gel electrophoresis comparing sTWEAK and sTWEAK Y176 variants. As shown in FIG. 7, sTWEAK, sTWEAK Y176A, and sTWEAK Y176F exhibited similar bands between 66 KDa and 146 KDa when immunoblotted with an anti-FLAG antibody, indicative of sTWEAK trimer. IVTT lysate generated with a cDNA for GFP was used as a control and did not show any specific anti-FLAG staining. These results demonstrate that the conservative substitutions of Y176→A or Y176→F did not appear to cause significant changes in structure and surface charge relative to sTWEAK suggesting that the sTWEAK Y176 variants also exist in a homotrimeric state similar to wild type sTWEAK (Winkles J A (2008) Nat Rev Drug Discov 7: 411-425; Schneider P, Schwenzer R, Haas E, Muhlenbeck F, Schubert G, et al. (1999) Eur J Immunol 29: 1785-1792).

Example 7

Luciferase Induction Assay

Figure 8:
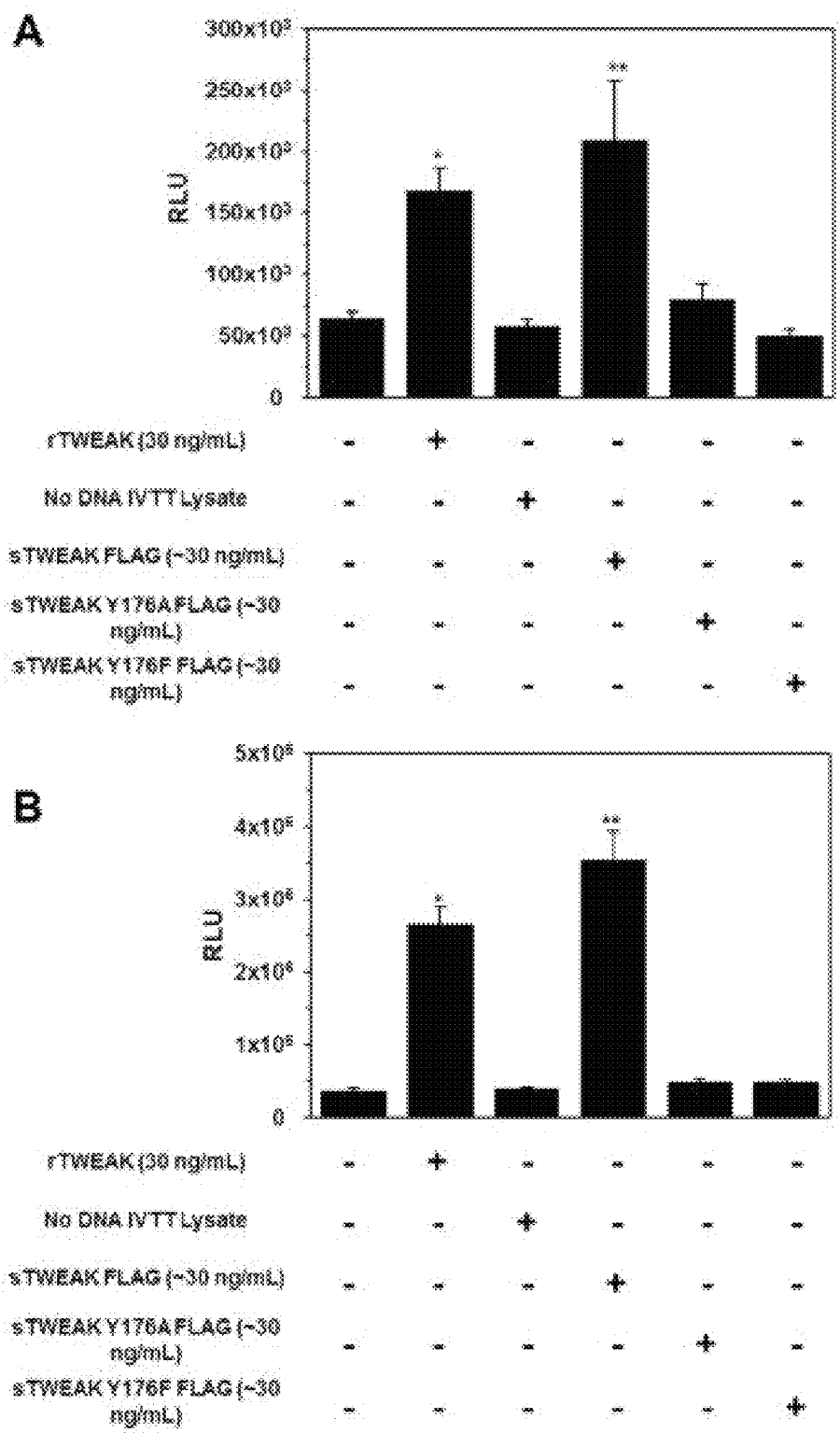
FIG. 8 depicts substitution of TWEAK Y176 inhibits Fn14 mediated NF-κB. 8A, HEK293 expressing a NF-κB luciferase reporter were treated with rTWEAK, or IVTT synthesized sTWEAK, sTWEAK Y176A, or sTWEAK Y176F. After 5 hr incubation, luciferase generation was detected with Bright Glo reagent. *, $p<0.05$, **, $p<0.01$. 8B, HEK293 NF-κB luciferase cells overexpressing full length Fn14 were treated with rTWEAK or IVTT synthesized sTWEAK, sTWEAK Y176A, or sTWEAK Y176F. After 5 hr incubation, luciferase generation was detected with Bright Glo reagent. *, $p<0.005$, **, $p<0.001$.

The ELISA indicated that substitution of Y176 significantly reduced sTWEAK binding to Fn14. Furthermore, native gel electrophoresis further indicated that conservative substitutions of Y176 did not cause obvious alterations in sTWEAK structure and surface charge. However, neither of these assays can accurately predict the effect of the sTWEAK variants on Fn14 cellular signaling. TWEAK binding to the Fn14 receptor results in NF-κB phosphorylation (Tran N L, McDonough W S, Savitch B A, Sawyer T F, Winkles J A, et al. (2005) J Biol Chem 280: 3483-3492). Therefore, we examined the ability of sTWEAK and the sTWEAK Y176 variants to initiate Fn14 signaling using cells expressing a NF-κB luciferase reporter. Stimulation of HEK293 cells expressing the NF-κB luciferase reporter with sTWEAK Y176A or sTWEAK Y176F resulted in luciferase expression that was 87% and 100% less respectively than cells stimulated with sTWEAK (FIG. 8A). Cells treated with IVTT lysate without cDNA template or with recombinant TWEAK served as controls. Immunoblotting of IVTT lysates (FIG. S1) ensured equivalent amounts of sTWEAK and sTWEAK Y176 variants were added to the cells. Additionally, induction of luciferase expression in HEK293 NF-κB luciferase cells that also stably overexpress full length Fn14 was 98% less following stimulation with sTWEAK Y176A or sTWEAK Y176F relative to cells stimulated with sTWEAK (FIG. 8B). Together, these results substantiate the results of the ELISA and indicate that substitution of TWEAK Y176 abrogates TWEAK binding to cellular Fn14 and Fn14 signaling. These results are consistent with those published very recently by Pellegrini et al. in a structural biology study focused on the structural characterization of the Fn14-TWEAK binding interface in two different species to investigate the evolution of structural conservation in the cysteine rich domains of the TNF receptor family (Pellegrini, M., et al. (2013) FEBS J 280, 1818-1829).

Example 8

In Silico Identification of Small Molecule Inhibitors of TWEAK-Fn14 Interaction

Figure 9:
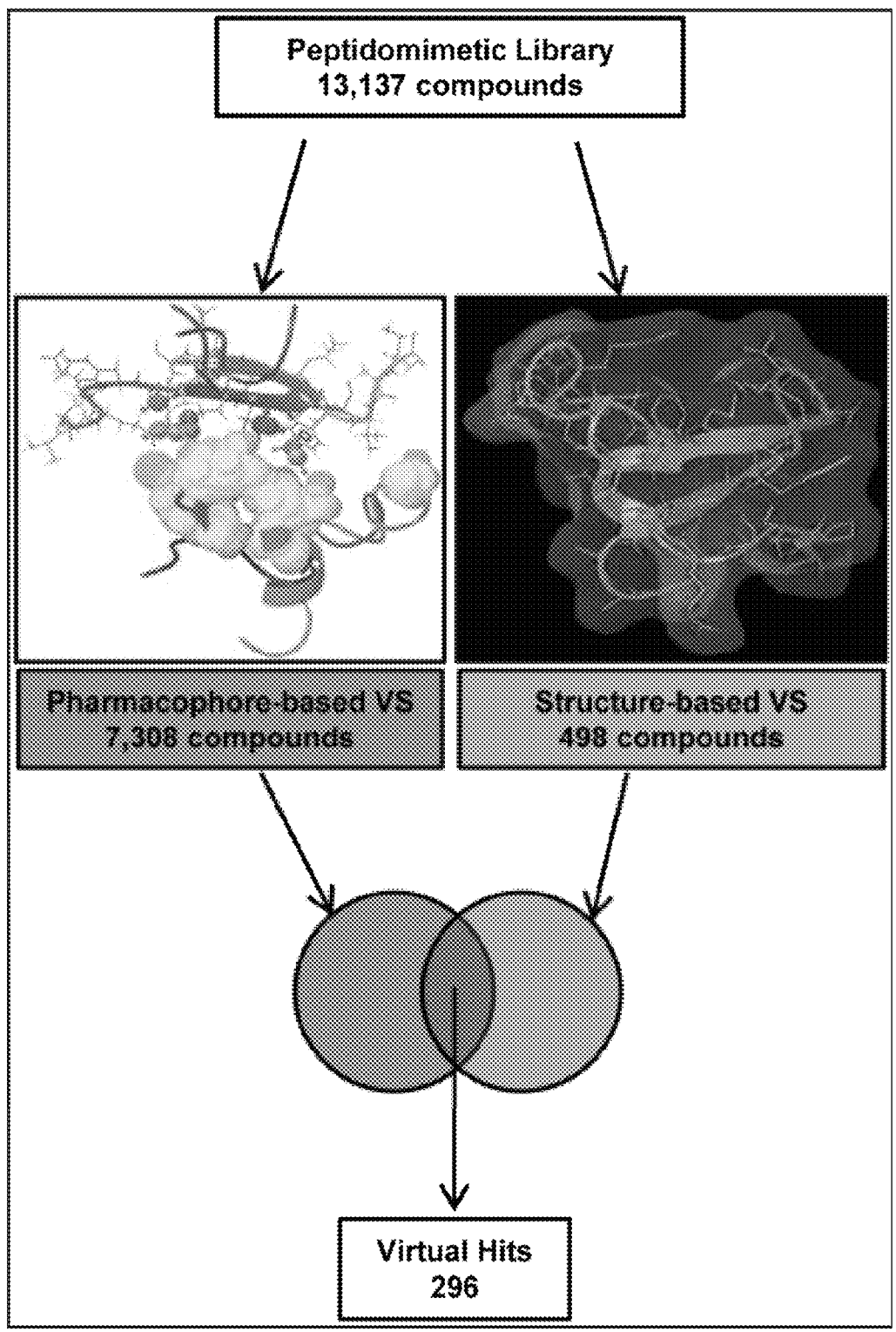
FIG. 9 depicts virtual screening workflow for in silico peptidomimetic compound selection. Two parallel virtual screening (VS) strategies were implemented to identify virtual hits from a vendor compound library of peptidomimetic molecules (ChemDiv, 13,637 compounds). The pharmacophore-based virtual screening provided a biased approach utilizing the protein-protein complexes identified in FIG. 4A-B. The structure-based virtual screening utilized an optimized Fn14 CRD model to identify candidate compounds from the initial library. Both result sets were intersected and compounds identified by both methodologies were considered as virtual hits and selected for further testing.

The work presented above predicted plausible binding modes of the TWEAK-Fn14 association involving TWEAK residue Y176, and was validated experimentally. These data provided a structural basis to enable further examination of the chemical tractability of the system with the goal to determine whether the characterized TWEAK-Fn14 interaction would be of utility as a therapeutic target for small molecule discovery. To pursue that goal, the structural TWEAK-Fn14 complexes predicted by protein-protein docking involving the Y176 anchoring residue of TWEAK to Fn14 were used as starting point for virtual screening of a library of commercially available small molecules. The peptidomimetic set of ChemDiv (13,137 compounds, v05.2011) was selected for this study and pre-processed as described in methods. A two-pronged virtual screening workflow intersecting the results of a ligand-biased pharmacophore-based and an unbiased structure-based approach was followed, as illustrated in FIG. 9. In the pharmacophore-based virtual screening approach, the two TWEAK-Fn14 complexes predicted by protein-protein docking (Y176 anchor models) served as a structural basis to generate two distinct pharmacophore hypotheses respectively composed of 10 and 13 sites (Table 2). Virtual hits were defined as those compounds matching the required pharmacophoric sites of the model, and matching three of the optional sites. The hit lists from both models were combined, leading to a set of 7,308 compounds. In the parallel structure-based approach, a sequential high throughput docking workflow was followed in three steps, as described in methods. The best NMR model (model 1) was prepared and optimized, leading to a change in receptor side chain orientations. This optimized geometry of the Fn14 CRD was utilized as a receptor for structure-based virtual screening, to eliminate potential bias from protein-protein docking. The set of solutions included 498 compounds, after removal of redundancies. The intersection of this hit list, with that obtained via pharmacophore-based virtual screening produced an ensemble of 296 compounds considered as virtual hits. Among these, 60 were readily available in our internal compound collection and were advanced to screening in the ELISA.

TABLE 2

Pharmacophore sites for two TWEAK-Fn14 models validated after protein-protein docking. Sites corresponding to the anchoring residues are required as a pharmacophore match. A compound with modulating activity of TWEAK-Fn14 binding may also match one or more of the additional pharmacophoric sites shown.

| TWEAK-Fn14 Model | TWEAK residues | Pharmacophoric Site* |
|---|---|---|
| Y176 Model 1 | Y176(anchor) | R, A, D (required) |
| | Q123 | D, D, A |
| | K178 | P, D |
| | T198 | A, D |
| Y176 Model 2 | Y176(anchor) | R, A, D (required) |
| | K173 | P, D, D |
| | A174 | A, D |
| | R227 | H, P |
| | W231 | R, R, D |

*Pharmacophoric site legend: D—Hydrogen-bond donor; A—Hydrogen-bond acceptor; H—Hydrophobic; P—Positive ionic; R—Aromatic ring.

Example 9

ELISA Assay and Expansion on Actives

Figure 10:
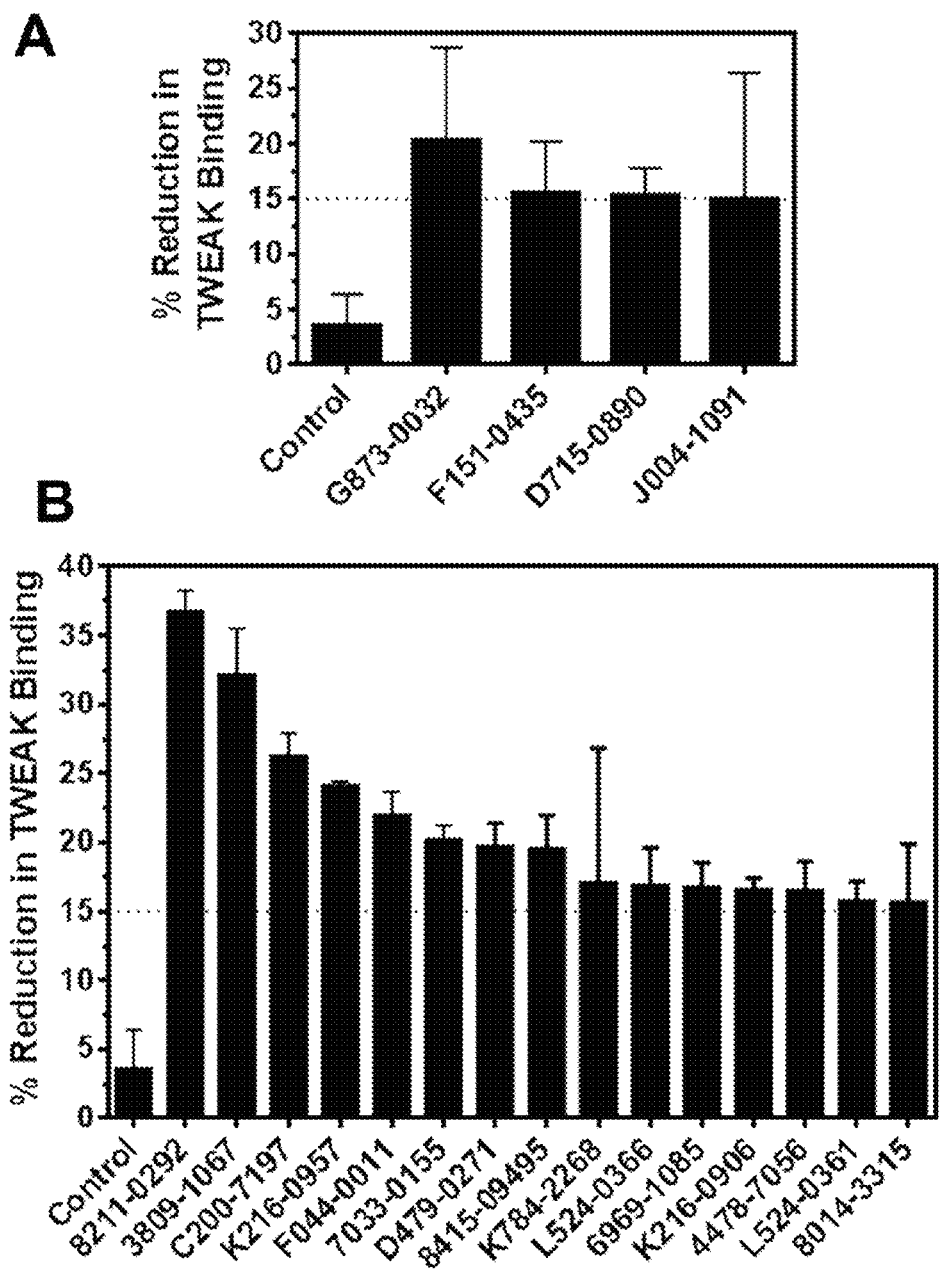
FIG. 10A depicts the average inhibitory activities for compounds that demonstrated ≥15% reduction in Fn14-TWEAK binding in the ELISA assay during the first round of screening (4 of 60 compounds).
FIG. 10B depicts the average inhibitory activities for compounds that demonstrated ≥15% reduction in Fn14-TWEAK binding in the ELISA assay during the follow up round of screening (15 of 69 compounds).

The 60 compounds selected by virtual screen were supplied from the internal compound collection and assayed in the ELISA screen as described in methods. These compounds demonstrated variable inhibitory activity of the Fn14-TWEAK interaction, with individual data points ranging from 0 to 26%. The data set capturing the reduction in Fn14-TWEAK binding demonstrated by each compound was rank-ordered by decreasing average inhibition, and summarized in Table 3. As shown in FIG. 10A, 4 compounds from the supplier ChemDiv with compound identifiers G873-0032, F151-0435, D715-0890, and J004-1091 showed an average inhibition in TWEAK-Fn14 binding over 15%. Compounds with similar scaffolds and single point activities above 15% were also identified (G873-0031 and D715-0114, highlighted in red in Table ST1). Finally, compounds with high repeatability and moderate activities slightly under 15% of activity were identified in the top 10 compounds and were also retained for further consideration (D715-2673, F044-0043, and F044-0075, see Table 3). Indeed, two of these molecules present similar scaffolds (F044-0043 and F044-0075) and a third one, D715-2673, shares similarity to two other compounds discussed above (D715-0890 and D715-0114). The structures of these molecules are provided in FIG. S2 (Supplementary FIG. 2). To confirm the mild activities observed in these five scaffold classes in the first screening iteration, these five chemical spaces were expanded. Common core scaffolds were identified and deconstructed in smaller substructures. These core substructures served as query to perform a substructure search in the ChemDiv online catalogue. Compounds matching those queries were further triaged by eye to remove those compounds with flags for reactivity, and a total of 69 compounds were procured. These compounds were plated as described in methods and evaluated for Fn14-TWEAK inhibition in a second screening iteration using the ELISA. The results, summarized in Table 4, clearly show a significant increase in activity with individual measurements reaching up to 37.8% inhibition of TWEAK-Fn14 interaction. 15 out of 69 compounds showed ≥15% and 6 out 69 compounds showed ≥20% inhibition of TWEAK binding to Fn14 (FIG. 10B). Compounds 8211-0292 and 3809-1067 reached 36.7% and 32.1% inhibition in TWEAK binding to Fn14, respectively. Interestingly, five of the 6 most active compounds result from the scaffold expansion of the core substructures of compound F151-0435 (Supplementary FIG.

3). These results indicate the chemical tractability of the TWEAK-Fn14 target of interest.

TABLE 3

Reduction in Fn14-TWEAK binding demonstrated by selected small molecules rank-ordered by decreasing average inhibition.

| | | % Reduction in TWEAK Binding | | | |
|---|---|---|---|---|---|
| Rank | Compound ID | Data 1 | Data 2 | Average | Std. Dev |
| 1 | G873-0032 | 26.29124 | 14.49096 | 20.3911 | 8.34405801 |
| 2 | F151-0435 | 18.85574 | 12.2198 | 15.53777 | 4.69231817 |
| 3 | D715-0890 | 17.06518 | 13.63294 | 15.34906 | 2.42696018 |
| 4 | J004-1091 | 23.07252 | 6.98396 | 15.02824 | 11.3763299 |
| 5 | D715-2673 | 14.27646 | 14.70548 | 14.49097 | 0.30336925 |
| 6 | G873-0031 | 20.28324 | 8.0563 | 14.16977 | 8.64575219 |
| 7 | F044-0043 | 12.77492 | 14.70548 | 13.7402 | 1.36511207 |
| 8 | Z250-1348 | 16.63612 | 9.98656 | 13.31134 | 4.70194897 |
| 9 | F044-0075 | 13.20392 | 12.77492 | 12.98942 | 0.30334881 |
| 10 | F044-0058 | 9.98656 | 14.06194 | 12.02425 | 2.88172883 |
| 11 | Z250-1266 | 16.20708 | 7.4129 | 11.80999 | 6.21842431 |
| 12 | D715-0140 | 9.77208 | 13.63294 | 11.70251 | 2.73004029 |
| 13 | F151-0392 | 9.03634 | 14.18252 | 11.60943 | 3.63889878 |
| 14 | F044-0077 | 12.56044 | 10.41552 | 11.48798 | 1.51668748 |
| 15 | F151-0458 | 10.7496 | 11.4845 | 11.11705 | 0.51965277 |
| 16 | F044-0083 | 11.05898 | 10.8445 | 10.95174 | 0.15166026 |
| 17 | F044-0076 | 8.54722 | 13.2008 | 10.87401 | 3.29057797 |
| 18 | F151-0419 | 8.79176 | 12.95548 | 10.87362 | 2.94419465 |
| 19 | F042-0072 | 12.95548 | 7.81384 | 10.38466 | 3.63568851 |
| 20 | D715-0114 | 0.97952 | 19.6396 | 10.30956 | 13.1946691 |
| 21 | F151-0485 | 14.67366 | 5.86002 | 10.26684 | 6.23218461 |
| 22 | D715-0817 | 9.03634 | 11.4845 | 10.26042 | 1.73111054 |
| 23 | L524-0064 | 9.77208 | 9.77208 | 9.77208 | 0 |
| 24 | D718-0101 | 7.56946 | 10.99452 | 9.28199 | 2.42188315 |
| 25 | F151-0439 | 9.28096 | 9.28096 | 9.28096 | 0 |
| 26 | G873-0027 | 10.50472 | 7.81384 | 9.15928 | 1.9027395 |
| 27 | F354-0046 | 7.56946 | 10.50472 | 9.03709 | 2.07554225 |
| 28 | D715-2740 | 7.19842 | 9.98656 | 8.59249 | 1.9715127 |
| 29 | G282-0614 | 9.34312 | 7.4129 | 8.37801 | 1.36487165 |
| 30 | D715-1690 | 6.8366 | 9.03634 | 7.93647 | 1.55545107 |
| 31 | F044-0055 | 8.48524 | 7.19842 | 7.84183 | 0.90991915 |
| 32 | P772-0029 | 6.55504 | 8.6997 | 7.62737 | 1.51650363 |
| 33 | D718-0863 | 6.98396 | 8.0563 | 7.52013 | 0.75825889 |
| 34 | F151-0306 | 6.1041 | 8.79176 | 7.44793 | 1.90046261 |
| 35 | F044-0038 | 7.19842 | 7.62736 | 7.41289 | 0.30330638 |
| 36 | F540-0151 | 6.8366 | 7.32514 | 7.08087 | 0.34544995 |
| 37 | D715-1634 | 3.9088 | 10.01508 | 6.96194 | 4.317792 |
| 38 | L900-0843 | 1.47334 | 11.4845 | 6.47892 | 7.07895912 |
| 39 | F151-0406 | 7.81384 | 4.6402 | 6.22702 | 2.24410237 |
| 40 | D715-1082 | 2.2661 | 9.34312 | 5.80461 | 5.00420883 |
| 41 | D715-0820 | 2.93414 | 8.30272 | 5.61843 | 3.79615932 |
| 42 | D715-0116 | 4.15256 | 6.8366 | 5.49458 | 1.89790288 |
| 43 | C651-0500 | 5.61598 | 5.37198 | 5.49398 | 0.17253405 |
| 44 | D715-2352 | 6.34822 | 4.39636 | 5.37229 | 1.38017344 |
| 45 | F151-0480 | 4.39636 | 6.1041 | 5.25023 | 1.20755453 |
| 46 | D715-0183 | 4.6402 | 5.86002 | 5.25011 | 0.86254299 |
| 47 | D715-0841 | 9.52562 | 0.50024 | 5.01293 | 6.3819074 |
| 48 | D715-0828 | 0.74346 | 8.54722 | 4.64534 | 5.51809161 |
| 49 | D349-2152 | 3.17774 | 5.86002 | 4.51888 | 1.89665838 |
| 50 | D715-0754 | 3.4214 | 5.61598 | 4.51869 | 1.5518024 |
| 51 | D715-0343 | 3.17774 | 5.128 | 4.15287 | 1.37904207 |
| 52 | D715-1633 | 3.66508 | 2.44706 | 3.05607 | 0.8612702 |
| 53 | F255-0266 | 1.23 | 4.39636 | 2.81318 | 2.23895453 |
| 54 | G639-3205 | 1.47334 | 4.15256 | 2.81295 | 1.89449463 |
| 55 | F044-0056 | 2.2661 | 3.12386 | 2.69498 | 0.60652791 |
| 56 | F538-3693 | 0.50024 | 4.88408 | 2.69216 | 3.09984299 |
| 57 | F151-0461 | 2.20356 | 2.69058 | 2.44707 | 0.34437514 |
| 58 | D715-0736 | 2.69058 | 1.71672 | 2.20365 | 0.68862301 |
| 59 | F354-0148 | 3.55274 | 0.55068 | 2.05171 | 2.12277698 |
| 60 | F532-4387 | -3.14346 | 2.44706 | -0.3482 | 3.9530946 |

TABLE 4

Reduction in Fn14-TWEAK binding demonstrated by selected small molecules rank-ordered by decreasing average inhibition.

| | | % Reduction in TWEAK Binding | | | |
|---|---|---|---|---|---|
| Rank | Compound ID | Data 1 | Data 2 | Average | Std. Dev |
| 1 | 8211-0292 | 35.5788 | 37.828 | 36.7034 | 1.59042457 |
| 2 | 3809-1067 | 34.5214 | 29.77606 | 32.14873 | 3.35546209 |
| 3 | C200-7197 | 27.4414 | 25.08022 | 26.26081 | 1.66960639 |
| 4 | K216-0957 | 23.8097 | 24.28708 | 24.04839 | 0.33755864 |
| 5 | F044-0011 | 20.75978 | 23.17146 | 21.96562 | 1.70531528 |
| 6 | 7033-0155 | 19.46154 | 20.92148 | 20.19151 | 1.03233347 |
| 7 | D479-0271 | 20.92148 | 18.48222 | 19.70185 | 1.72481729 |
| 8 | 8415-09495 | 17.82662 | 21.24446 | 19.53554 | 2.41677784 |
| 9 | K784-2268 | 23.96896 | 10.1232 | 17.04608 | 9.79043079 |
| 10 | L524-0366 | 18.81436 | 14.9368 | 16.87558 | 2.74184897 |
| 11 | 6969-1085 | 15.51452 | 17.99072 | 16.75262 | 1.75093781 |
| 12 | K216-0906 | 17.16882 | 16.01228 | 16.59055 | 0.81779728 |
| 13 | 4478-7056 | 15.01546 | 17.99072 | 16.50309 | 2.10382652 |
| 14 | L524-0361 | 14.6576 | 16.74424 | 15.70092 | 1.47547729 |
| 15 | 8014-3315 | 18.64578 | 12.66932 | 15.65755 | 4.22599539 |
| 16 | F281-0079 | 15.51452 | 13.67832 | 14.59642 | 1.29838947 |
| 17 | 1068-0114 | 21.88884 | 4.92556 | 13.4072 | 11.9948503 |
| 18 | G003-0114 | 14.68204 | 11.31564 | 12.99884 | 2.38040427 |
| 19 | 4981-0539 | 11.31564 | 12.1628 | 11.73922 | 0.59903258 |
| 20 | L524-0322 | 17.0212 | 6.27078 | 11.64599 | 7.60169488 |
| 21 | 4084-0026 | 15.34832 | 6.84814 | 11.09823 | 6.01053492 |
| 22 | 5511-0142 | 7.19558 | 13.84598 | 10.52078 | 4.70254294 |
| 23 | K784-2273 | 10.46466 | | 10.46466 | |
| 24 | K216-0857 | 8.06138 | 11.82438 | 9.94288 | 2.66084282 |
| 25 | G856-7200 | 9.43844 | 10.1232 | 9.78082 | 0.48419844 |
| 26 | L524-0313 | 10.28866 | 9.14798 | 9.71832 | 0.80658256 |
| 27 | K784-2269 | 10.8055 | 8.23408 | 9.51979 | 1.81826852 |
| 28 | 8004-5478 | 12.1628 | 5.9767 | 9.06975 | 4.37423326 |
| 29 | F044-0067 | 10.8569 | 6.9936 | 8.92525 | 2.73176563 |
| 30 | L524-0066 | 11.28218 | 6.5602 | 8.92119 | 3.33894408 |
| 31 | L524-0347 | 16.32826 | 1.4376 | 8.88293 | 10.5292867 |
| 32 | K216-0855 | 7.71554 | 9.60986 | 8.6627 | 1.33948652 |
| 33 | F044-0064 | 8.86192 | 7.85784 | 8.35988 | 0.70999178 |
| 34 | L524-0314 | 8.5755 | 7.85784 | 8.21667 | 0.50746225 |
| 35 | F044-0039 | 7.28206 | 9.14798 | 8.21502 | 1.31940469 |
| 36 | F044-0013 | 14.09824 | 2.32476 | 8.2115 | 8.32510755 |
| 37 | F044-0069 | 12.41254 | 3.94136 | 8.17695 | 5.99002882 |
| 38 | F044-0074 | 13.25684 | 2.91408 | 8.08546 | 7.31343573 |
| 39 | L524-0071 | 8.14518 | 6.84922 | 7.4972 | 0.9163821 |
| 40 | F044-100 | 12.41254 | 2.17718 | 7.29486 | 7.23749246 |
| 41 | F044-0068 | 10.28866 | 3.06114 | 6.6749 | 5.1106284 |
| 42 | F044-0044 | 7.57014 | 4.23394 | 5.90204 | 2.35904964 |
| 43 | F044-0062 | 8.5755 | 3.2081 | 5.8918 | 3.79532494 |
| 44 | F044-0038 | 9.71904 | 2.02948 | 5.87426 | 5.43734002 |
| 45 | L524-0084 | 3.94136 | 7.28206 | 5.61171 | 2.36223162 |
| 46 | L524-0076 | 16.74424 | -5.80816 | 5.46804 | 15.946955 |
| 47 | 4896-4789 | 6.67418 | 4.2215 | 5.44784 | 1.73430666 |
| 48 | L524-0090 | 4.9636 | 5.40022 | 5.18191 | 0.30873696 |
| 49 | F044-0072 | 4.5261 | 5.40022 | 4.96316 | 0.61809618 |
| 50 | F044-0086 | 3.7949 | 5.6908 | 4.74285 | 1.34060375 |
| 51 | F044-0045 | 7.28206 | 1.58574 | 4.4339 | 4.0279065 |
| 52 | L524-0065 | 3.64836 | 4.5261 | 4.08723 | 0.62065591 |
| 53 | F044-0091 | 9.14798 | -1.6989 | 3.72454 | 7.6699024 |
| 54 | L524-0081 | 6.70476 | 0.39762 | 3.55119 | 4.45982146 |
| 55 | 7033-1382 | 3.33764 | 3.33764 | 3.33764 | 0 |
| 56 | F044-0046 | 0.6953 | 5.83594 | 3.26562 | 3.6349814 |
| 57 | 1227-0070 | 5.45188 | 0.6604 | 3.05614 | 3.388088 |
| 58 | F044-0051 | 7.71404 | -1.6989 | 3.00757 | 6.6559537 |
| 59 | 4839-0022 | 5.80192 | -0.24074 | 2.78059 | 4.27280586 |
| 60 | 3652-0192 | 9.95224 | -4.81426 | 2.56899 | 10.4414923 |
| 61 | 4896-4951 | 3.51474 | 1.01962 | 2.26718 | 1.76431627 |
| 62 | F044-0076 | -2.30206 | 5.54556 | 1.62175 | 5.54910532 |
| 63 | 3076-0363 | 9.26686 | -8.18 | 0.54343 | 12.336793 |
| 64 | 4896-5164 | 1.37814 | -0.60244 | 0.38785 | 1.40048155 |
| 65 | L524-0319 | -2.60438 | 2.7669 | 0.08126 | 3.79806851 |
| 66 | F044-0048 | 3.94136 | -4.88716 | -0.4729 | 6.24270636 |
| 67 | 3448-7260 | -3.52206 | -1.87402 | -2.69804 | 1.16534026 |
| 68 | C200-5958 | | -5.74292 | -5.74292 | |
| 69 | 3525-0024 | -7.23876 | -12.76772 | -10.00324 | 3.90956511 |

Example 10

Cell Based Luciferase Induction Assay and Validation of Actives

Figure 11:
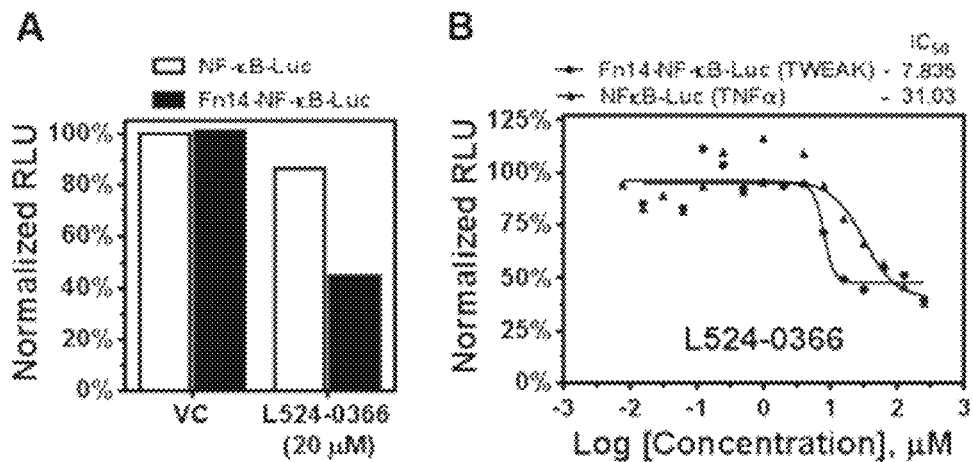
FIG. 11 depicts L524-0366 specifically inhibits TWEAK-Fn14 mediated NF-κB activation. 11A, NF-kB Luc reporter cells treated with TNFα or Fn14-NF-kB-Luc reporter cells treated with TWEAK were incubated with vehicle (VC) or L524-0366. NF-kB driven luminescent signal was determined using Bright-Glo assay. 11B, Dose response curve of inhibitory activity of L524-0366 in Fn14-NF-κB-Luc and NF-κB-Luc cells following TWEAK and TNFα stimulation respectively.

Compounds that demonstrated ≥15% inhibition of TWEAK binding to Fn14 in the ELISA assay were selected for further validation using a cell based NF-κB luciferase induction assay. A total of 19 compounds were selected and screened for their capacity to inhibit cellular NF-κB stimulated luciferase activity in NF-κB-Luc and Fn14-NF-κB-Luc cells stimulated with either TWEAK or TNFα. One compound, L524-0366, demonstrated significant inhibition of TWEAK-induced NF-κB driven luciferase activity in Fn14-NF-κB-Luc cells but only minor inhibition of TNFα-induced NF-κB driven luciferase activity in NF-κB-Luc cells (FIG. 11A). In addition, L524-0366 showed specific dose-dependent inhibition of TWEAK-Fn14 stimulated luciferase induction (FIG. 11B). L524-0366 showed approximately 5 fold higher inhibitory activity against TWEAK-Fn14 signaling (IC50 of 7.8 µM for Fn14-NF-κB-Luc cells stimulated with TWEAK as compared to IC50 of 31.03 µM for NF-κB-Luc cells stimulated with TNFα). Other compounds that exhibited inhibitory activity in the ELISA assay either did not demonstrate specific inhibition of TWEAK-Fn14 stimulated luciferase induction relative to TNFα stimulated luciferase induction or exerted significant cellular toxicity.

Example 11

Validation of TWEAK-Fn14 Interaction Inhibitor in Phenotypic Assay

Figure 12:
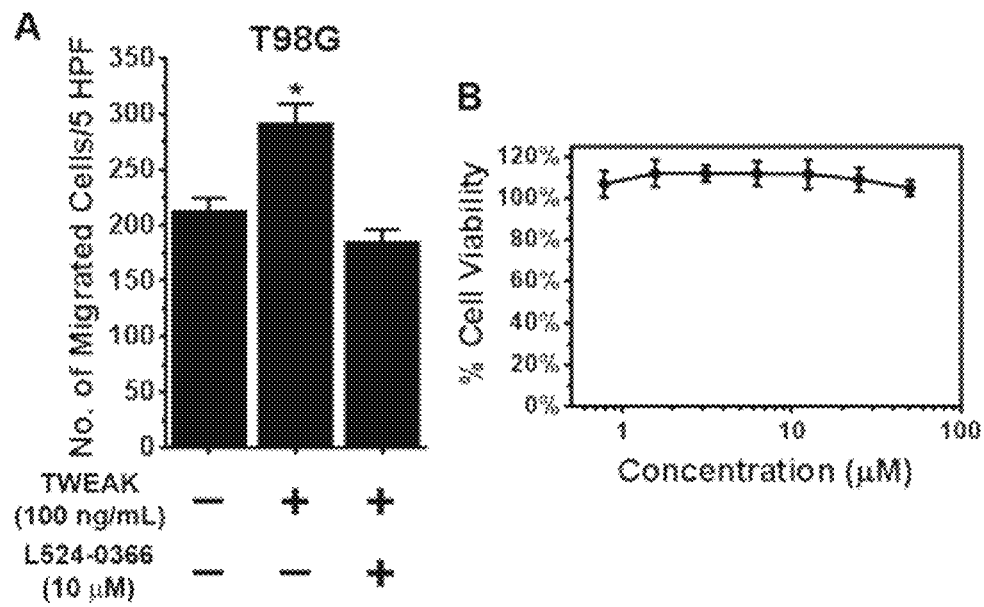
FIG. 12 depicts L524-0366 inhibits TWEAK induced glioma cell migration. 12A, T98G glioma cells were added to the top well of a modified transwell chamber pre-coated with collagen. TWEAK (100 ng/mL) or TWEAK and PP2 (10 μM) was added to the lower wells and the number of cells invaded to the bottom chamber quantitated after 5 hrs. Values are mean±standard deviation of triplicate measurements (*, $p<0.05$). HPF, High Power Field. 12B, Cytotoxic effect of L524-0366 on T98G glioma cells was assessed by quantifying metabolic activity of the cells after the drug treatment. Glioma cells were seeded in 96-well plates and after 24 hrs of incubation either vehicle (DMSO) or L524-0366 at indicated concentration was added to each well. After 72 hrs of incubation viability of the cells was measured using CellTiter-Glo assay kit. Values are mean±standard deviation of six separate measurements.
Figure 13:
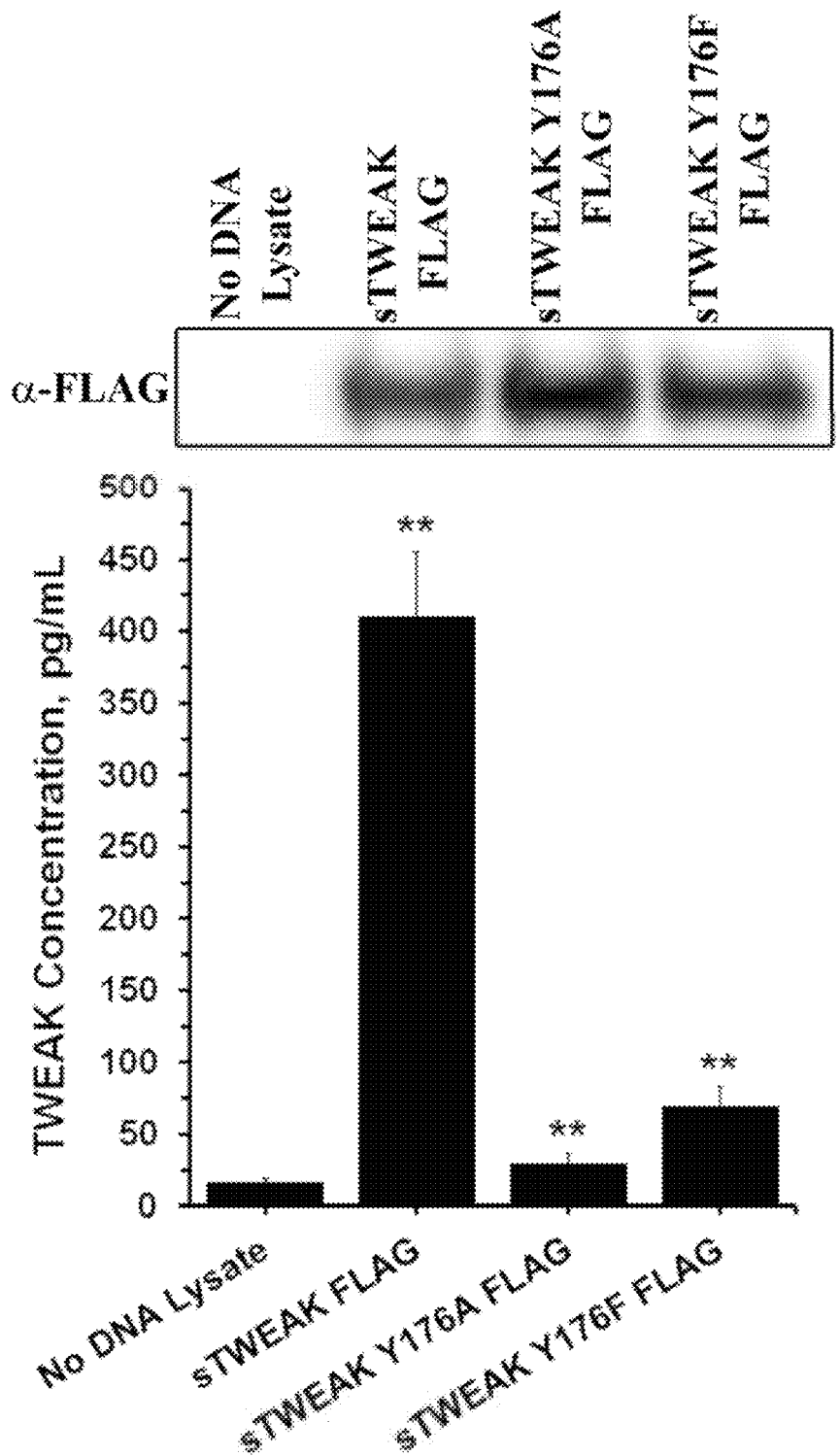
FIG. 13 depicts substitution of TWEAK Y176 disrupts Fn14-TWEAK interaction. 13A, Immunblot analysis of IVTT lysates using anti-FLAG antibody showing equal expression of sTWEAK and sTWEAK Y176 variants. 13B, Double sandwich ELISA depicting binding of sTWEAK and TWEAK Y176 variants to Fn14. sTWEAK shows significantly higher binding as compared to no DNA lysate control and TWEAK Y176 variants show significantly lower binding as compared to sTWEAK (**, $p<0.001$).
Figure 14:
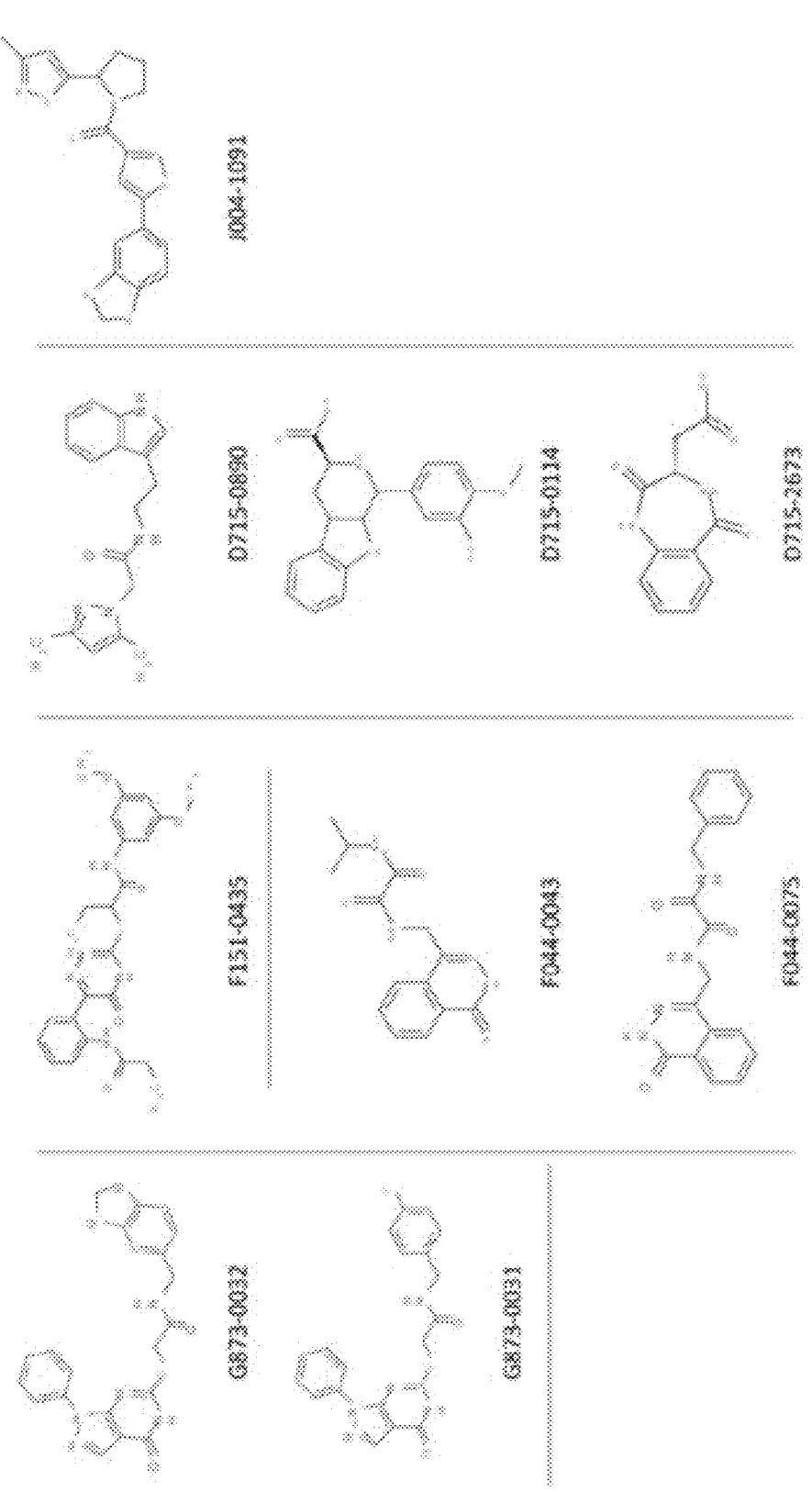
FIG. 14 depicts a first round of screening. Planar structures of active compounds identified in the first round of screening, grouped by structural similarity.
Figure 15:
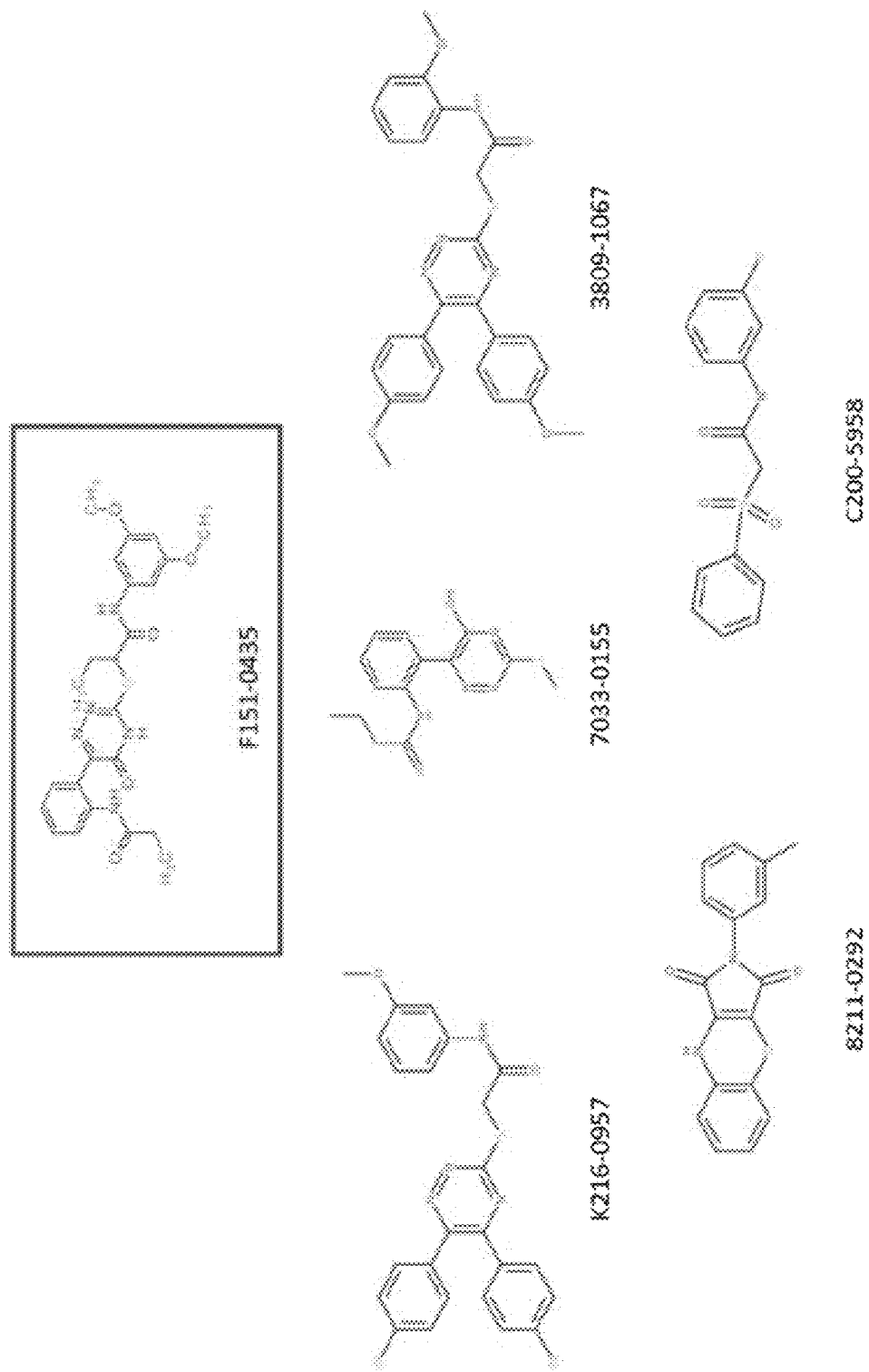
FIG. 15 depicts a second round of screening. Planar structures of five active compounds identified in the second round of screening, after expansion of chemical space around substructures of compound F151-0435.
Figure 16:
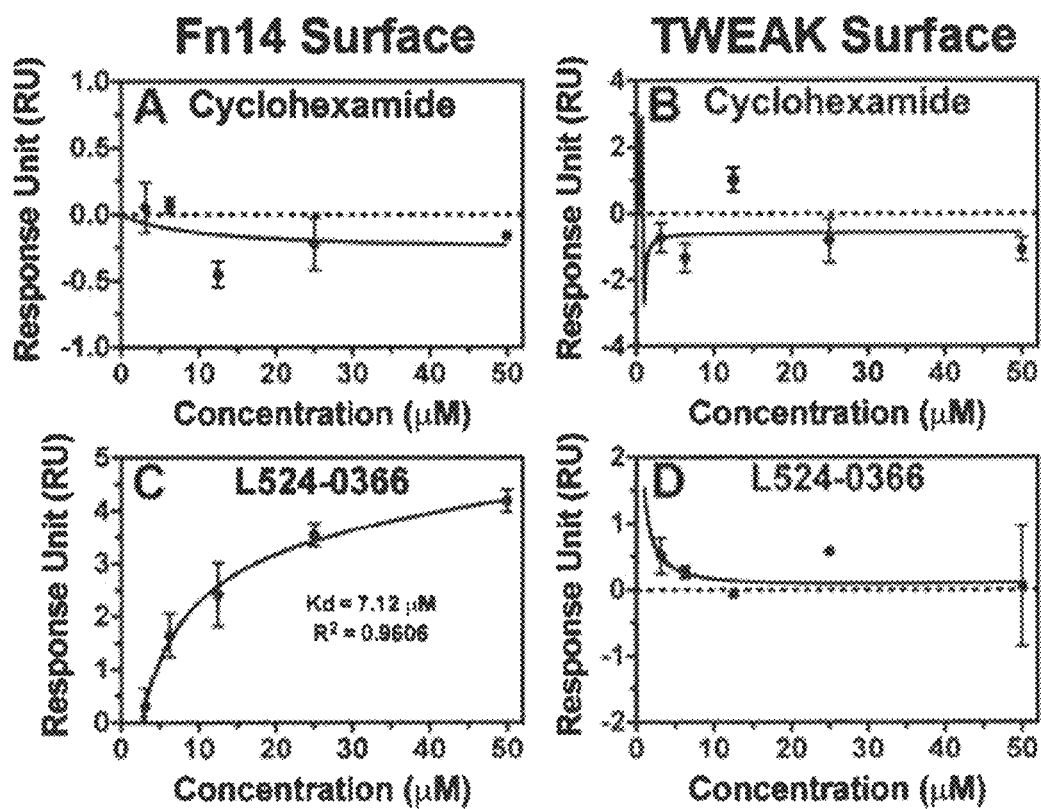
FIG. 16 depicts the specificity of a compound binding to Fn14. 16A and 16B, serial dilutions of cycloheximide from 0 to 50 μM, which were injected over Fn14 and TWEAK sensor surfaces and binding capacity of the cycloheximide was measured using a Surface Plasmon Resonance (SPR) assay. 16C and 16D, serial dilutions of L524-0366 from 0 to 50 μM were injected over Fn14 and TWEAK sensor surfaces and its binding affinity to Fn14 and TWEAK was measured using an SPR assay.

The capacity of L524-0366 to inhibit the binding of TWEAK to Fn14 and inhibit TWEAK-Fn14 signaling suggests that it could functionally inhibit endogenous Fn14. Therefore, we examined the capacity of L524-0366 to inhibit TWEAK induced glioma cell migration. While TWEAK significantly stimulated T98G glioma cell migration, L524-0366 (10 µM) completely suppressed TWEAK-induced T98G cell migration (FIG. 12A). Notably, addition of L524-0366 did not demonstrate any cytotoxicity up to 50 µM (FIG. 12B). Therefore, the observed decrease in glioma cell migration is not due to compound toxicity. Collectively, these results indicate the chemical tractability of the TWEAK-Fn14 target of interest and set the stage for subsequent medicinal chemistry efforts aimed at the identification and optimization of lead compounds capable of disrupting the interaction of Fn14 and TWEAK.

Example 12

SPR Assay Validates the Direct Interaction of L524-0366 with Fn14

Figure 19A:
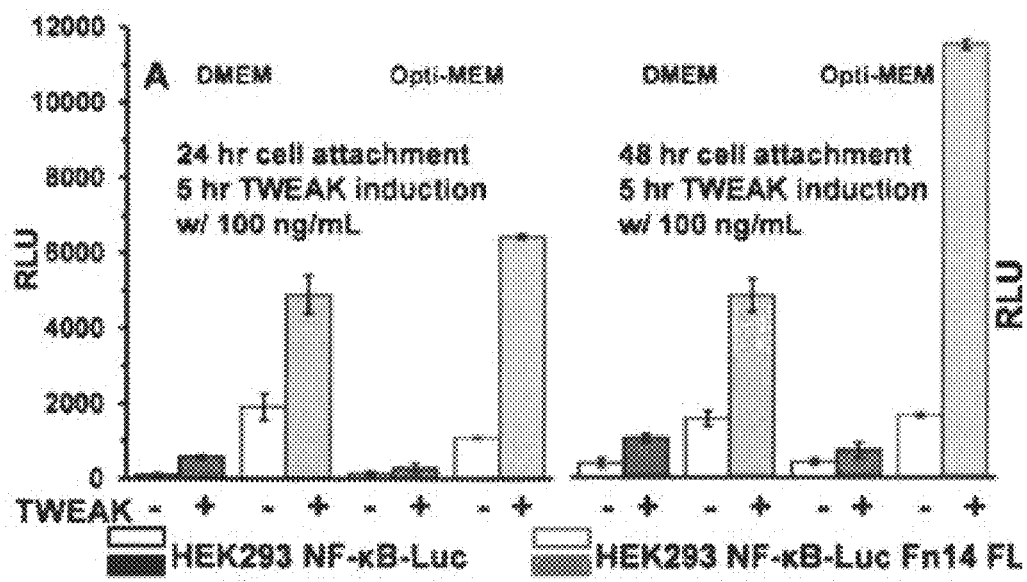
FIG. 19 depicts an initial verification of TWEAK-dependent induction of Fn14 signaling in a stable HEK293 Fn14-NF-κB -Luc Fn14 cell line in a 96-well format. 19A, the control HEK293 NF-κB -Luc and HEK293 Fn14 NF-κB -Luc were seeded at 10,000 cell/well in either Dulbecco's modified Eagle medium (DMEM) or Opti-MEM® (Life Technologies) and allowed to attach for either 24 or 48 hr and induced for 5 hr with 100 ng/mL of TWEAK in 96-well tissue-culture treated plates, then cells were lysed with Bright-Glo™ (Promega) and the Chemiluminescent signal read on and Biotek Synergy Plate Reader. 19B, the control HEK293 NF-κB-Luc and HEK293 Fn14 NF-κB-Luc were seeded into 96-well plates in Opti-MEM® and allowed to attach for 48 hr then induced with 0-200 n/mL of TWEAK for 5 hrs, then the signal was determined as in 19A using Perkin Elmer Envision.

To define the molecular basis of how L524-0366 inhibits the TWEAK-Fn14 signaling cascade, the interaction of L524-0366 with TWEAK and FN14 was analyzed using an SPR assay. The binding of cycloheximide to Fn14 or TWEAK was used as a control. While cycloheximide did not show significant binding to Fn14 or TWEAK (FIGS. 19A and 19B), L524-0366 bound specifically to the Fn14 surface with a $K_D$ of 7.12 µM (FIG. 19C), but not to the TWEAK surface (FIG. 19D). These results are coherent with the structure-guided strategy presented above, that targeted Fn14 CRD as the receptor for this study. The functionality of the TWEAK and Fn14 sensor surfaces was determined by observing the binding of TWEAK to the Fn14 surface and binding of Fn14-Fc to the TWEAK surface (data not shown).

The current work elucidated key structural elements of the TWEAK-Fn14 binding interaction using in silico protein modeling and protein-protein docking, followed by experimental validation in vitro. The results identified TWEAK Y176 as an anchor residue in the interaction of TWEAK with the Fn14 CRD. Leveraging this functionally validated information, we demonstrated that the predicted TWEAK-Fn14 interaction interface structural models could guide the virtual selection of small molecule inhibitors that disrupt the TWEAK-Fn14 interaction. By doing so, 60 compounds were identified, of which 4 were confirmed to inhibit TWEAK binding to Fn14 by ≥15% relative to control. These inhibitory activities were confirmed and increased in a second iteration of screening of 69 compounds selected by expanding the chemical spaces of active scaffolds identified in the initial screening iteration. A higher rate of actives was observed in this second screening as well as an overall increase in the average inhibitory activities, with a particular enrichment of actives around structures with similarity to one of the initial hits. Compounds that demonstrated ≥15% inhibition in TWEAK binding to Fn14 were further validated using a cell based functional screen that evaluates the ability of compounds to inhibit TWEAK-Fn14 signaling. One compound (L524-0366) was confirmed to be a specific dose-dependent inhibitor of TWEAK-Fn14 interaction and found to confer its activity by binding specifically to Fn14. Finally, L524-0366 demonstrated functional activity and completely suppressed TWEAK induced glioma cell migration without any potential cytotoxic effects. These results represent a significant step towards proving that the TWEAK-Fn14 interaction is chemically tractable and can serve as a foundation for further exploration utilizing chemical biology approaches focusing on functional validation of this interaction as a therapeutic target of interest in invasive cancers.

Additional compounds that have modulatory activity in the Fn14-TWEAK pathway are shown in Table 5. Any one of these compounds may be used in the compositions and methods of the present invention.

TABLE 5

Compounds identified as having modulatory activity in the Fn14-TWEAK pathway. The average percent reduction in TWEAK binding to Fn14 resulting from addition of the compounds is shown in the next to last column on the right side of the table.

| Molecular | | % Reduction in TWEAK Binding | | | |
|---|---|---|---|---|---|
| Formula | Structure | Data 1 | Data 2 | Average | Std. Dev |
| C15H14ClNOS | 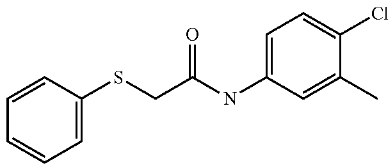  1068-0114 | 21.88884 | 4.92556 | 13.4072 | 11.99485032 |
| C26H24N4O4S | 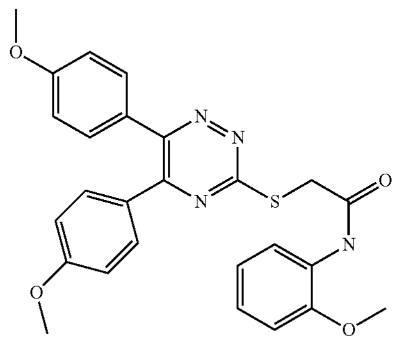  3809-1067 | 34.5214 | 29.77606 | 32.14873 | 3.355462093 |
| C21H16N2OS | 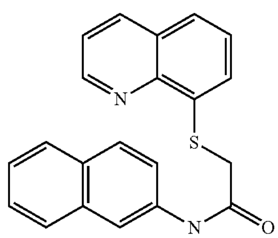  4084-0026 | 15.34832 | 6.84814 | 11.09823 | 6.010534919 |
| C18H20N2O2 | 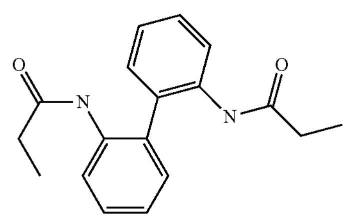  4478-7056 | 15.01546 | 17.99072 | 16.50309 | 2.103826522 |
| C26H20N6O3S3 | 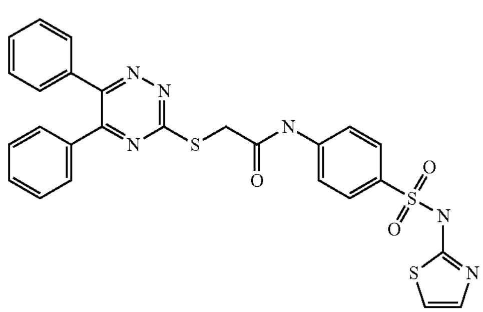  4981-0539 | 11.31564 | 12.1628 | 11.73922 | 0.599032581 |

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C15H18N4O2S | 5511-0142 | 7.19558 | 13.84598 | 10.52078 | 4.702542938 |
| C15H16N4O2S | 6969-1085 | 15.51452 | 17.99072 | 16.75262 | 1.750937812 |
| C14H16N4O2S | 7033-0155 | 19.46154 | 20.92148 | 20.19151 | 1.032333474 |
| C28H22N4O2S | 8014-3315 | 18.64578 | 12.66932 | 15.65755 | 4.225995393 |

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C17H12N2O2S | 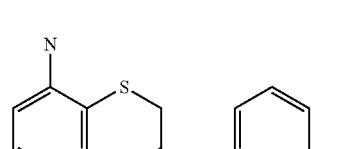<br>8211-0292 | 35.5788 | 37.828 | 36.7034 | 1.590424572 |
| C14H12N4OS2 | 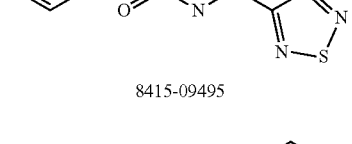<br>8415-09495 | 17.82662 | 21.24446 | 19.53554 | 2.416777841 |
| C17H15NO4S | 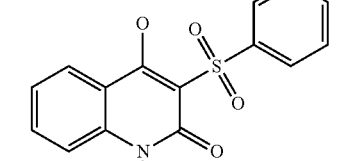<br>C200-7197 | 27.4414 | 25.08022 | 26.26081 | 1.66960639 |
| C16H14N2O2S | 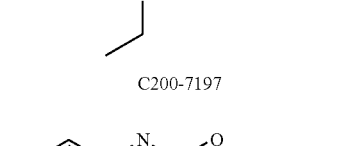<br>D479-0271 | 20.92148 | 18.48222 | 19.70185 | 1.724817287 |
| C19H18N2O4 | 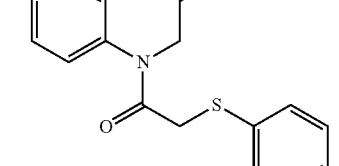<br>D715-0114 | 0.97952 | 19.6396 | 10.30956 | 13.19466911 |

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C13H14N2O2 | D715-0140 | 9.77208 | 13.63294 | 11.70251 | 2.730040287 |
| C19H14N2O3 | D715-0817 | 9.03634 | 11.4845 | 10.26042 | 1.731110537 |
| C17H20N4O | D715-0890 | 17.06518 | 13.63294 | 15.34906 | 2.426960179 |
| C11H10N2O4 | D715-2673 | 14.27646 | 14.70548 | 14.49097 | 0.303362951 |
| C19H18N4O3S | F042-0072 | 12.95548 | 7.81384 | 10.38466 | 3.63568851 |

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C17H20N4O3 | F044-0011 | 20.75978 | 23.17146 | 21.96562 | 1.705315282 |
| C14H16N4O3 | F044-0043 | 12.77492 | 14.70548 | 13.7402 | 1.365112067 |
| C16H20N4O4 | F044-0058 | 9.98656 | 14.06194 | 12.02425 | 2.881728834 |
| C18H16N4O3 | F044-0075 | 13.20392 | 12.77492 | 12.98942 | 0.303348809 |
| C18H15ClN4O3 | F044-0076 | 8.54722 | 13.2008 | 10.87401 | 3.290577975 |

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C18H15FN4O3 | F044-0077 | 12.56044 | 10.41552 | 11.48798 | 1.516687477 |
| C17H15N5O3 | F044-0083 | 11.05898 | 10.8445 | 10.95174 | 0.151660262 |
| C23H25N5O4S | F151-0392 | 9.03634 | 14.18252 | 11.60943 | 3.638898775 |
| C22H22ClN5O3S | F151-0419 | 8.79176 | 12.95548 | 10.87362 | 2.944194647

TABLE 5-continued
Compounds identified as having modulatory activity in the Fn14-TWEAK pathway. The average percent reduction in TWEAK binding to Fn14 resulting from addition of the compounds is shown in the next to last column on the right side of the table.
| Molecular Formula | Structure | % Reduction in TWEAK Binding | | | |
| --- | --- | --- | --- | --- | --- |
| | | Data 1 | Data 2 | Average | Std. Dev |
| C24H27N5O5S | 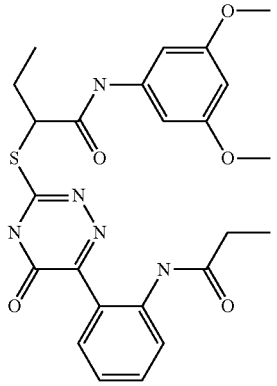<br>F151-0435 | 18.85574 | 12.2198 | 15.53777 | 4.692318174 |
| C22H23N5O3S | 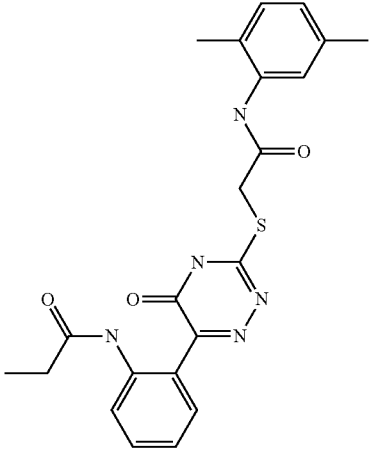<br>F151-0458 | 10.7496 | 11.4845 | 11.11705 | 0.519652773

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C25H25N3O7S | 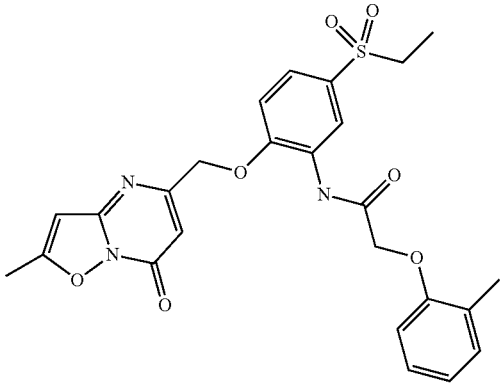 F172-0800 | 22.16916 | 17.1267 | 19.64793 | 3.56555766 |
| C14H11N3OS2 | 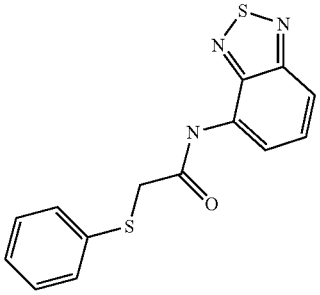 F281-00079 | 15.51452 | 13.67832 | 14.59642 | 1.298389472 |
| C17H21N3O3S2 | 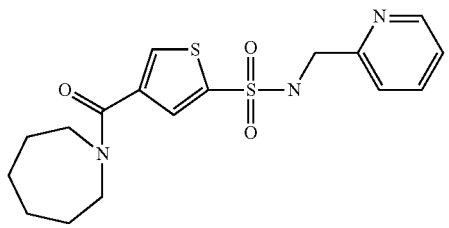 F540-1590 | 15.34 | 8.75888 | 12.04944 | 4.65355458 |
| C23H18N4OS | 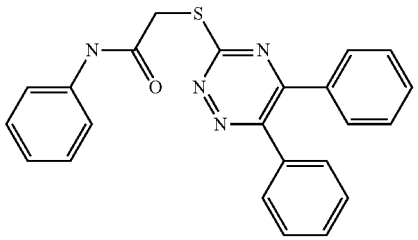 G003-0114 | 14.68204 | 11.31564 | 12.99884 | 2.380404268 |

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C20H16FN5O2S | G873-0031 | 20.28324 | 8.0563 | 14.16977 | 8.645752187 |
| C21H17N5O4S | G873-0032 | 26.29124 | 14.49096 | 20.3911 | 8.344058008 |
| C19H17N3O5 | J004-1091 | 23.07252 | 6.98396 | 15.02824 | 11.37632988 |
| C24H18F2N4O2S | K216-0906 | 17.16882 | 16.01228 | 16.59055 | 0.817797277 |

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C24H18Cl2N4O2S | K216-0957 | 23.8097 | 24.28708 | 24.04839 | 0.337558635 |
| C23H17ClN4OS | K784-2268 | 23.96896 | 10.1232 | 17.04608 | 9.790430787 |
| C24H20N4O2S | K784-2273 | 10.46466 | | 10.46466 | #DIV/0! |
| C13H13ClN4O | L524-0322 | 17.0212 | 6.27078 | 11.64599 | 7.601694883 |
| C12H11ClN4O | L524-0361 | 14.6576 | 16.74424 | 15.70092 | 1.475477294 |

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C13H13ClN4OS | 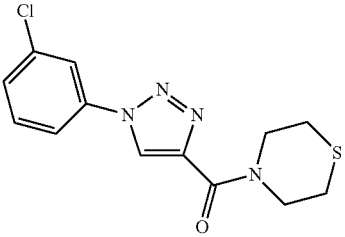 L524-0366 | 18.81436 | 14.9368 | 16.87558 | 2.74184897 |
| C18H18N4O2S | 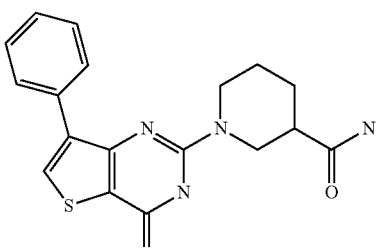 Z250-1266 | 16.20708 | 7.4129 | 11.80999 | 6.218424313 |
| C25H23FN4O2S | 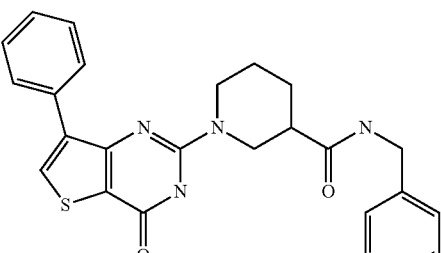 Z250-1300 | 28.06232 | 15.93596 | 21.99914 | 8.574631387 |
| C24H23N5O2S | 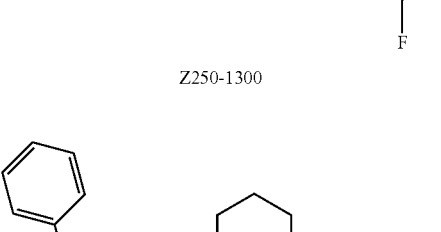 Z250-1329 | 13.40042 | 15.19094 | 14.29568 | 1.266088834 |

TABLE 5-continued

Compounds identified as having modulatory activity in the Fn14-TWEAK pathway. The average percent reduction in TWEAK binding to Fn14 resulting from addition of the compounds is shown in the next to last column on the right side of the table.

| Molecular Formula | Structure | % Reduction in TWEAK Binding | | | |
|---|---|---|---|---|---|
| | | Data 1 | Data 2 | Average | Std. Dev |
| C19H20N4O2S | 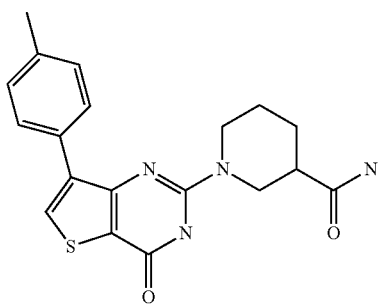 Z250-1348 | 16.63612 | 9.98656 | 13.31134 | 4.701948968 |

Example 13

Generation of Fn14-NF-κB-luciferase Cell Line and Assay Optimization

Figure 18:
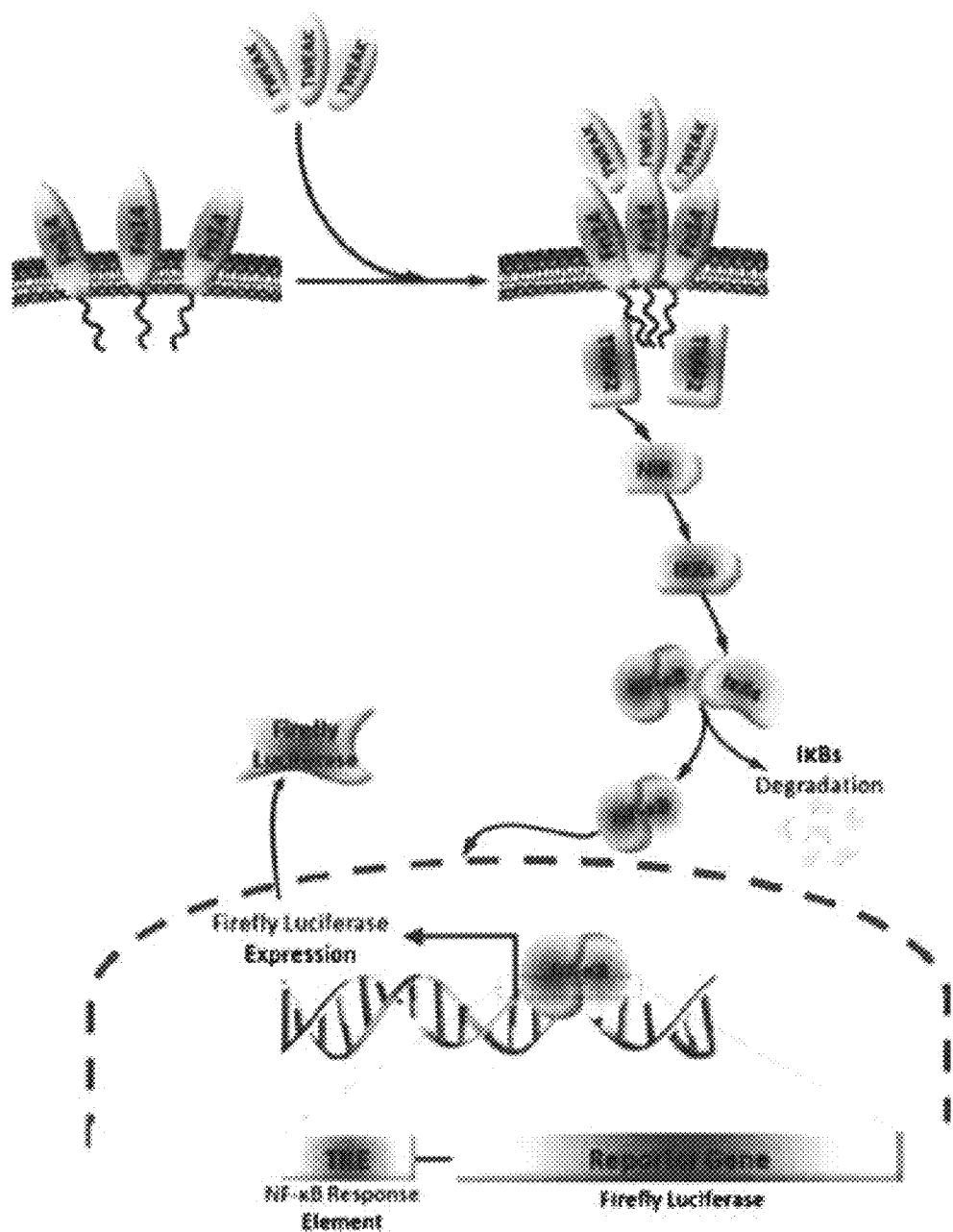
FIG. 18 depicts a schematic of TWEAK-Fn14 driven luciferase expression in a reporter cell line. TWEAK binding promotes Fn14 trimerization, TNFR-associated factor (TRAF) association with Fn14 and signal pathway activation downstream, which activates NF-κB. Activated NF-κB translocates to the nucleus and drives firefly luciferase expression and other NF-κB dependent genes.

Human embryonic kidney cells (HEK293) express low levels of the Fn14 receptor. We developed a cell-based assay for the Fn14-TWEAK pathway signaling events using HEK293 cells that stably co-expresses high levels of full length Fn14 receptor and a firefly luciferase reporter driven by NF-KB-response elements (Fn14-NF-KB-Luc). A schematic model of the cell-based TWEAK-Fn14-NF-KB luciferase reporter is shown in FIG. 18.

Figure 19B:
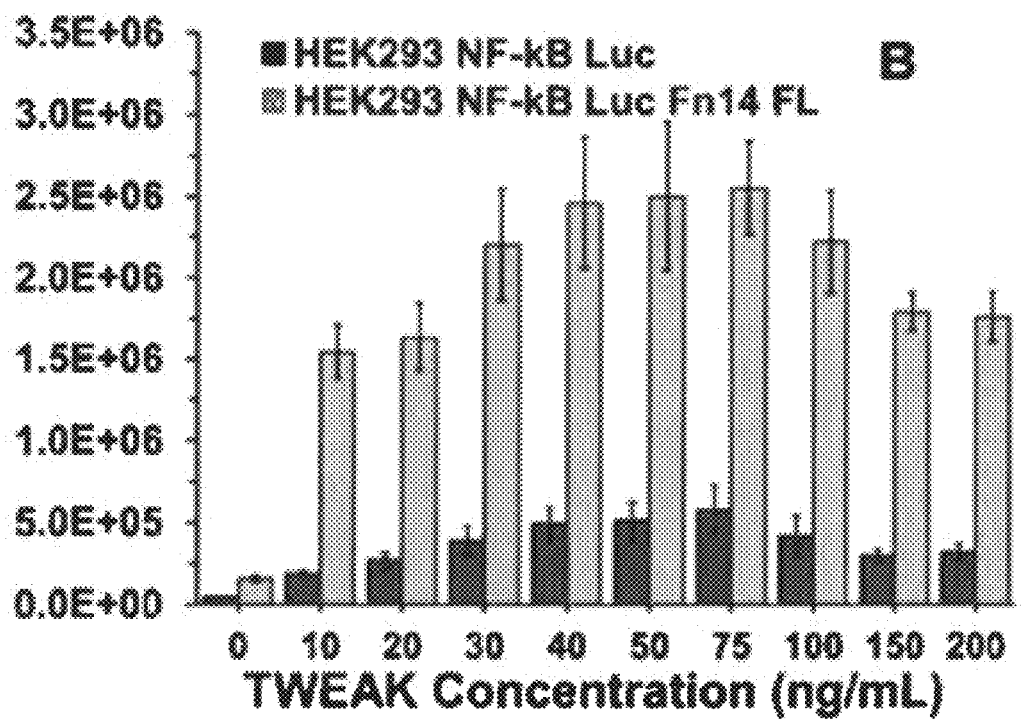

We optimized HEK293 Fn14-NF-KB Luc cell line for HTS by testing TWEAK-stimulated Luc-reporting as a function of growth medium, TWEAK concentration, induction time, assay duration, cell density, and DMSO concentration. For example, we seeded HEK293 Fn14-NF-KB-Luc and control cells (HEK293 NFKB-Luc) into a 96-well plate at a density of 10,000 cells/well, in DMEM or Opti-MEM® (Reduced serum media, protein concentration 15 µg/mL) and incubated at 37 C for 24 or 48 h. We then induced them with various concentrations of TWEAK in buffer or buffer alone (PBS+1 mg/mL BSA) for 5 hr and then measured firefly luciferase levels by chemiluminescence (Bright-Glo™ Promega). Maximum signal and fold-induction of firefly luciferase was observed with Opti-MEM® at 48 h of cell incubation (FIG. 19A) and with 40-75 ng/mL of TWEAK induction (FIG. 19B). These initial conditions formed the basis for transfer of the assay into a 384-well format and further optimization with respect to cell seeding density, induction time, and TWEAK concentration.

Figure 20:
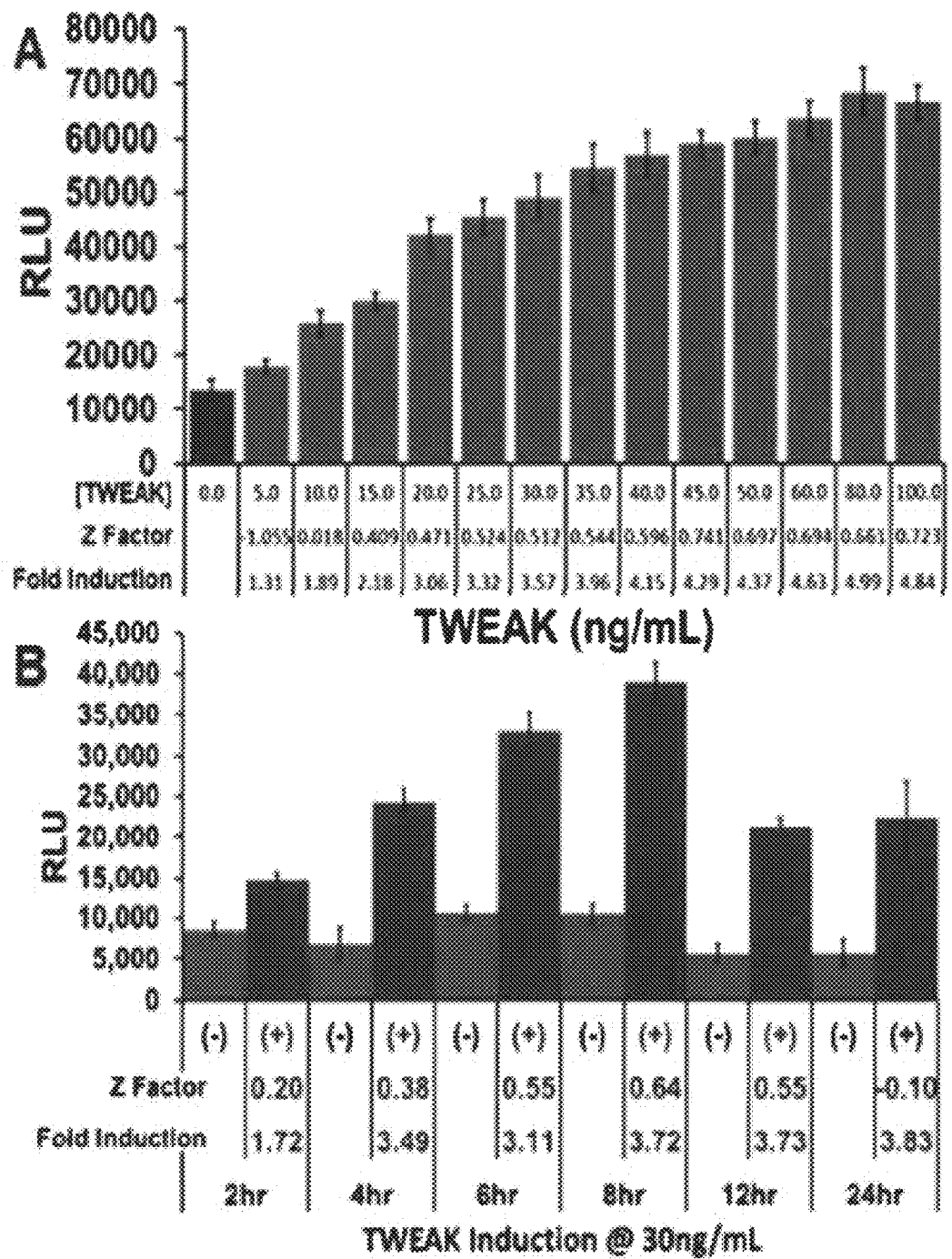
FIG. 20 depicts performance of Fn14-NF-κB-Luc Assay in 384-well plates. The HEK293 Fn14-NF-κB-Luc cell line was seeded at 2,500 cell/well in Opti-MEM® and allowed to attach for 48 hr then (20A) induced with 0-100 ng/ml of TWEAK for 8 hrs or (20B) induced for various times using 30 ng/ml of TWEAK in a 384-well tissue-culture treated plate. The chemiluminescent signals were determined as in TWEAK induction (FIG. 19B). Red bar=unstimulated cells; blue bar=TWEAK stimulated cells. These data are a representative set of triplicate experiments.

We achieved the same conclusion from both 96-well and 384-well format that signal-to-background and fold-inductions are increased with increasing TWEAK concentration, peaking between 40-80 ng/mL and decreased at 100 ng/mL (FIGS. 20A and 20B). As shown in FIG. 20B, the highest signal, signal-to-background, and fold-inductions are achieved after 8 hours of TWEAK induction. These conditions were further refined with respect to cell density (500-2500 cells per well), induction time (4-8 hr), and two TWEAK concentrations over a series of experiments in 384-well formats. We calculated performance characteristics of the assay, i.e., fold induction, Z' factor, and % CV of induced signal over these data using relevant guidelines, and an acceptable performance was set as Z' factor >0.5, % CV<10%, and Signal to Basal (S/B) Ratio (fold induction)>4.

In the majority of seeding density conditions and two different TWEAK concentrations, the assay performance improved with increasing TWEAK induction time. At 8 hours of TWEAK stimulation, the fold induction (S/B) and Z' factor was approximately 8-fold and 0.8, respectively, and the average % CV was 6.8%. Among all of the induction times and cell seeding densities, TWEAK stimulation at 40 ng/mL consistently yielded better fold induction, Z' factors, and % CVs than TWEAK stimulation at 30 ng/mL. Additionally, with all cell seeding densities tested, 1000-1500 cells/well appeared to yield the highest acceptable performance, considering the minimum amount of cells, time, and TWEAK needed to support a full screen of >365,000 compounds. Indeed, two additional experiments refined these conditions and set the optimal conditions to be 1000 cells/well with 8 hours induction of 40 ng/mL TWEAK.

Figure 21:
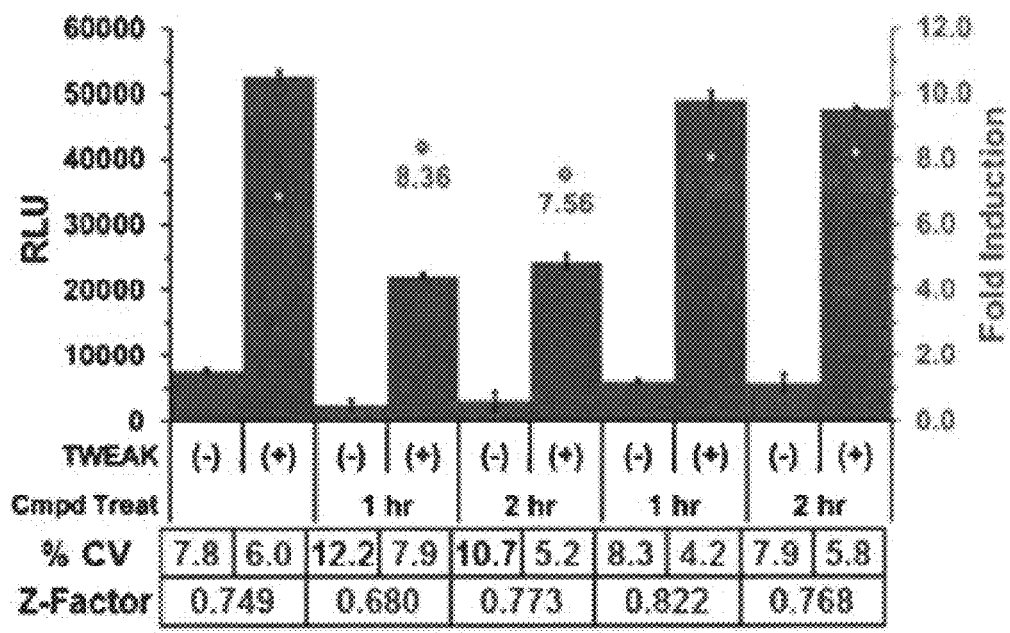
FIG. 21 depicts the robustness and reproducibility of the TWEAK induced Fn14-NF-κB Luc assay. 1000 cells/well in 384-well plate, 8 hr induction with 40 ng/mL TWEAK, 1 or 2 hr pre-incubation. This summarizes the performance characteristics fold induction (right y-axis), % CV, and Z-factor (bottom table) over three independent experiments over different days.

Moreover, we explored pre-incubation of compounds or DMSO control at 1 or 2 hours prior to TWEAK induction, and showed that there was no significant difference of the assay performance between pre-incubation times (FIG. 21). Due to the length of the assay duration, 1 hour of pre-incubation was selected. Therefore, we optimized the assay condition accordingly: 1000 cells/well, 8 hr induction with 40 ng/mL TWEAK, and 1 hr of compound pre-incubation. Importantly, three independent experiments performed over separate days obtained consistent results for the optimized screening conditions (FIG. 21). This demonstrated that the assay was robust and reproducible yielding acceptable performance values.

Figure 22:
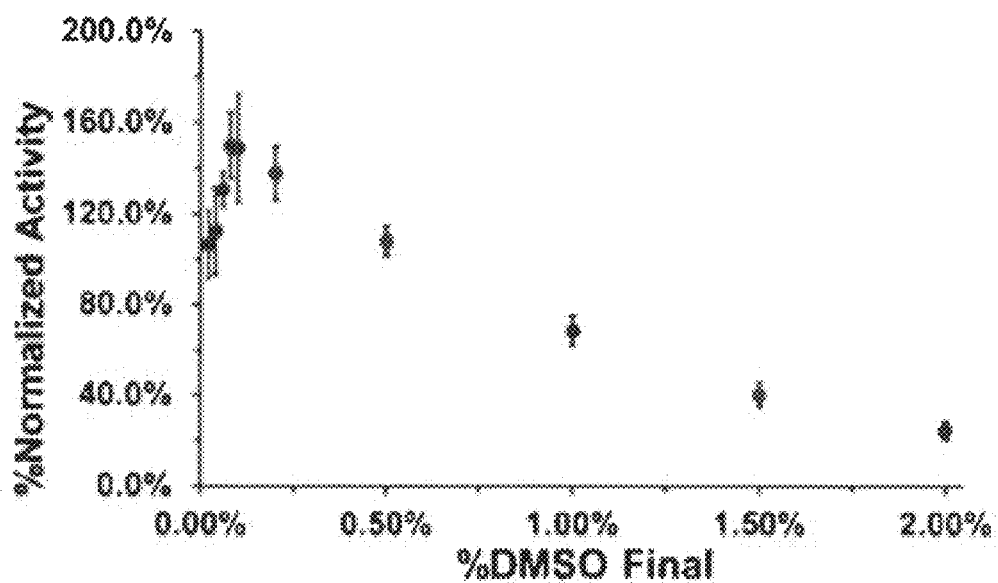
FIG. 22 depicts DMSO tolerance of the TWEAK induced Fn14-NF-κB Luc assay. Conditions: 1000 cells/well in a 384-well plate, 1 hr pre-incubation with final indicated DMSO concentration followed by 8 hr induction with 40 ng/mL TWEAK.
Figure 23:
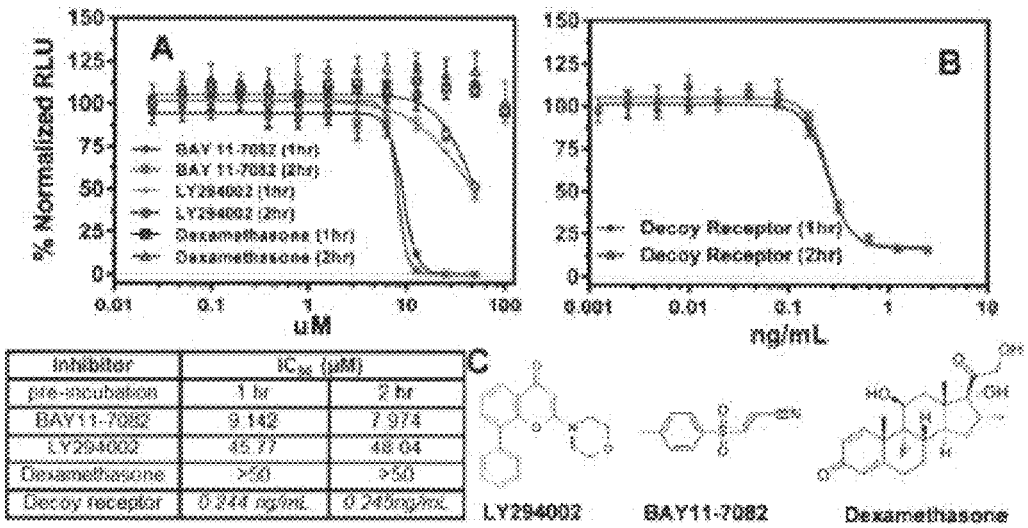
FIG. 23 depicts reference inhibitors of the TWEAK induced Fn14-NF-κB Luc assay. 23A, 1000 cells/well in 384-well plate, 1 or 2 hr pre-incubation of compounds or 23B decoy receptor prior to 40 ng/ml of TWEAK induction for 8 hr. Data acquisition and normalization was as described for FIG. 22; $IC_{50}$ was calculated with Prism 5 and summarized in the table. 23C, control compound structures.

Furthermore, determination of the DMSO tolerance (FIG. 22) showed that the assay was first stimulated then rapidly inhibited by DMSO concentrations much beyond 0.05% (v/v). A final 0.2% DMSO concentration was chosen to allow up to 20 µM compound treatment from 10 mM stocks in 100% DMSO. We realized that this could be a potential source of variation in the final assay; however the Labcyte Echo555™ that is used to transfer stock solutions has reproducibility of <3%. A final set of tests with two compounds (LY294002 and BAY-11-7082) at the optimized conditions demonstrated that the assay is robust and consistent whereas control Dexamethasone had no effect on the assay (FIG. 23A).

Example 14

Potency Estimations ($IC_{50}$) from Drug Dose-response Curves

We had three control molecules to test if the TWEAK induced Fn14-NF-KB-Luc assay was suitable to obtain inhibitor potency data to support structure activity relationship (SAR) studies: (1) LY294002, a PI3K inhibitor which should inhibit the pathway downstream of TWEAK-Fn14 binding; (2) BAY11-7082, an irreversible inhibitor of TNFα-stimulated IKBα phosphorylation and subsequent inhibition of NF-κB activity; and (3) a "decoy" receptor comprising the extracellular Fn14 domain lacking the cell-anchoring transmembrane domain, which ligates TWEAK thereby aborting Fn14 signaling. Additionally, dexamethasone is used as a negative signaling control. The structures of these compounds are show in FIG. 23C. There appeared to be no real difference of $IC_{50}$ values of reference compounds (FIG. 23A) or the Fn14 decoy receptor (FIG. 23B) upon pre-incubation for either 1 or 2 hr with cells before TWEAK induction (as expected for the large molecule TWEAK which exerts its effect external to the cell). Also this would be expected as pre-incubation is only a fraction of the total induction time. In addition, FIG. 23B demonstrates that TWEAK-Fn14 signaling pathway responds to both LY294002 and Bay11-7082 in a dose-dependent manner. Although there is no existing specific TWEAK-Fn14 inhibitor, we chose LY294002 and Bay11-7082 to be included as control compounds for the cell-based assay in the pilot HTS compound screen.

Example 15

Pilot HTS on the Prestwick Collection and Counterscreens to Confirm TWEAK Dependence Using the optimized conditions, we performed replicate screens of the 1,120 member Prestwick Collection of FDA-approved drugs comprising 4×384-well plates at final concentrations of 10 and 20 μM [final 0.1% and 0.2% DMSO (v/v)] for a total of four runs. The hit statistics for these four runs are summarized in Table 6.

TABLE 6

Hit statistics for duplicate runs at 10 and 20 μM screening concentrations

| Run # Conc. (μM) | Run 1 | | Run 2 | | In both Run 1 & 2 @ | | @ both 10 & 20 μM in | | In all 4 Runs 1 & 2 & 10 & 20 μM |
|---|---|---|---|---|---|---|---|---|---|
| | 10 | 20 | 10 | 20 | 10 | 20 | Run 1 | Run2 | |
| #Hits | 62 | 129 | 54 | 92 | 41 | 77 | 47 | 39 | 35 |
| Hit rate (%) | 5.5% | 11.5% | 4.8% | 8.2% | 3.7% | 6.9% | 4.2% | 3.5% | 3.1% |

In general, the compounds scoring as hits at 10 μM were more inhibitory at 20 μM and thus reported as hits. We noted that the concordance between runs 1 and 2 were good for each condition. Our data showed that 35 compounds were prioritized as hits in all 4 runs (both concentrations at both runs), thus representing a hit rate of 3.1%, which is somewhat high; however, cheminformatic filtering and counterscreens rapidly reduced this number.

Figure 24:
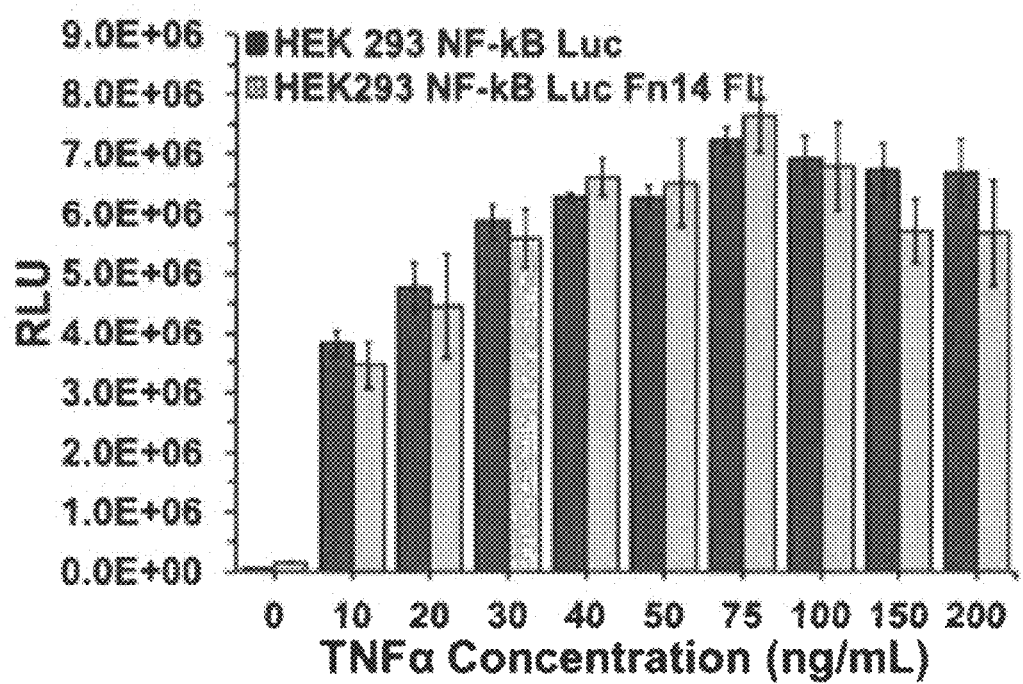
FIG. 24 depicts an initial counterscreen verification of TNFα-dependent Induction of Luciferase expression in HEK293 Fn14-NF-κB-Luc and HEK293 NF-κB Luc cell lines in a 96-well format. The control HEK293 NF-κB -Luc and HEK293 Fn14-NF-κB-Luc were seeded at 10,000 cell/well in Opti-MEM® plates and allowed to attach 48 hr and induced for 8 hr with 0-200 ng/mL of TWEAK in 96-well tissue-culture treated plates, then cells were lysed with Bright-Glo™ (Promega) and the Chemiluminescent signal was determined using Perkin Elmer Envision.

TNFα induction of the HEK293 NF-κB cell line was used as a counterscreen. In FIG. 24, the addition of TNFα to the HEK293 Fn14-NF-κB Luc and control HEK293 NF-KB Luc cell lines induced firefly luciferase expression in both across different TNFα concentrations, indicating that NF-κB activation downstream of TNFα TNFR1/TNFR2 likely runs in parallel to (independent of) TWEAK-Fn14 signaling.

Figure 25:
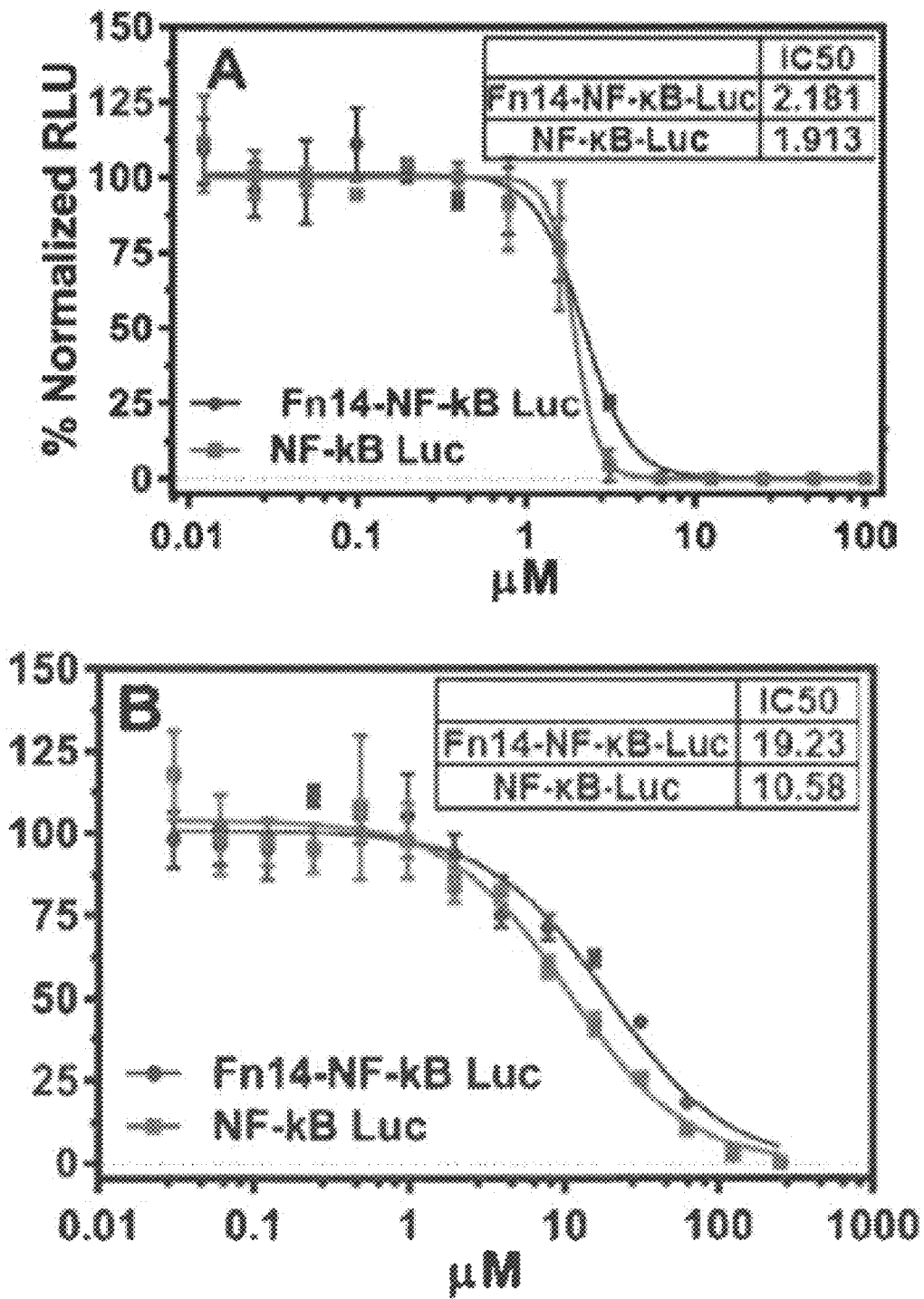
FIG. 25 depicts reference inhibitors of a TNFα induced counterscreen assay. 25A, 1000 cells/well in 384-well plate, 8 hr induction with 40 ng/ml TNFα, 1 hr pre-incubation with BAY 11-7082 or (25B) LY294002 prior to TNFα induction.

Furthermore, we tested the two control compounds, LY294002 and BAY11-7082, in a drug dose-response format. There was no significant difference in drug inhibition of TNFα activation in the Fn14 and control cell lines (FIG. 25). This suggested that the PI3K and NF-κB inhibitors are not specific to the TWEAK-Fn14 signaling pathway. We anticipate that compounds that directly affect Fn14 oligomerization, TWEAK ligation, or signaling proteins specific to the TWEAK-Fn14 signaling pathway that drive NF-κB activation will show minimal activity in the TNFα counterscreen assay.

Figure 26:
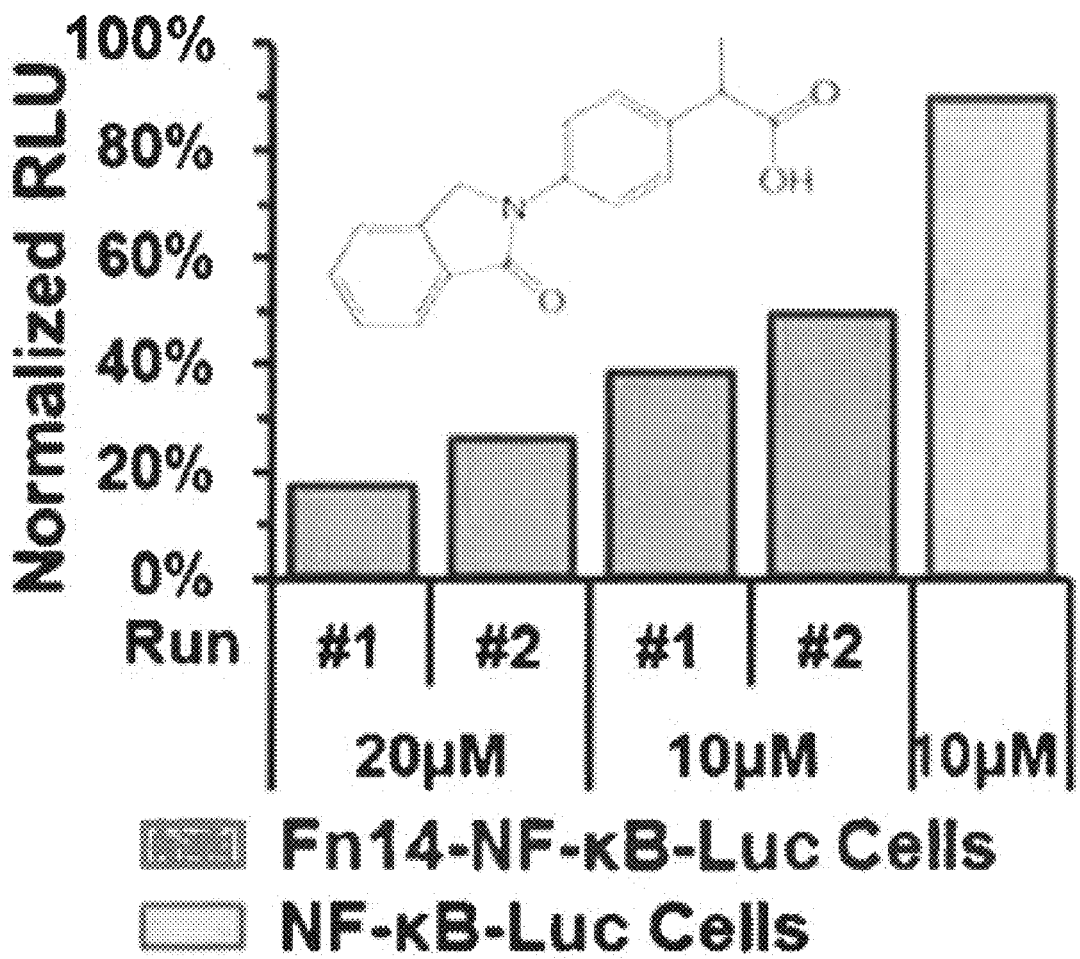
FIG. 26 depicts a hit example from the pilot screen. Indoprofen was tested at either 10 μM or 20 μM in HEK293 Fn14-NF-κB Luc cells for one hour followed by TWEAK induction at 40 ng/mL for 8 hours as wells as tested at 10 μM in NF-κB-Luc cells with TNFα induction at 40 ng/mL for 8 hours. Two independent runs on HEK293 Fn14-NF-κB Luc cells were performed. Luminescent signal for each condition was measured and normalized to DMSO control.

In order to eliminate the false positive hits from the pilot screen, we further performed the counterscreen by testing 35 "positives" from the Prestwick collection against HEK293 NF-KB-Luc control cell lines induced by TNFα. From this experiment we eliminated 28 compounds that inhibited luciferase expression after TNFα induction of HEK293 NF-KB Luc cells. Thus, after counterscreen only 7 compounds appeared to be specific inhibitors to the TWEAK-Fn14 signaling pathway. One "hit" example was Indoprofen, which demonstrated drug sensitivity in a dose-dependent manner in Fn14 NF-KB-Luc cell line induced with TWEAK, whereas no significant effect was observed in NF-KB Luc cells induced with TNFα (FIG. 26). Overall, through our pilot primary screen and counterscreen, our hit rate approached 0.6% for this targeted collection. We expect a random collection to yield a lower hit-rate, which will be further reduced through the chemoinformatic filtering for luciferase false positive artifacts. Furthermore, secondary assays will be critical as cytotoxic false positives appeared to be about 80% from our pilot screen. Overall the final hit rate of bona fide, validated hits is expected to be on the order of 0.2-0.4%, well within the capacity for the downstream assays in the project flowchart (FIG. 17)

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of inhibiting the TWEAK-Fn14 pathway in a cell, the method comprising administering to the cell an Fn14 antagonist comprising a compound of Formula (II):

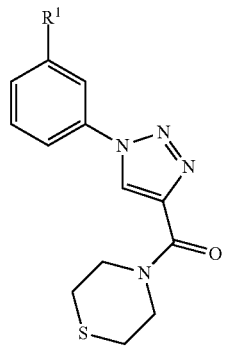

or a salt thereof, wherein

R$^1$ is —H, —OH, —NH$_2$, —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N(alkyl)(alkyl), —NHC(O)(alkyl), —N(alkyl)C(O)(alkyl), —OC(O)O(alkyl), —OC(O)NH$_2$, —OC(O)NH(alkyl), —OC(O)N(alkyl)(alkyl), —CHNH, —CHN(alkyl), —SO$_2$NH$_2$, and a vehicle, excipient, and/or carrier.

2. The method of claim 1, wherein R$^1$ of the compound or salt is —H, —OH, halo, —C$_{1-6}$ alkyl, or —O—C$_{1-6}$ alkyl.

3. The method of claim 2, wherein the compound is:

IIa:

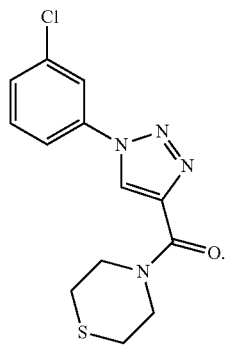

4. A pharmaceutical composition comprising a synergistic combination of an Fn14 antagonist comprising a compound of Formula (II):

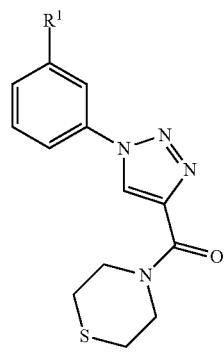

or a salt thereof, wherein

R$^1$ is —H, —OH, —NH$_2$, —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —OCF$_3$, —C(O)O(alkyl), —OC(O)(alkyl), —C(O)NH$_2$, —C(O)NH(alkyl), —C(O)N (alkyl)(alkyl), —NHC(O)(alkyl), —N(alkyl)C(O)(alkyl), —OC(O)O(alkyl), —OC(O)NH₂, —OC(O)NH(alkyl), —OC(O)N(alkyl)(alkyl), —CHNH, —CHN(alkyl), —SO₂NH₂;

and a chemotherapeutic alkylating agent.

5. The pharmaceutical composition of claim 4, wherein the chemotherapeutic alkylating agent is selected from the group consisting of mechtorethamine, cyclophosphamide, chlorambucil, melphalane, trofosfamide, ifosfamide, carmustine, lomustine, darcarbazine, temozolomide (TMZ), and mitomycine C.

6. A new method of treating a cancer selected from the group consisting of a brain tumor, glioblastoma, breast cancer, esophageal cancer, lung cancer, and melanoma, the method comprising administering to a subject in need thereof an effective amount of an Fn14 antagonist comprising a compound of Formula (II):

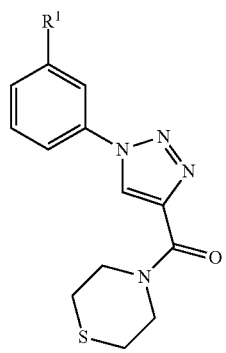

or a salt thereof, wherein $R^1$ is —H, —OH, —NH₂, —N(alkyl)(alkyl), hydrocarbyl, —O-hydrocarbyl, aryl, —O-aryl, aralkyl, —O-aralkyl, heteroaryl, —O-heteroaryl, heterocyclyl, —O-heterocyclyl, halo, —OCF₃, —C(O)O(alkyl), —OC(O)(alkyl), —C(O)NH₂, —C(O)NH(alkyl), —C(O)N(alkyl)(alkyl), —NHC(O)(alkyl), —N(alkyl)C(O)(alkyl), —OC(O)O(alkyl), —OC(O)NH₂, —OC(O)NH(alkyl), —OC(O)N(alkyl)(alkyl), —CHNH, —CHN(alkyl), —SO₂NH₂;

and a vehicle, excipient, and/or carrier.

7. The method of claim 6, wherein the compound inhibits the TWEAK-Fn14 pathway in the subject.

8. The method of claim 6, wherein $R^1$ of the compound or salt is —H, —OH, halo, —$C_{1-6}$alkyl.

9. The method of claim 8, wherein the compound is:

IIa:

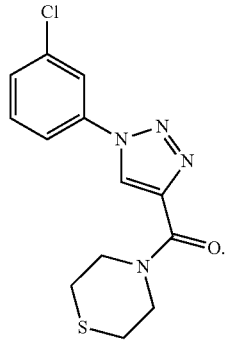

* * * * *